United States Patent
Nakashima et al.

(10) Patent No.: US 9,758,502 B2
(45) Date of Patent: Sep. 12, 2017

(54) DIHYDROPYRONE COMPOUNDS AND HERBICIDES COMPRISING THE SAME

(71) Applicant: SUMITOMO CHEMICAL COMPANY, LIMITED, Tokyo (JP)

(72) Inventors: Yosuke Nakashima, Tokyo (JP); Yoshinobu Jin, Hyogo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/437,859

(22) PCT Filed: Nov. 27, 2013

(86) PCT No.: PCT/JP2013/082513
§ 371 (c)(1),
(2) Date: Apr. 23, 2015

(87) PCT Pub. No.: WO2014/084407
PCT Pub. Date: Jun. 5, 2014

(65) Prior Publication Data
US 2015/0299156 A1 Oct. 22, 2015

(30) Foreign Application Priority Data
Nov. 28, 2012 (JP) ................. 2012-259421

(51) Int. Cl.
| | | |
|---|---|---|
| *A01N 43/78* | (2006.01) | |
| *A01N 43/40* | (2006.01) | |
| *A01N 43/54* | (2006.01) | |
| *A01N 43/58* | (2006.01) | |
| *C07D 311/42* | (2006.01) | |
| *C07D 405/12* | (2006.01) | |
| *C07D 409/12* | (2006.01) | |
| *C07D 417/12* | (2006.01) | |
| *A01N 43/60* | (2006.01) | |
| *A01N 43/16* | (2006.01) | |

(Continued)

(52) U.S. Cl.
CPC ............ *C07D 311/42* (2013.01); *A01N 43/16* (2013.01); *A01N 43/40* (2013.01); *A01N 43/54* (2013.01); *A01N 43/58* (2013.01); *A01N 43/60* (2013.01); *A01N 43/78* (2013.01); *C07D 309/32* (2013.01); *C07D 405/12* (2013.01); *C07D 407/12* (2013.01); *C07D 409/12* (2013.01); *C07D 413/12* (2013.01); *C07D 417/12* (2013.01)

(58) Field of Classification Search
CPC .. C07D 311/42; C07D 309/32; C07D 405/12; C07D 407/12; C07D 409/12; C07D 413/12; C07D 417/12; A01N 43/16; A01N 43/54; A01N 43/58; A01N 43/60; A01N 43/78
See application file for complete search history.

(56) References Cited

U.S. PATENT DOCUMENTS 5,393,729 A * 2/1995 Fischer .................. A01N 43/16 504/128
6,906,007 B2 * 6/2005 Fischer .................. A01N 43/16 504/292

(Continued)

FOREIGN PATENT DOCUMENTS

| CN | 1085554 | 4/1994 |
| CN | 1443181 | 9/2003 |

(Continued)

OTHER PUBLICATIONS

Bibliographic Data of CL2007003642 (A1) issued May 30, 2008.
Office Action issued Mar. 28, 2016 in corresponding Chilean application No. PCT/2015-001404.
International Search Report issued Jan. 29, 2014 in International Application No. PCT/JP2013/082513.
International Preliminary Report on Patentability issued Jun. 2, 2015 in International Application No. PCT/JP2013/082513.
Office Action issued Dec. 2, 2015 in corresponding Chinese patent application No. 201380061922.7 (with English translation).
Chilean Office Action issued Sep. 29, 2016 in corresponding Chilean Application No. 2015-01404 with English translation.
Japanese Office Action, issued Jun. 6, 2017 in corresponding Japanese application No. 2015-543683, with English language translation.

*Primary Examiner* — John Pak
*Assistant Examiner* — Erin Hirt
(74) *Attorney, Agent, or Firm* — Wenderoth, Lind & Ponack, L.L.P.

(57) ABSTRACT

The present invention provides a compound having an excellent efficacy for controlling weeds. A dihydropyrone compound of formula (I): wherein m is 1, 2 or 3; n is an integer of any one of 1 to 5; X represents O, S, S(O) or $S(O)_2$; $R^1$ represents a hydrogen atom or a methyl group; $R^2$ and $R^3$ represents a hydrogen atom, an $C_{1-6}$ alkyl group and the like; when X represents S, S(O) or $S(O)_2$, $R^4$ represents an $C_{1-6}$ alkyl group, a $C_{1-6}$ haloalkyl group, an $C_{6-10}$ aryl group or a five- to six-membered heteroaryl group, and X represents O, S, S(O) or $S(O)_2$, $R^4$ represents an $C_{6-10}$ aryl group or a five- to six-membered heteroaryl group; G represents a hydrogen atom and the like; Z represents a halogen atom, a cyano group, a nitro group, a phenyl group, an $C_{1-6}$ alkyl group and the like; is useful as an active ingredient for herbicides.

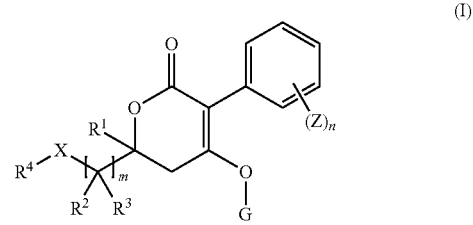

10 Claims, No Drawings

(51) Int. Cl.
*C07D 309/32* (2006.01)
*C07D 407/12* (2006.01)
*C07D 413/12* (2006.01)

(56) References Cited

U.S. PATENT DOCUMENTS

| | | |
|---|---|---|
| 2004/0102516 A1 | 5/2004 | Fischer et al. |
| 2005/0187110 A1 | 8/2005 | Maetzke et al. |
| 2008/0026943 A1 | 1/2008 | Fischer et al. |
| 2010/0173774 A1 | 7/2010 | Muehlebach et al. |
| 2010/0210466 A1 | 8/2010 | Muehlebach et al. |
| 2014/0005389 A1 | 1/2014 | Mathews et al. |
| 2015/0274691 A1* | 10/2015 | Nakashima ............ A01N 43/40 504/251 |

FOREIGN PATENT DOCUMENTS

| | | |
|---|---|---|
| CN | 101010306 | 8/2007 |
| CN | 101605771 | 12/2009 |
| CN | 102007097 | 4/2011 |
| EP | 0 588 137 | 8/1993 |
| JP | 9-505294 | 5/1997 |
| JP | 2004-501144 | 1/2004 |
| JP | 2008-505063 | 2/2008 |
| WO | 95/14012 | 5/1995 |
| WO | 01/98288 | 12/2001 |
| WO | 2006/002810 | 1/2006 |
| WO | 2008/071405 | 6/2008 |
| WO | 2008/110308 | 9/2008 |
| WO | 2012/165648 | 12/2012 |

* cited by examiner

DIHYDROPYRONE COMPOUNDS AND HERBICIDES COMPRISING THE SAME

This application claims priority to and the benefit of Japanese Patent Application No. 2012-259421 filed Nov. 28, 2012, the entire contents of which are incorporated herein by reference.

TECHNICAL FIELD

The present invention relates to dihydropyrone compounds and herbicides comprising the same.

BACKGROUND ART

Heretofore, some compounds that are useful as active ingredients in herbicides for controlling weeds have been developed and some compounds having an efficacy for controlling weeds have been found.

Some dihydropyrone compounds having herbicidal activity have been known (see Patent Documents 1 to 3).

CITATION LIST

Patent Document

Patent Document 1: JP 9-505294 A
Patent Document 2: JP 2004-501144 A
Patent Document 3: JP 2008-505063 A

SUMMARY OF THE INVENTION

An object of the present invention is to provide a compound having an excellent efficacy for controlling weeds.

The present inventors have intensively studied to find that compounds having an excellent efficacy for controlling weeds and as a result, found that a dihydropyrone compound of the following formula (I) has an excellent efficacy for controlling weeds, which thus have completed the present invention.

Specifically, the present invention includes the followings [1] to [11].

[1] A dihydropyrone compound of formula (I):

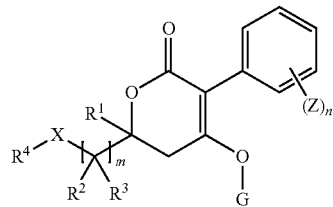

(I)

[wherein
m is 1, 2 or 3;
n is an integer of any one of 1 to 5;
X represents O, S, S(O) or S(O)$_2$;
R$^1$ represents a hydrogen atom or a methyl group;
R$^2$ and R$^3$ represent independently of each other a hydrogen atom, a halogen atom, an C$_{1-6}$ alkyl group, a C$_{1-6}$ haloalkyl group, a C$_{3-8}$ cycloalkyl group or a C$_{3-8}$ halocycloalkyl group, alternatively R$^2$ and R$^3$ connect each other to represent an C$_{2-5}$ alkylene chain, or R$^2$ and R$^3$ combine each other to represent an C$_{1-3}$ alkylidene group optionally having one or more halogen atoms (with the proviso that when m is 2 or 3, two or three R$^2$ may be same or different to each other and two or three R$^3$ may be same or different to each other);

when X represents S, S(O) or S(O)$_2$, R$^4$ represents a C$_{3-7}$ cycloalkyl group optionally substituted with methyl group or ethyl group, an C$_{1-18}$ alkyl group, a C$_{1-18}$ haloalkyl group, an (C$_{1-6}$ alkoxy) C$_{1-12}$ alkyl group, a (C$_{1-6}$ alkylthio)C$_{1-12}$ alkyl group, an C$_{3-18}$ alkenyl group, a C$_{3-18}$ haloalkenyl group, an C$_{3-18}$ alkynyl group, a C$_{3-18}$ haloalkynyl group, an C$_{6-10}$ aryl group or a five- to six-membered heteroaryl group {with the proviso that the C$_{6-10}$ aryl group and the five- or six-membered heteroaryl group may have optionally one or more substituents selected from the group consisting of a halogen atom, a cyano group, a nitro group, an amino group, an (C$_{1-6}$ alkyl)amino group, an (C$_{1-6}$ alkyl) (C$_{1-6}$ alkyl) amino group, a pentafluorothio group, an C$_{1-6}$ alkyl group, an C$_{2-6}$ alkenyl group, an C$_{2-6}$ alkynyl group, an C$_{1-6}$ alkoxy group, an C$_{1-6}$ alkylthio group, an C$_{3-6}$ alkenyloxy group, an C$_{3-6}$ alkynyloxy group, an C$_{6-10}$ aryl group, an C$_{6-10}$ aryloxy group, an C$_{1-6}$ alkylsulfinyl group, an C$_{1-6}$ alkylsulfonyl group, a hydroxyl group, an (C$_{1-6}$ alkyl)carbonyl group, a hydroxycarbonyl group, a (C$_{1-6}$ alkoxy) carbonyl group and an (C$_{6-10}$ aryl)C$_{1-6}$ alkoxy group, and when two or more substituents exist, the substituents may be same or different to each other; and the C$_{1-6}$ alkyl group, the C$_{2-6}$ alkenyl group, the C$_{2-6}$ alkynyl group, the C$_{1-6}$ alkoxy group, the C$_{1-6}$ alkylthio group, the C$_{3-6}$ alkenyloxy group, the C$_{3-6}$ alkynyloxy group, the C$_{6-10}$ aryl group, the C$_{6-10}$ aryloxy group, the C$_{1-6}$ alkylsulfinyl group, the C$_{1-6}$ alkylsulfonyl group, the (C$_{1-6}$ alkoxy)carbonyl group and the (C$_{6-10}$ aryl) C$_{1-6}$ alkoxy group may each have one or more halogen atoms or C$_{1-3}$ haloalkyl groups, and when two or more halogen atoms or C$_{1-3}$ haloalkyl groups exist, the halogen atoms or the C$_{1-3}$ haloalkyl groups may be same or different to each other respectively};

when X represents O, R$^4$ represents an C$_{6-10}$ aryl group or a five- to six-membered heteroaryl group {with the proviso that the C$_{6-10}$ aryl group and the five- or six-membered heteroaryl group may have optionally one or more substituents selected from the group consisting of halogen atom, a cyano group, a nitro group, an amino group, an (C$_{1-6}$ alkyl)amino group, an (C$_{1-6}$ alkyl) (C$_{1-6}$ alkyl)amino group, a pentafluorothio group, an C$_{1-6}$ alkyl group, an C$_{2-6}$ alkenyl group, an C$_{2-6}$ alkynyl group, an C$_{1-6}$ alkoxy group, an C$_{1-6}$ alkylthio group, an C$_{3-6}$ alkenyloxy group, an C$_{3-6}$ alkynyloxy group, an C$_{6-10}$ aryl group, an C$_{6-10}$ aryloxy group, an C$_{1-6}$ alkylsulfinyl group, an C$_{1-6}$ alkylsulfonyl group, a hydroxyl group, an (C$_{1-6}$ alkyl)carbonyl group, a hydroxycarbonyl group, a (C$_{1-6}$ alkoxy)carbonyl group and an (C$_{6-10}$ aryl)C$_{1-6}$ alkoxy group, and when two or more substituents exist, the substituents may be same or different to each other; and the C$_{1-6}$ alkyl group, the C$_{2-6}$ alkenyl group, the C$_{2-6}$ alkynyl group, the C$_{1-6}$ alkoxy group, the C$_{1-6}$ alkylthio group, the C$_{3-6}$ alkenyloxy group, the C$_{3-6}$ alkynyloxy group, the C$_{6-10}$ aryl group, the C$_{6-10}$ aryloxy group, the C$_{1-6}$ alkylsulfinyl group, the C$_{1-6}$ alkylsulfonyl group, the (C$_{1-6}$ alkoxy)carbonyl group and the (C$_{6-10}$ aryl)C$_{1-6}$ alkoxy group may each have one or more halogen atoms or C$_{1-3}$ haloalkyl groups, and when two or more halogen atoms or C$_{1-3}$ haloalkyl groups exist, the halogen atoms or the C$_{1-3}$ haloalkyl groups may be same or different to each other respectively};

G represents a hydrogen atom or a group of any one of the following formulae:

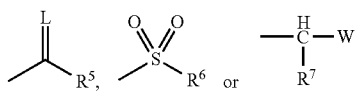

{wherein

L represents an oxygen atom (O) or a sulfur atom (S);

$R^5$ represents an $C_{1-6}$ alkyl group, a $C_{3-8}$ cycloalkyl group, an $C_{2-6}$ alkenyl group, an $C_{2-6}$ alkynyl group, an $C_{6-10}$ aryl group, an $(C_{6-10}$ aryl)$C_{1-6}$ alkyl group, an $C_{1-6}$ alkoxy group, a $C_{3-8}$ cycloalkoxy group, an $C_{3-6}$ alkenyloxy group, an $C_{3-6}$ alkynyloxy group, an $C_{6-10}$ aryloxy group, an $(C_{6-10}$ aryl)$C_{1-6}$ alkoxy group, an $(C_{1-6}$ alkyl)$(C_{1-6}$ alkyl)amino group, an $(C_{3-6}$ alkenyl)$(C_{3-6}$ alkenyl)amino group, an $(C_{1-6}$ alkyl)$(C_{6-10}$ aryl)amino group or a five- to six-membered heteroaryl group (with the proviso that these groups may each one or more halogen atoms, and when two or more halogen atoms exist, the halogen atoms may be same or different to each other; and the $C_{3-8}$ cycloalkyl group, the $C_{6-10}$ aryl group, an aryl moiety of the $(C_{6-10}$ aryl)$C_{1-6}$ alkyl group, the $C_{3-8}$ cycloalkoxy group, the $C_{6-10}$ aryloxy group, an aryl moiety of the $(C_{6-10}$ aryl)$C_{1-6}$ alkoxy group, an aryl moiety of the $(C_{1-6}$ alkyl) $(C_{6-10}$ aryl)amino group and a five- to six-membered heteroaryl group may each have one or more $C_{1-6}$ alkyl groups, and when two or more $C_{1-6}$ alkyl groups exist, the alkyl groups may be same or different to each other);

$R^6$ represents an $C_{1-6}$ alkyl group, an $C_{6-10}$ aryl group or an $(C_{1-6}$ alkyl)$(C_{1-6}$ alkyl)amino group (with the proviso that these groups may each have one or more halogen atoms and when two or more halogen atoms exist, the halogen atoms may be same or different to each other; and the $C_{6-10}$ aryl group may have optionally one or more $C_{1-6}$ alkyl groups and when two or more $C_{1-6}$ alkyl groups exist, the alkyl groups may be same or different to each other);

$R^7$ represents a hydrogen atom or an $C_{1-6}$ alkyl group;

W represents an $C_{1-6}$ alkoxy group, an $C_{1-6}$ alkylthio group, an $C_{1-6}$ alkylsulfinyl group or an $C_{1-6}$ alkylsulfonyl group (with the proviso that these groups may each have one or more halogen atoms and when two or more halogen atoms exist, the halogen atoms may be same or different to each other)};

Z represents a halogen atom, a cyano group, a nitro group, an $C_{1-6}$ alkyl group, an $C_{2-6}$ alkenyl group, an $C_{2-6}$ alkynyl group, an $C_{1-6}$ alkoxy group, an $(C_{1-6}$ alkyl)carbonyl group, an $C_{1-6}$ alkylthio group, an $C_{6-10}$ aryloxy group, five- or six-membered heteroaryloxy group, a $C_{3-8}$ cycloalkyl group, an $C_{6-10}$ aryl group or a five- to six-membered heteroaryl group {with the proviso that the $C_{1-6}$ alkyl group, the $C_{2-6}$ alkenyl group, the $C_{2-6}$ alkynyl group, the $C_{1-6}$ alkoxy group, the $(C_{1-6}$ alkyl)carbonyl group and the $C_{1-6}$ alkylthio group may each have one or more halogen atoms, and when two or more halogen atoms exist, the halogen atoms may be same or different to each other; and the $C_{6-10}$ aryl group, the five- to six-membered heteroaryl group, the $C_{6-10}$ aryloxy group and the five- to six-membered heteroaryloxy group may each have one or more substituents selected from the group consisting of a halogen atom, an $C_{1-6}$ alkyl group and a $C_{1-6}$ haloalkyl group, and when two or more substituents exist, the substituents may be same or different to each other; and the $C_{3-8}$ cycloalkyl group may have optionally one or more substituents selected from the group consisting of a halogen atom and an $C_{1-6}$ alkyl group, and when two or more substituents exist, the substituents may be same or different to each other; when n is an integer of 2 or more, Z may be same or different to each other}] (hereinafter, sometimes referred to as "the present compound").

[2] The dihydropyrone compound of [1] wherein m is 1, 2 or 3;

n is an integer of any one of 1 to 3;

$R^1$ represents a hydrogen atom or a methyl group;

$R^2$ and $R^3$ represent independently of each other a hydrogen atom or an $C_{1-3}$ alkyl group, alternatively $R^2$ and $R^3$ connect each other to represent an $C_{2-5}$ alkylene chain (with the proviso that when m is 2 or 3, two or three $R^2$ may be same or different to each other and two or three $R^3$ may be same or different to each other);

G represents a hydrogen atom or a group of any one of the following formulae:

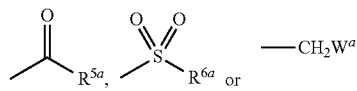

{wherein $R^{5a}$ represents an $C_{1-6}$ alkyl group, an $C_{6-10}$ aryl group, an $C_{1-6}$ alkoxy group, an $C_{3-6}$ alkenyloxy group, an $C_{3-6}$ alkynyloxy group or an $C_{6-10}$ aryloxy group;

$R^{6a}$ represents an $C_{1-6}$ alkyl group; and $W^a$ represents an $C_{1-3}$ alkoxy group};

Z represents a halogen atom, an $C_{1-3}$ alkyl group, an $C_{2-6}$ alkenyl group, an $C_{2-6}$ alkynyl group, an $C_{1-3}$ alkoxy group, a $C_{3-8}$ cycloalkyl group, a nitro group, a phenyl group or a five- to six-membered heteroaryloxy group (with the proviso that the $C_{1-3}$ alkyl group, the $C_{2-6}$ alkenyl group, the $C_{2-6}$ alkynyl group, the $C_{1-3}$ alkoxy group, the phenyl group and the five- to six-membered heteroaryloxy group may have optionally one or more halogen atoms, and when two or more halogen atoms exist, the halogen atoms may be same or different to each other).

[3] The dihydropyrone compound of [2] wherein m is 2;

$R^2$ and $R^3$ represents independently of each other a hydrogen atom, a methyl group or an ethyl group, alternatively $R^2$ and $R^3$ connect each other to represent an ethylene chain (with the proviso that two $R^2$ may be same or different to each other and two $R^3$ may be same or different to each other);

G represents a hydrogen atom, an acetyl group, propionyl group, a butylcarbonyl group, a benzoyl group, a methylsulfonyl group, a methoxycarbonyl group, an ethoxycarbonyl group, an allyloxycarbonyl group, a phenoxycarbonyl group, a methoxymethyl group or an ethoxymethyl group;

$R^9$ represents a hydrogen atom, a 2-nitrophenylsulfonyl group or a methyl group;

Z represents a methyl group, an ethyl group, a phenyl group, a vinyl group, a cyclopropyl group, a nitro group, a fluorine atom, a chlorine atom, a bromine atom, a methoxy group, a trifluoromethyl group, a 5-trifluoromethyl-2-chloropyridyloxy group or an ethynyl group.

[4] The dihydropyrone compound of any one of [1] to [3] wherein

X represents S, S(O) or S(O)$_2$; and $R^4$ represents a $C_{3-7}$ cycloalkyl group optionally substituted with methyl group or ethyl group, an $C_{1-6}$ alkyl group, a $C_{1-6}$ haloalkyl group, an $C_{3-6}$ alkenyl group, a $C_{3-6}$ haloalkenyl group, an $C_{3-6}$ alkynyl group, a $C_{3-6}$ haloalkynyl group, a phenyl group, a 2-pyridyl group, a 3-pyridyl group, a 4-pyridyl group, a 2-pyrimidinyl group, a 2-furyl group, a 2-thienyl group or a 2-thiazolyl group, an 2-oxazolyl group, a 2-(1,3,4-thiadiazolyl) group or a 5-tetrazoly group {with proviso that the phenyl group, the 2-pyridyl group, the 3-pyridyl group, the 4-pyridyl group, the 2-pyrimidinyl group, the 2-furyl group, the 2-thienyl group, the 2-thiazolyl group, the 2-oxazolyl group, the 2-(1,3,4-thiadiazolyl) group or the 5-tetrazoly group may have optionally one or more substituents selected from the group consisting of a halogen atom, an $C_{1-3}$ alkyl group, a hydroxyl group, an ($C_{1-3}$ alkyl) carbonyl group, a ($C_{1-3}$ alkoxy)carbonyl group, an $C_{1-3}$ alkoxy group, a $C_{1-3}$ haloalkyl group, an $C_{1-3}$ alkylthio group, a $C_{1-3}$ haloalkylthio group, a cyano group, a nitro group, an amino group, a pentafluorothio group, a benzoylamino group and a $C_{1-3}$ haloalkoxy group, and when two or more substituents exist, the substituents may be same or different to each other.

[5] The dihydropyrone compound of [4] wherein
X represents S, S(O) or S(O)$_2$; and
R$^4$ represents a methyl group, an ethyl group, a propyl group, a phenyl group, a 2-pyridyl group, a 3-pyridyl group, a 4-pyridyl group, a 2-pyrimidinyl group, a 2-furyl group, a 2-thienyl group, a 2-thiazolyl group, an 2-oxazolyl group, a 2-(1,3,4-thiadiazolyl) group or a 5-tetrazoly group {with proviso that the phenyl group, the 2-pyridyl group, the 3-pyridyl group, the 4-pyridyl group, the 2-pyrimidinyl group, the 2-furyl group, the 2-thienyl group, a 2-thiazolyl group, an 2-oxazolyl group, a 2-(1,3,4-thiadiazolyl) group or a 5-tetrazoly group may have optionally one or more substituents selected from the group consisting of a chlorine atom, a bromine atom, an iodine atom, a fluorine atom, a methyl group, an ethyl group, an isopropyl group, a t-butyl group, a methoxy group, a nitro group, an amino group, a cyano group, a hydroxyl group, an acetyl group, a methoxycarbonyl group, a pentafluorothio group, a pentafluoroethyl group, a difluoroethyl group, a heptafluoroisopropyl group, a trifluoromethylthio group, benzoylamino group, a trifluoromethoxy group and a trifluoromethyl group.

[6] The dihydropyrone compound of any one of [1] to [3] wherein
X represents O; and
R$^4$ represents a phenyl group, a 2-pyridyl group, a 3-pyridyl group, a 4-pyridyl group, a 2-pyrimidinyl group, a 2-furyl group, a 2-thienyl group, a 2-thiazolyl group, an 2-oxazolyl group, a 2-(1,3,4-thiadiazolyl) group or a 5-tetrazoly group {with proviso that the phenyl group, the 2-pyridyl group, the 3-pyridyl group, the 4-pyridyl group, the 2-pyrimidinyl group, the 2-furyl group, the 2-thienyl group, the 2-thiazolyl group, the 2-oxazolyl group, the 2-(1,3,4-thiadiazolyl) group or the 5-tetrazoly group may have optionally one or more substituents selected from the group consisting of a halogen atom, an $C_{1-3}$ alkyl group, hydroxyl group, an ($C_{1-3}$ alkyl)carbonyl group, ($C_{1-3}$ alkoxy) carbonyl group, an $C_{1-3}$ alkoxy group, a $C_{1-3}$ haloalkyl group, an $C_{1-3}$ alkylthio group, a $C_{1-3}$ haloalkylthio group, a cyano group, a nitro group, an amino group, a pentafluorothio group, a benzoylamino group and a $C_{1-3}$ haloalkoxy group, and when two or more substituents exist, the substituents may be same or different to each other.

[7] The dihydropyrone compound of [6] wherein
X represents O; and
R$^4$ represents a phenyl group, a 2-pyridyl group, a 3-pyridyl group, a 4-pyridyl group, a 2-pyrimidinyl group, a 2-furyl group, a 2-thienyl group, a 2-thiazolyl group, an 2-oxazolyl group, a 2-(1,3,4-thiadiazolyl) group or a 5-tetrazoly group {with proviso that the phenyl group, the 2-pyridyl group, the 3-pyridyl group, the 4-pyridyl group, the 2-pyrimidinyl group, the 2-furyl group, the 2-thienyl group, the 2-thiazolyl group, the 2-oxazolyl group, the 2-(1,3,4-thiadiazolyl) group or the 5-tetrazoly group may have optionally one or more substituents selected from the group consisting of a chlorine atom, a bromine atom, an iodine atom, a fluorine atom, a methyl group, an ethyl group, an isopropyl group, a t-butyl group, a methoxy group, a nitro group, an amino group, a cyano group, a hydroxyl group, an acetyl group, a methoxycarbonyl group, a pentafluorothio group, a pentafluoroethyl group, a difluoroethyl group, a heptafluoroisopropyl group, a trifluoromethylthio group, a benzoylamino group, a trifluoromethoxy group and a trifluoromethyl group.

[8] The dihydropyrone compound of any one of [1] to [7] wherein G represents a hydrogen atom.

[9] A herbicide comprising a dihydropyrone compound of any one of [1] to [8] as an active ingredient and an inert carrier.

[10] A method for controlling weeds which comprises applying an effective amount of a dihydropyrone compound of formula (I) to weeds or soil where weeds grow, wherein the dihydropyrone compound of formula (I) is a compound represented by a formula:

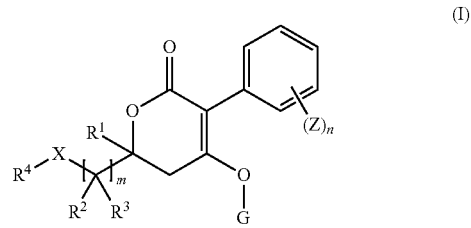

[wherein
m is 1, 2 or 3;
n is an integer of any one of 1 to 5;
X represents O, S, S(O) or S(O)$_2$;
R$^1$ represents a hydrogen atom or a methyl group;
R$^2$ and R$^3$ represent independently of each other a hydrogen atom, a halogen atom, an $C_{1-6}$ alkyl group, a $C_{1-6}$ haloalkyl group, a $C_{3-8}$ cycloalkyl group or a $C_{3-8}$ halocycloalkyl group, alternatively R$^2$ and R$^3$ connect each other to represent an $C_{2-5}$ alkylene chain, or R$^2$ and R$^3$ combine each other to represent an $C_{1-3}$ alkylidene group optionally having one or more halogen atoms (with the proviso that when m is 2 or 3, two or three R$^2$ may be same or different to each other and two or three R$^3$ may be same or different to each other);

when X represents S, S(O) or S(O)$_2$, R$^4$ represents a $C_{3-7}$ cycloalkyl group optionally substituted with methyl group or ethyl group, an $C_{1-18}$ alkyl group, a $C_{1-18}$ haloalkyl group, an ($C_{1-6}$ alkoxy)$C_{1-12}$ alkyl group, an ($C_{1-6}$ alkylthio) $C_{1-12}$ alkyl group, an $C_{1-18}$ alkenyl group, a $C_{3-18}$ haloalkenyl group, an $C_{3-18}$ alkynyl group, a $C_{3-18}$ haloalkynyl group, an $C_{6-10}$ aryl group or a five- to six-membered heteroaryl group {with the proviso that the $C_{6-10}$ aryl group and the five- or six-membered heteroaryl group may have optionally one or more substituents selected from the group consisting of a halogen atom, a cyano group, a nitro group, an amino group, an ($C_{1-6}$ alkyl)amino group, an ($C_{1-6}$ alkyl) ($C_{1-6}$ alkyl) amino group, a pentafluorothio group, an $C_{1-6}$ alkyl group, an $C_{2-6}$ alkenyl group, an $C_{2-6}$ alkynyl group, an $C_{1-6}$ alkoxy group, an $C_{1-6}$ alkylthio group, an $C_{3-6}$ alkenyloxy group, an $C_{3-6}$ alkynyloxy group, an $C_{6-10}$ aryl group, an $C_{6-10}$ aryloxy group, an $C_{1-6}$ alkylsulfinyl group, an $C_{1-6}$ alkylsulfonyl group, a hydroxyl group, an ($C_{1-6}$ alkyl)carbonyl group, a hydroxycarbonyl group, a ($C_{1-6}$ alkoxy) carbonyl group and an ($C_{6-10}$ aryl)$C_{1-6}$ alkoxy group, and when two or more substituents exist, the substituents may be same or different to each other; and the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{1-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the ($C_{1-6}$ alkoxy)carbonyl group and the ($C_{6-10}$ aryl)$C_{1-6}$ alkoxy group may each have one or more halogen atoms or $C_{1-3}$ haloalkyl groups, and when two or more halogen atoms or $C_{1-3}$ haloalkyl groups exist, the halogen atoms or the $C_{1-3}$ haloalkyl groups may be same or different to each other respectively};

when X represents O, $R^4$ represents an $C_{6-10}$ aryl group or a five- to six-membered heteroaryl group {with the proviso that the $C_{6-10}$ aryl group and the five- or six-membered heteroaryl group may have optionally one or more substituents selected from the group consisting of a halogen atom, a cyano group, a nitro group, an amino group, an ($C_{1-6}$ alkyl)amino group, an ($C_{1-6}$ alkyl)($C_{1-6}$ alkyl)amino group, a pentafluorothio group, an $C_{1-6}$ alkyl group, an $C_{2-6}$ alkenyl group, an $C_{2-6}$ alkynyl group, an $C_{1-6}$ alkoxy group, an $C_{1-6}$ alkylthio group, an $C_{3-6}$ alkenyloxy group, an $C_{3-6}$ alkynyloxy group, an $C_{6-10}$ aryl group, an $C_{6-10}$ aryloxy group, an $C_{1-6}$ alkylsulfinyl group, an $C_{1-6}$ alkylsulfonyl group, a hydroxyl group, an ($C_{1-6}$ alkyl)carbonyl group, a hydroxycarbonyl group, a ($C_{1-6}$ alkoxy)carbonyl group and an ($C_{6-10}$ aryl)$C_{1-6}$ alkoxy group, and when two or substituents exist, the substituents may be same or different to each other; and the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the ($C_{1-6}$ alkoxy)carbonyl group and the ($C_{6-10}$ aryl)$C_{1-6}$ alkoxy group may each have one or more halogen atoms or haloalkyl groups, and when two or more halogen atoms or $C_{1-3}$ haloalkyl groups exist, the halogen atoms or the $C_{1-3}$ haloalkyl groups may be same or different to each other respectively};

G represents a hydrogen atom or a group of any one of the following formulae:

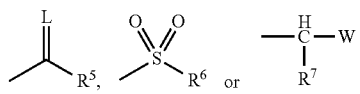

{wherein

L represents an oxygen atom (O) or a sulfur atom (S);

$R^5$ represents an $C_{1-6}$ alkyl group, a $C_{3-8}$ cycloalkyl group, an $C_{2-6}$ alkenyl group, an $C_{2-6}$ alkynyl group, an $C_{6-10}$ aryl group, an ($C_{6-10}$ aryl)$C_{1-6}$ alkyl group, an $C_{1-8}$ alkoxy group, a $C_{3-8}$ cycloalkoxy group, an $C_{3-6}$ alkenyloxy group, an $C_{3-6}$ alkynyloxy group, an $C_{6-10}$ aryloxy group, an ($C_{6-10}$ aryl)$C_{1-6}$ alkoxy group, an ($C_{1-6}$ alkyl)($C_{1-6}$ alkyl)amino group, an ($C_{3-6}$ alkenyl) ($C_{3-6}$ alkenyl)amino group, an ($C_{1-6}$ alkyl) ($C_{6-10}$ aryl)amino group or a five- to six-membered heteroaryl group (with the proviso that these groups may each have one or more halogen atoms, and when two or more halogen atoms exist, the halogen atoms may be same or different to each other; and the $C_{3-8}$ cycloalkyl group, the $C_{6-10}$ aryl group, an aryl moiety of the ($C_{6-10}$ aryl)$C_{1-6}$ alkyl group, the $C_{3-8}$ cycloalkoxy group, the $C_{6-10}$ aryloxy group, an aryl moiety of the ($C_{6-10}$ aryl)$C_{1-6}$ alkoxy group, an aryl moiety of the ($C_{1-6}$ alkyl) ($C_{6-10}$ aryl)amino group and a five- to six-membered heteroaryl group may each have one or more $C_{1-6}$ alkyl groups, and when two or more $C_{1-6}$ alkyl groups exist, the alkyl groups may be same or different to each other);

$R^6$ represents an $C_{1-6}$ alkyl group, an $C_{6-10}$ aryl group or an ($C_{1-6}$ alkyl) ($C_{1-6}$ alkyl)amino group (with the proviso that these groups may each have one or more halogen atoms and when two or more halogen atoms exist, the halogen atoms may be same or different to each other; and the $C_{6-10}$ aryl group may have optionally one or more $C_{1-6}$ alkyl groups and when, two or more $C_{1-6}$ alkyl groups exist, the alkyl groups may be same or different to each other);

$R^7$ represents a hydrogen atom or an $C_{1-6}$ alkyl group;

W represents an $C_{1-6}$ alkoxy group, an $C_{1-6}$ alkylthio group, an $C_{1-6}$ alkylsulfinyl group or an $C_{1-6}$ alkylsulfonyl group (with the proviso that these groups may each have one or more halogen atoms and when two or more halogen atoms exist, the halogen atoms may be same or different to each other)};

Z represents a halogen atom, a cyano group, a nitro group, an $C_{1-6}$ alkyl group, an $C_{2-6}$ alkenyl group, an $C_{2-6}$ alkynyl group, an $C_{1-6}$ alkoxy group, an ($C_{1-6}$ alkyl)carbonyl group, an $C_{1-6}$ alkylthio group, an $C_{6-10}$ aryloxy group, a five- or six-membered heteroaryloxy group, a $C_{3-8}$ cycloalkyl group, an $C_{6-10}$ aryl group or a five- to six-membered heteroaryl group {with the proviso that the $C_{1-6}$ alkyl group, the $C_{2-6}$ alkenyl group, the $C_{2-6}$ alkynyl group, the $C_{1-6}$ alkoxy group, the ($C_{1-6}$ alkyl)carbonyl group and the $C_{1-6}$ alkylthio group may each have one or more halogen atoms, and when two or more halogen atoms exist, the halogen atoms may be same or different to each other; and the $C_{6-10}$ aryl group, the five- to six-membered heteroaryl group, the $C_{6-10}$ aryloxy group and the five- to six-membered heteroaryloxy group may each have one or more substituents selected from the group consisting of a halogen atom, an $C_{1-6}$ alkyl group and a $C_{1-6}$ haloalkyl group, and when two or more substituents exist, the substituents may be same or different to each other; and the $C_{3-8}$ cycloalkyl group may have optionally one or more substituents selected from the group consisting of a halogen atom and an $C_{1-6}$ alkyl group, and when two or more substituents exist, the substituents may be same or different to each other; when n is an integer of 2 or more, Z may be same or different to each other}].

[11] Use of a dihydropyrone compound of formula (I) for controlling weeds, wherein the dihydropyrone compound of formula (I) is a compound represented by a formula:

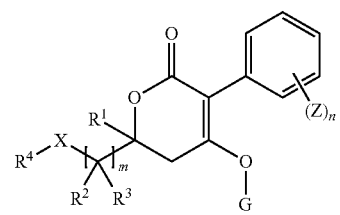

[wherein m is 1, 2 or 3;

n is an integer of any one of 1 to 5;

X represents O, S, S(O) or S(O)$_2$;

$R^1$ represents a hydrogen atom or a methyl group;

$R^2$ and $R^3$ represent independently of each other a hydrogen atom, a halogen atom, an $C_{1-6}$ alkyl group, a $C_{1-6}$ haloalkyl group, a $C_{3-8}$ cycloalkyl group or a $C_{3-8}$ halocycloalkyl group, alternatively $R^2$ and $R^3$ connect each other to represent an $C_{2-5}$ alkylene chain, or $R^2$ and $R^3$ combine each other to represent an $C_{1-3}$ alkylidene group optionally having one or more halogen atoms (with the proviso that when m is 2 or 3, two or three $R^2$ may be same or different to each other and two or three $R^3$ may be same or different to each other);

when X represents S, S(O) or S(O)$_2$, $R^4$ represents a $C_{3-7}$ cycloalkyl group optionally substituted with methyl group or ethyl group, an $C_{1-18}$ alkyl group, a $C_{1-18}$ haloalkyl group, an ($C_{1-6}$ alkoxy) $C_{1-12}$ alkyl group, an ($C_{1-6}$ alkylthio)$C_{1-12}$ alkyl group, an $C_{3-18}$ alkenyl group, a $C_{3-18}$ haloalkenyl group, an $C_{3-18}$ alkynyl group, a $C_{3-18}$ haloalkynyl group, an $C_{6-10}$ aryl group or a five- to six-membered heteroaryl group {with the proviso that the $C_{6-10}$ aryl group and the five- or six-membered heteroaryl group may have optionally one or more substituents selected from the group consisting of a halogen atom, a cyano group, a nitro group, an amino group, an ($C_{1-6}$ alkyl)amino group, an ($C_{1-6}$ alkyl) ($C_{1-6}$ alkyl)amino group, a pentafluorothio group, an $C_{1-6}$ alkyl group, an $C_{2-6}$ alkenyl group, an $C_{2-6}$ alkynyl group, an $C_{1-6}$ alkoxy group, an $C_{1-6}$ alkylthio group, an $C_{3-6}$ alkenyloxy group, an $C_{3-6}$ alkynyloxy group, an $C_{6-10}$ aryl group, an $C_{6-10}$ aryloxy group, an $C_{1-6}$ alkylsulfinyl group, an $C_{1-6}$ alkylsulfonyl group, a hydroxyl group, an ($C_{1-6}$ alkyl)carbonyl group, a hydroxycarbonyl group, a ($C_{1-6}$ alkoxy)carbonyl group and an ($C_{6-10}$ aryl)$C_{1-6}$ alkoxy group, and when two or more substituents exist, the substituents may be same or different to each other; and the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the ($C_{1-6}$ alkoxy) carbonyl group and the ($C_{6-10}$ aryl)$C_{1-6}$ alkoxy group may each have one or more halogen atoms or $C_{1-3}$ haloalkyl groups, and when two or more halogen atoms or $C_{1-3}$ haloalkyl groups exist, the halogen atoms or the $C_{1-3}$ haloalkyl groups may be same or different to each other respectively);

when X represents O, $R^4$ represents an $C_{6-10}$ aryl group or a five- to six-membered heteroaryl group {with the proviso that the $C_{6-10}$ aryl group and the five- or six-membered heteroaryl group may have optionally one or more substituents selected from the group consisting of a halogen atom, a cyano group, a nitro group, an amino group, an ($C_{1-6}$ alkyl)amino group, an ($C_{1-6}$ alkyl) ($C_{1-6}$ alkyl)amino group, a pentafluorothio group, an $C_{1-6}$ alkyl group, an $C_{2-6}$ alkenyl group, an $C_{2-6}$ alkynyl group, an $C_{1-6}$ alkoxy group, an $C_{1-6}$ alkylthio group, an $C_{3-6}$ alkenyloxy group, an $C_{3-6}$ alkynyloxy group, an $C_{6-10}$ aryl group, an $C_{6-10}$ aryloxy group, an $C_{1-6}$ alkylsulfinyl group, an $C_{1-6}$ alkylsulfonyl group, a hydroxyl group, an ($C_{1-6}$ alkyl)carbonyl group, a hydroxycarbonyl group, a ($C_{1-6}$ alkoxy)carbonyl group and an ($C_{6-10}$ aryl)$C_{1-6}$ alkoxy group, and when two or more substituents exist, the substituents may be same or different to each other; and the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the ($C_{1-6}$ alkoxy)carbonyl group and the ($C_{6-10}$ aryl)$C_{1-6}$ alkoxy group may each have one or more halogen atoms or $C_{1-3}$ haloalkyl groups, and when two or more halogen atoms or $C_{1-3}$ haloalkyl groups exist, the halogen atoms or the $C_{1-3}$ haloalkyl groups may be same or different to each other respectively};

G represents a hydrogen atom or a group of any one of the following formulae:

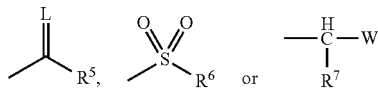

{wherein

L represents an oxygen atom (O) or a sulfur atom (S);

$R^5$ represents an $C_{1-6}$ alkyl group, a $C_{3-8}$ cycloalkyl group, an $C_{2-6}$ alkenyl group, an $C_{2-6}$ alkynyl group, an $C_{6-10}$ aryl group, an ($C_{6-10}$ aryl)$C_{1-6}$ alkyl group, an $C_{1-6}$ alkoxy group, a $C_{3-8}$ cycloalkoxy group, an $C_{3-6}$ alkenyloxy group, an $C_{3-6}$ alkynyloxy group, an $C_{6-10}$ aryloxy group, an ($C_{6-10}$ aryl)$C_{1-6}$ alkoxy group, an ($C_{1-6}$ alkyl) ($C_{1-6}$ alkyl)amino group, an ($C_{3-6}$ alkenyl) ($C_{3-6}$ alkenyl)amino group, an ($C_{1-6}$ alkyl) ($C_{6-10}$ aryl)amino group or a five- to six-membered heteroaryl group (with the proviso that these groups may each have one or more halogen atoms, and when two or more halogen atoms exist, the halogen atoms may be same or different to each other; and the $C_{3-8}$ cycloalkyl group, the $C_{6-10}$ aryl group, an aryl moiety of the ($C_{6-10}$ aryl)$C_{1-6}$ alkyl group, the $C_{3-8}$ cycloalkoxy group, the $C_{6-10}$ aryloxy group, an aryl moiety of the ($C_{6-10}$ aryl)$C_{1-6}$ alkoxy group, an aryl moiety of the ($C_{1-6}$ alkyl) ($C_{6-10}$ aryl)amino group and a five- to six-membered heteroaryl group may each have one or more $C_{1-6}$ alkyl groups, and when two or more $C_{1-6}$ alkyl groups exist, the alkyl groups may be same or different to each other);

$R^6$ represents an $C_{1-6}$ alkyl group, an $C_{6-10}$ aryl group or an ($C_{1-6}$ alkyl)($C_{1-6}$ alkyl)amino group (with the proviso that these groups may each have one or more halogen atoms and when two or more halogen atoms exist, the halogen atoms may be same or different to each other; and the $C_{6-10}$ aryl group may have optionally one or more $C_{1-6}$ alkyl groups and when two or more $C_{1-6}$ alkyl groups exist, the alkyl groups may be same or different to each other);

$R^7$ represents a hydrogen atom or an $C_{1-6}$ alkyl group;

W represents an $C_{1-6}$ alkoxy group, an $C_{1-6}$ alkylthio group, an $C_{1-6}$ alkylsulfinyl group or an $C_{1-6}$ alkylsulfonyl group (with the proviso that these groups may each have one or more halogen atoms and when two or more halogen atoms exist, the halogen atoms may be same or different to each other)};

Z represents a halogen atom, a cyano group, a nitro group, an $C_{1-6}$ alkyl group, an $C_{2-6}$ alkenyl group, an $C_{2-6}$ alkynyl group, an $C_{1-6}$ alkoxy group, an ($C_{1-6}$ alkyl)carbonyl group, an $C_{1-6}$ alkylthio group, an $C_{6-10}$ aryloxy group, a five- or six-membered heteroaryloxy group, a $C_{3-8}$ cycloalkyl group, an $C_{6-10}$ aryl group or a five- to six-membered, heteroaryl group {with the proviso that the $C_{1-6}$ alkyl group, the $C_{2-6}$ alkenyl group, the $C_{2-6}$ alkynyl group, the $C_{1-6}$ alkoxy group, the ($C_{1-6}$ alkyl) carbonyl group and the $C_{1-6}$ alkylthio group may each have one or more halogen atoms, and when two or more halogen atoms exist, the halogen atoms may be same or different to each other; and the $C_{6-10}$ aryl group, the five- to six-membered heteroaryl group, the $C_{6-10}$ aryloxy group and the five- to six-membered heteroaryloxy group may each have one or more substituents selected from the group consisting of a halogen atom, an $C_{1-6}$ alkyl group and a $C_{1-6}$ haloalkyl group, and when two or more substituents exist, the substituents may be same or different to each other; and the $C_{3-8}$ cycloalkyl group may have optionally one or more substituents selected from the group consisting of a halogen atom and an $C_{1-6}$ alkyl group, and when two or more substituents exist, the substituents may be same or different to each other; when n is an integer of 2 or more, Z may be same or different to each other}].

The compound of the present invention shows an efficacy for controlling weeds and is therefore useful as an active ingredient for herbicides.

DESCRIPTION OF EMBODIMENTS

Hereinafter, the present invention is explained in detail.

The substituent of the present invention is explained.

The "$C_{1-18}$ alkyl group" to be used herein means an alkyl group having one to eighteen carbon atoms, and includes, for example, a methyl group, an ethyl group, a normalpropyl group, an isopropyl group, a normalbutyl group, an isobutyl group, a sec-butyl group, a neopentyl group, a normalhexyl group, a normalheptyl group, a normaloctyl group, a normalnonyl group, a normaldecyl group, a normalundecyl group, a normaldodecyl group, a normaltridecyl group, a normaltetradecyl group, a normalpentadecyl group, a normalhexadecyl group, a normaiheptadecyl group and a normaloctadecyl group.

The "$C_{1-6}$ alkyl group" to be used herein means an alkyl group having one to six carbon atoms, and includes, for example, a methyl group, an ethyl group, a normalpropyl group, an isopropyl group, a normalbutyl group, an isobutyl group, a sec-butyl group, a tert-butyl group, a normalpentyl group, a sec-pentyl group, an isopentyl group, a neopentyl group, a normalhexyl group and an isohexyl group.

The "$C_{1-8}$ haloalkyl group" to be used herein means an $C_{1-8}$ alkyl group wherein one or more hydrogen atoms of the alkyl group are substituted with one or more halogen atoms such as a fluorine atom, a chlorine atom, a bromine atom and an iodine atom, and includes, for example, a trifluoromethyl group, a chloromethyl group, a 2,2,2-trichloroethyl group, a 2,2,2-trifluoroethyl group and a 2,2,2-trifluoro-1,1-dichloroethyl group.

The "$C_{1-6}$ haloalkyl group" to be used herein means an $C_{1-6}$ alkyl group wherein one or more hydrogen atoms of the alkyl group are substituted with one or more halogen atoms such as a fluorine atom, a chlorine atom, a bromine atom and an iodine atom, and includes, for example, a trifluoromethyl group, a chloromethyl group, a 2,2,2-trichloroethyl group, a 2,2,2-trifluoroethyl group and a 2,2,2-trifluoro-1,1-dichloroethyl group.

The "$C_{3-8}$ cycloalkyl group" to be used herein means a cycloalkyl group having three to eight carbon atoms and includes, for example, a cyclopropyl group, a cyclopentyl group, a cyclohexyl group and a cycloheptyl group.

The "$C_{3-7}$ cycloalkyl group" to be used herein means a cycloalkyl group having three to seven carbon atoms and includes, for example, a cyclopropyl group, a cyclopentyl group, a cyclohexyl group and a cycloheptyl group.

The "$C_{3-8}$ halocycloalkyl group" to be used herein means a $C_{3-8}$ cycloalkyl group wherein one or more hydrogen atoms of the $C_{3-6}$ cycloalkyl group is/are substituted with one or more halogen atoms such as a fluorine atom, a chlorine atom, a bromine atom and an iodine atom and includes, for example, a 2-chlorocyclopropyl group and a 4,4-difluorocyclohexyl group.

The "($C_{1-6}$ alkoxy)$C_{1-12}$ alkyl group" to be used herein means an $C_{1-12}$ alkyl group wherein one or more hydrogen atoms of the $C_{1-12}$ alkyl group are substituted with an alkoxy group having 1 to 6 carbon atoms and includes, for example, a methoxymethyl group, a 1-methoxyethyl group, an ethoxymethyl group, a butoxymethyl group, an 2-ethoxyethyl group, a 1-methoxypropyl group, a 1-methoxybutyl group, a 1-methoxypentyl group, 1-methoxyhexyl group, a 1-methoxyoctyl group, a 1-methoxydecyl group and a 1-methoxydodecyl group.

The "($C_{1-6}$ alkylthio)$C_{1-12}$ alkyl group" to be used herein means an $C_{1-12}$ alkyl group wherein one or more hydrogen atoms of the $C_{1-12}$ alkyl are substituted with an alkylthio group having 1 to 6 carbon atoms and includes, for example, a methylthiomethyl group, a 1-(methylthio)ethyl group, an ethylthiomethyl group, a butylthiomethyl group, an 2-(ethylthio)ethyl group, a 1-(methylthio)pentyl group, a 1-(methylthio)hexyl group, a 1-(methylthio)octyl group, a 1-(methylthio)decyl group and a 1-(methylthio)dodecyl group.

The "$C_{2-5}$ alkylene chain" to be used herein means an alkylene chain having two to five carbon atoms and includes, for example, an ethylene chain, a propylene chain (i.e., trimethylene chain), a butylene chain (i.e., a tetramethylene chain) and a pentylene chain (i.e., pentamethylene chain).

When $R^2$ and $R^3$ connect each other to represent a $C_{2-5}$ alkylene chain, $R^2$ and $R^3$ combine together with the carbon to which $R^2$ and $R^3$ are attached to form a $C_{3-6}$ cycloalkyl group. For example, when $R^2$ and $R^3$ connect each other to represent an ethylene chain, $R^2$ and $R^3$ combine together with the carbon to which $R^2$ and $R^3$ are attached to form a $C_3$ cycloalkyl group, i.e., a cyclopropyl group.

The "$C_{1-3}$ alkylidene chain" to be used herein means an alkylidene chain having one to three carbon atoms and includes, for example, a methylidene group, an ethylidene group and an isopropylidene group.

The "halogen atom" to be used herein includes, for example, a fluorine atom, a chlorine atom, a bromine atom and an iodine atom.

The "$C_{2-6}$ alkenyl group" to be used herein means an alkenyl group having two to six carbon atoms and includes, for example, a vinyl group, an allyl group, a 1-butene-3-yl group and a 3-butene-1-yl group.

The "$C_{3-18}$ alkenyl group" to be used herein means an alkenyl group having three to eighteen carbon atoms and includes, for example, a 1-buten-3-yl group, a 3-buten-1-yl group, a pentenyl group, a hexenyl group, an octenyl group, a decenyl group, a dodecenyl group, a tetradecenyl group, a hexadecenyl group and an octadecenyl group.

The "$C_{3-6}$ alkenyl group" to be used herein means an alkenyl group having three to six carbon atoms and includes, for example, a 1-butene-3-yl group, a 3-butene-1-yl group, a pentenyl group and a hexenyl group.

The "$C_{3-18}$ haloalkenyl group" to be used herein means an alkenyl group having three to eighteen carbon atoms wherein one or more hydrogen atoms of the alkenyl group are substituted with one or more halogen atoms such as a fluorine atom, a chlorine atom, a bromine atom and an iodine atom and includes, for example, a 1-chloro-propen-2-yl group, a 1-bromo-propen-2-yl group, a 1-chloro-2-propenyl group, a 1-chloro-2-hexenyl group, a 1-chloro-2-octenyl group, a 1-chloro-2-decenyl group, a 1-chloro-2-dodecenyl group, a 1-chloro-2-tetradecenyl group, a 1-chloro-2-hexadecenyl group and a 1-chloro-2-octadecenyl group.

The "$C_{3-6}$ haloalkenyl group" to be used herein means an alkenyl group having three to six carbon atoms wherein one or more hydrogen atoms of the alkenyl group are substituted with one or more halogen atoms such as a fluorine atom, a chlorine atom, a bromine atom and an iodine atom and includes, for example, a 1-chloro-propen-2-yl group, a 1-bromo-propen-2-yl group, 1-chloro-2-pentenyl group and a 1-chloro-2-hexenyl group.

The "$C_{2-6}$ alkynyl group" to be used herein means an alkynyl group having two to six carbon atoms and includes, for example, an ethynyl group, a propargyl group and a 2-butynyl group.

The "$C_{3-18}$ alkynyl group" to be used herein means an alkynyl group having three to eighteen carbon atoms and includes, for example, a propargyl group, a 2-butynyl group, a 2-pentynyl group, a 2-hexynyl group, an 2-octynyl group, a 2-decynyl group, a 2-dodecynyl group, a 2-tetradecynyl group, a 2-hexadecynyl group and an 2-octadecynyl group.

The "$C_{3-6}$ alkynyl group" to be used herein means an alkynyl group having three to six carbon atoms and includes, for example, a propargyl group, a 2-butynyl group, a 2-pentynyl group and a 2-hexynyl group.

The "$C_{3-18}$ haloalkynyl group" to be used herein means an $C_{3-18}$ alkynyl group wherein one or more hydrogen atoms of the alkynyl group are substituted with one or more halogen atoms such as a fluorine atom, a chlorine atom, a bromine atom and an iodine atom and includes, for example, a 1-chloro-2-butynyl group, a 1-chloro-2-pentynyl group, a 1-chloro-2-hexynyl group, a 1-chloro-2-heptynyl group, a 1-chloro-2-octynyl group, a 1-chloro-2-nonynyl group, a 1-chloro-2-decynyl group, a 1-chloro-2-dodecynyl group, a 1-chloro-2-tetradecynyl group, a 1-chloro-2-hexadecynyl group and a 1-chloro-2-octadecynyl group.

The "$C_{3-6}$ haloalkynyl group" to be used herein means an $C_{3-6}$ alkynyl group wherein one or more hydrogen atoms of the alkynyl group are substituted with one or more halogen atoms such as a fluorine atom, a chlorine atom, a bromine atom and an iodine atom and includes, for example, a 1-chloro-2-butynyl group, a 1-chloro-2-pentynyl group and a 1-chloro-2-hexynyl group.

The "$C_{1-6}$ alkoxy group" to be used herein means an alkoxy group having one to six carbon atoms and includes, for example, a methoxy group, an ethoxy group, a normalpropyloxy group, an isopropyloxy group, a normalbutoxy group, an isobutoxy group, a sec-butoxy group, a tert-butoxy group, a normalpentyloxy group, a sec-pentyloxy group, an isopentyloxy group, a neopentyloxy group, a normalhexyloxy group and an isohexyloxy group.

The "$C_{1-6}$ alkylthio group" to be used herein means an alkylthio group having one to six carbon atoms and includes, for example, a methylthio group, an ethylthio group and an isopropylthio group.

The "$C_{1-3}$ alkylthio group" to be used herein means an alkylthio group having one to three carbon atoms and includes, for example, a methylthio group and an ethylthio group.

The "$C_{3-6}$ alkenyloxy group" to be used herein means an alkenyloxy group having three to six carbon atoms and includes, for example, an allyloxy group and a 2-butenyloxy group.

The "$C_{3-6}$ alkynyloxy group" to be used herein means an alkynyloxy group having three to six carbon atoms and includes, for example, a propargyloxy group and a 2-butynyloxy group.

The "($C_{6-10}$ aryl)$C_{1-6}$ alkoxy group" to be used herein means an $C_{1-6}$ alkoxy group wherein one hydrogen atom of the alkoxy group is substituted with an aryl group having six to ten carbon atoms and includes, for example, a benzyloxy group and a phenethyloxy.

The "($C_{6-10}$ aryl)$C_{1-6}$ alkyl group" to be used herein means an $C_{1-6}$ alkyl group wherein one hydrogen atom of the alkyl group is substituted with an aryl group having six to ten carbon atoms and includes, for example, a benzyl group and a phenethyl group.

The "$C_{3-8}$ cycloalkoxy group" to be used herein means a cycloalkoxy group having three to eight carbon atoms and includes, for example, a cyclopropyloxy group, cyclopentyloxy group and a cyclohexyloxy group.

The "($C_{1-6}$ alkyl) ($C_{1-6}$ alkyl)amino group" to be used herein means an amino group wherein two hydrogen atoms of the amino group are substituted with two $C_{1-6}$ alkyl groups that may be same or different to each other and includes, for example, a dimethylamino group, a diethylamino group and an ethylmethylamino group.

The "($C_{3-6}$ alkenyl) ($C_{3-6}$ alkenyl)amino group" to be used herein means an amino group wherein two hydrogen atoms of the amino group are substituted with two $C_{3-6}$ alkenyl groups that may be same or different to each other and includes, for example, a diallylamino group and a di(3-butenyl)amino group.

The "($C_{1-8}$ alkyl) ($C_{6-10}$ aryl)amino group" to be used herein means an amino group wherein two hydrogen atoms of the amino group are substituted with an $C_{1-8}$ alkyl group and a $C_{6-10}$ aryl group and includes for example, a methylphenylamino group and an ethylphenylamino group.

The "$C_{1-8}$ alkylsulfinyl group" to be used herein means an alkylsulfinyl group having one to six carbon atoms and includes, for example, a methylsulfinyl group, an ethylsulfinyl group and an isopropylsulfinyl group.

The "$C_{1-6}$ alkylsulfonyl group" to be used herein means an alkylsulfonyl group having one to six carbon atoms and includes, for example, a methylsulfonyl group, an ethylsulfonyl group and an isopropylsulfonyl group.

The "$C_{6-10}$ aryl group" to be used herein means an aryl group having six to ten carbon atoms and includes, for example, a phenyl group and a naphthyl group.

The "five- to six-membered heteroaryl group" to be used herein means an aromatic five- or six-membered heterocyclic group having 1 to 3 heteroatoms selected from a nitrogen atom, an oxygen atom or a sulfur atom and includes, for example, a 2-pyridyl group, a 4-pyridyl group, a 3-furyl group, a pyrimidinyl group, a 3-thienyl group and a 1-pyrazolyl group.

The "$C_{6-10}$ aryloxy group" to be used herein means an aryloxy group having six to ten carbon atoms and includes, for example, a phenoxy group and a naphthyloxy group.

The "five- to six-membered heteroaryloxy group" to be used herein means an aromatic five- or six-membered heterocyclyloxy group having one to three heteroatoms selected from a nitrogen atom, an oxygen atom or a sulfur atom and includes, for example, a 2-pyridyloxy group and a 3-pyridyloxy group.

The "($C_{1-6}$ alkoxy)carbonyl group" to be used herein means a carbonyl group having an $C_{1-6}$ alkoxy group and includes, for example, a methoxycarbonyl group and an ethoxycarbonyl group.

The "($C_{1-3}$ alkoxy)carbonyl group" to be used herein means a carbonyl group having an $C_{1-3}$ alkoxy group and includes, for example, a methoxycarbonyl group and an ethoxycarbonyl group.

The "($C_{1-6}$ alkyl)amino group" to be used herein means an amino group wherein one hydrogen atom of the amino group is substituted with an $C_{1-6}$ alkyl group and includes, for example, a monomethylamino group and a monoethylamino group.

The "($C_{1-6}$ alkyl)carbonyl group" to be used herein means a carbonyl group having an $C_{1-6}$ alkyl group and includes, for example, a methylcarbonyl group, an ethylcarbonyl group, an isopropylcarbonyl group, a butylcarbonyl group, a pentylcarbonyl group and a hexylcarbonyl group.

The "($C_{1-3}$ alkyl)carbonyl group" to be used herein means a carbonyl group having an alkyl group having one to three carbon atoms and includes, for example, a methylcarbonyl group, an ethylcarbonyl group and an isopropylcarbonyl group.

The "$C_{1-3}$ alkyl group" to be used herein means an alkyl group having one to three carbon atoms and includes, for example, a methyl group, an ethyl group, a normalpropyl group and an isopropyl group.

The "$C_{1-3}$ alkoxy group" to be used herein means an alkoxy group having one to three carbon atoms and includes, for example, methoxy group, an ethoxy group, a normalpropyloxy group and an isopropyloxy group.

The "$C_{1-3}$ haloalkyl group" to be used herein means a $C_{1-3}$ alkyl group wherein one or more hydrogen atoms of the alkyl group are substituted with one or more halogen atoms such as a fluorine atom, a chlorine atom, a bromine atom or an iodine atom and includes, for example, a trifluoromethyl group, a chloromethyl group, a 2,2,2-trichloroethyl group, a 2,2,2-trifluoroethyl group and a 2,2,2-trifluoro-1,1-dichloroethyl group.

The "$C_{1-3}$ haloalkoxy group" to be used herein means an $C_{1-3}$ alkoxy group wherein one or more hydrogen atoms of the alkoxy group are substituted with one or more halogen atoms such as a fluorine atom, a chlorine atom, a bromine atom or an iodine atom and includes, for example, a trifluoromethoxy group, a 2,2,2-trichloroethoxy group, a 3,3-difluoropropyloxy group and a 2,2,2-trifluoroethoxy group.

The "$C_{1-3}$ haloalkylthio group" to be used herein means an $C_{1-3}$ alkylthio group wherein one or more hydrogen atoms of the alkylthio group are substituted with one or more halogen atoms such as a fluorine atom, a chlorine atom, a bromine atom or an iodine atom and includes, for example, a trifluoromethylthio group, a chloromethylthio group, a 2,2,2-trichloroethylthio group, a 2,2,2-trifluoroethylthio group and a 2,2,2-trifluoro-1,1-dichloroethylthio group.

For the present compound, the dihydropyrone compounds of the formula (I) may form agronomically acceptable salts with inorganic bases or organic bases and the present invention may encompass the salt forms of the dihydropyrone compound. The salt includes, for example, salts that are formed by mixing the compound with inorganic bases (for example, hydroxides, carbonates, hydrogen carbonates, acetates or hydrides of alkali metals (for example, lithium, sodium and potassium)), hydroxides or hydrides of alkaline-earth metals (for example, magnesium, calcium and barium) and ammonia), organic bases (for example, dimethylamine, triethylamine, piperazine, pyrrolidine, piperidine, 2-phenylethylamine, benzylamine, ethanolamine, diethanolamine, pyridine and collidine) or metal alkoxides (for example, sodium methoxide, potassium tert-butoxide and magnesium methoxide).

When the present compound has one or more asymmetric centers, two or more stereoisomers (for example, enantiomer and diastereomer) may exist. The present compound may encompass all these stereoisomers and a mixture of two or more arbitrary stereoisomers.

Also when the present compound contains geometric isomers due to a double bond and the like, two or more geometric isomers (for example, each E/Z or trans/cis isomer, each S-trans/S-cis isomer and the others) may exist. The present compound may encompass all these geometric isomers and a mixture of two or more arbitrary geometric isomers.

As an embodiment of the present compound, the following compounds are included for example.
a compound wherein m is 2;
a compound wherein n is 3;
a compound wherein m is 2 and n is 3;
a compound wherein X is S;
a compound wherein $R^2$ is a hydrogen atom;
a compound wherein $R^3$ is a hydrogen atom;
a compound wherein a moiety represented by a formula:

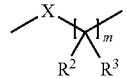

in the formula (I) represents —S—CH$_2$CH$_2$—, —S—CH$_2$CH(CH$_3$)—, —S—CH(CH$_3$)CH$_2$—, —O—CH$_2$CH$_2$—, —S(O)—CH$_2$CH$_2$—, —S(O)—CH$_2$CH (CH$_3$)—, —S(O)$_2$—CH$_2$CH$_2$—, —S(O)$_2$—CH$_2$CH (CH$_3$)—, —S—CH$_2$C(CH$_3$)$_2$—, —S—CH$_2$C(cyclopropyl)-, —S—CH$_2$CH(C$_2$H$_5$)—, —S—CH$_2$— or —S—CH$_2$CH$_2$CH$_2$—;

a compound wherein $R^4$ represents a phenyl group, a 2-pyridyl group, a 3-pyridyl group, a 4-pyridyl group, a 2-pyrimidinyl group, a 2-furyl group, a 2-thienyl group, a 2-thiazolyl group, an 2-oxazolyl group, a 2-(1,3,4-thiadiazolyl) group or a 5-tetrazoly group;

a compound wherein Z is a phenyl group or an $C_{1-6}$ alkyl group optionally having one or more halogen atoms;

a dihydropyrone compound wherein
m is 1, 2 or 3;
n is 1, 2 or 3;
X represents O, S, S(O) or S(O)$_2$;
$R^1$ represents a hydrogen atom;
$R^2$ and $R^3$ represent independently of each other a hydrogen atom or an $C_{1-6}$ alkyl group, alternatively $R^2$ and $R^3$ connect each other to represent an $C_{2-6}$ alkenylene chain;
$R^4$ represents an $C_{6-10}$ aryl group or a five- to six-membered heteroaryl group (with the proviso that the $C_{6-10}$ aryl group and the five- to six-membered heteroaryl group may have optionally one or more substituents selected from the group consisting of a halogen atom, a cyano group, a nitro group, a pentafluorothio group, an $C_{1-6}$ alkyl group and an $C_{1-6}$ alkoxy group, and when two or more substituents exist, the substituents may be same or different to each other; and the $C_{1-6}$ alkyl group and the $C_{1-6}$ alkoxy group may have optionally one or more halogen atoms);
G represents a hydrogen atom or a group of any one of the following formulae:

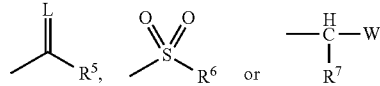

{wherein
L represents an oxygen atom (O);
$R^5$ represents an $C_{1-6}$ alkyl group, an $C_{1-6}$ alkoxy group, an $C_{3-6}$ alkenyloxy group or an $C_{6-10}$ aryloxy group;
$R^6$ represents an $C_{1-6}$ alkyl group;
$R^7$ represents a hydrogen atom;
W represents an $C_{1-6}$ alkoxy group};
Z represents a halogen atom, a phenyl group, an $C_{1-6}$ alkyl group, an $C_{2-6}$ alkenyl group, an $C_{2-6}$ alkynyl group or a six membered heteroaryloxy group (with the proviso that the phenyl group and the six membered heteroaryloxy group may have optionally one or more substituents selected from the group consisting of a halogen atom and a $C_{1-6}$ haloalkyl group, and when two or more substituents exist, the substituent may be same or different to each other).

a dihydropyrone compound wherein
m is 1, 2 or 3;
n is an integer of any one of 1 to 3;
X represents O, S, S(O) or S(O)$_2$;
$R^1$ represents a hydrogen atom;

$R^2$ and $R^3$ represent independently of each other a hydrogen atom or an $C_{1-6}$ alkyl group, alternatively $R^2$ and $R^3$ connect each other to represent an $C_{2-5}$ alkylene chain;

when X represents S, S(O) or S(O)$_2$, $R^4$ represents an $C_{6-10}$ aryl group or a five- to six-membered heteroaryl group (with the proviso that the $C_{6-10}$ aryl group and the five- to six-membered heteroaryl group may have optionally one or more substituents selected from the group consisting of a halogen atom, a pentafluorothio group, an $C_{1-6}$ alkyl group, an $C_{1-6}$ alkoxy group, an $C_{1-6}$ alkylthio group, a hydroxyl group, a ($C_{1-6}$ alkyl)carbonyl group and a ($C_{1-6}$ alkoxy) carbonyl group, and when two or more substituents exist, the substituents may be same or different to each other); or when X represents O, $R^4$ represents an $C_{6-10}$ aryl group {with the proviso that the $C_{6-10}$ aryl group may have optionally one or more $C_{1-6}$ alkyl groups, and when two or more substituents exist, the substituents may be same or different to each other; and the $C_{1-6}$ alkyl group may have one or more halogen atoms, and when two or more halogen atoms exist, the halogen atoms may be same or different to each other};

G represents a hydrogen atom or a group of any one of the following formulae:

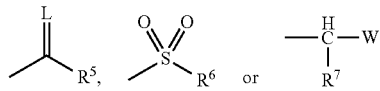

(wherein

L represents an oxygen atom (O);

$R^5$ represents an $C_{1-6}$ alkyl group, an $C_{1-6}$ alkoxy group, an $C_{3-6}$ alkenyloxy group or an $C_{6-10}$ aryloxy group;

$R^6$ represents an $C_{1-6}$ alkyl group;

$R^7$ represents a hydrogen atom;

W represents an $C_{1-6}$ alkoxy group);

Z represents a halogen atom, an $C_{1-6}$ alkyl group, an $C_{2-6}$ alkenyl group, an $C_{2-6}$ alkynyl group, a five- to six-membered heteroaryloxy group or an $C_{6-10}$ aryl group (with the proviso that the $C_{1-6}$ alkyl group, the $C_{2-6}$ alkenyl group and the $C_{2-6}$ alkynyl group may have optionally one or more halogen atoms, and when two or more halogen atoms exist, the halogen atoms may be same or different to each other; the five- to six-membered heteroaryloxy group or the $C_{6-10}$ aryl group may have optionally one or more substituents selected from the group consisting of a halogen atom and a $C_{1-6}$ haloalkyl group, and when two or more substituents exist, the substituents may be same or different to each other).

The herbicide of the present invention comprises the present compound and inert carriers (hereinafter, sometimes referred to as "the present herbicide"). The present herbicide can be usually prepared by further adding auxiliary agents for formulation such as surfactants, stickers, dispersers and stabilizers to formulate into wettable powders, water dispersible granules, flowables, granules, dry flowables, emulsifiable concentrates, aqueous solutions, oil solutions, smoking agents, aerosols, microcapsules and the others. The present herbicide usually contains the present compound in 0.1 to 80% by weight.

The inert carrier includes a solid carrier, a liquid carrier and a gaseous carrier.

Examples of the solid carrier include clays (for example, kaolin, diatomaceous earth, synthetic hydrated silicon dioxide, Fubasami clay, bentonite and acid clay), talcs or the other inorganic minerals (for example, sericite, quartz powder, sulfur powder, activated charcoal, calcium carbonate and hydrated silica) in the form of fine powders or particulates, and examples of the liquid carrier include water, alcohols (for example, methanol and ethanol), ketones (for example, acetone and methyl ethyl ketone), aromatic hydrocarbons (for example, benzene, toluene, xylene, ethylbenzene and methyl naphthalene), aliphatic hydrocarbons (for example, n-hexane, cyclohexane and kerosene), esters (for example, ethyl acetate and butyl acetate), nitriles (for example, acetonitrile and isobutyronitrile), ethers (for example, dioxane and diisopropylether), acid amides (for example, N,N-dimethyl formamide and dimethylacetamide), halogenated hydrocarbons (for example, dichloroethane, trichloroethylene and carbon tetrachloride) and the others.

Examples of the surfactants include alkyl sulfates, alkyl sulfonates, alkyl aryl sulfonates, alkyl aryl ethers and polyoxyethylenated compounds thereof, polyethylene glycol ethers, polyol esters and sugar alcohol derivatives Examples of other auxiliary agents for formulation include stickers and dispersers, specifically casein, gelatin, polysaccharides (for example, starch, gum arabic, cellulose derivatives and alginic acid), lignin derivatives, bentonite, sugars, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof and the others.

The method for controlling weeds of the present invention comprises applying an effective amount of the present compound to weeds or to a soil where weeds grow (hereinafter, sometimes referred as to "the present weeds controlling method"). In the method for controlling weeds of the present invention, the present herbicide is usually used. The method of application comprises, for example, a foliage treatment of the weeds using the present herbicide, a treatment of the soil surface where the weeds grow, and a soil incorporation treatment of the soil where the weeds grow. In the present weeds controlling method, the present compound is applied in amount of usually 1 to 5,000 g and preferably 10 to 1,000 g per 10,000 m$^2$ of area to be controlled weeds.

The present compound can be applied to an agricultural land and the others where "plant" as below-mentioned is cultivated.

"Plant":

Crops:

corn, rice, wheat, barley, rye, oat, *sorghum*, cotton, soybean, peanut, buckwheat, beet, rapeseed, sunflower, sugar cane, tobacco, hop, and the others;

Vegetables:

solanaceous vegetables (for example, eggplant, tomato, pimento, pepper and potato), cucurbitaceous vegetables (for example, cucumber, pumpkin, zucchini, water melon and melon), cruciferous vegetables (for example, Japanese radish, white turnip, horseradish, kohlrabi, Chinese cabbage, cabbage, leaf mustard, broccoli and cauliflower), asteraceous vegetables (for example, burdock, crown daisy, artichoke and lettuce), liliaceous vegetables (for example, green onion, onion, garlic and asparagus), ammiaceous vegetables (for example, carrot, parsley, celery and parsnip), chenopodiaceous vegetables (for example, spinach and Swiss chard), lamiaceous vegetables (for example, *Perilla frutescens*, mint and basil), strawberry, sweet potato, *Dioscorea japonica*, *colocasia* and the others;

Fruits:

pomaceous fruits (for example, apple, pear, Japanese pear, Chinese quince and quince), stone fleshy fruits (for example, peach, plum, nectarine, *Prunus mume*, cherry fruit, apricot and prune), citrus fruits (for example, *Citrus unshiu*, orange, lemon, lime and grapefruit), nuts (for example, chestnut, walnuts, hazelnuts, almond, pistachio, cashew nuts and macadamia nuts), berry fruits (for example, blueberry, cranberry, blackberry and raspberry), grape, kaki persimmon, olive, Japanese plum, banana, coffee, date palm, coconuts, oil palm and the others;

Trees Other than Fruit Trees:

tea, mulberry, flowering plant (for example, dwarf azalea, *camellia*, *hydrangea*, *sasanqua*, *Illicium anisatum*, cherry trees, tulip tree, crape myrtle and fragrant olive), roadside trees (for example, ash, birch, dogwood, *Eucalyptus*, *Ginkgo biloba*, lilac, maple, *Quercus*, poplar, Judas tree, *Liquidambar formosana*, plane tree, *zelkova*, Japanese arborvitae, fir wood, hemlock, juniper, *Pinus*, *Picea*, *Taxus* cuspidate, elm and Japanese horse chestnut), Sweet *viburnum*, *Podocarpus macrophyllus*, Japanese cedar, Japanese cypress, croton, Japanese spindletree and *Photinia glabra*);

Others:

flowers (for example, rose, carnation, *chrysanthemum*, *Eustoma*, *gypsophila*, *gerbera*, marigold, *salvia*, *petunia*, *verbena*, tulip, aster, gentian, lily, pansy, cyclamen, orchid, lily of the valley, lavender, stock, ornamental cabbage, *primula*, poinsettia, *gladiolus*, *cattleya*, daisy, *cymbidium* and *begonia*), bio-fuel plants (for example, *jatropha*, safflower, *Camelina*, switch grass, *Miscanthus giganteus*, *Phalaris arundinacea*, *Arundo donax*, Kenaf (*Hibiscus cannabinus*), cassava (*Manihot esculenta*), willow (Salicaceae), etc.), and ornamental foliage plants, and the others.

The "crops" include genetically modified crops.

The present compound can be mixed or combined with other herbicides, phytotoxicity reducing agents, plant growth regulators, pesticides, miticides, nematicides, fungicides and/or synergists.

Examples of the active ingredient as the herbicides include the followings:

(1) Phenoxy Aliphatic Acid Herbicides 2,4-PA, MCP, MCPB, phenothiol, mecoprop, fluroxypyr, triclopyr, clomeprop, naproanilide and the others;

(2) Benzoic Acid Herbicides 2,3,6-TBA, dicamba, clopyralid, picloram, aminopyralid, quinclorac, quinmerac and the others;

(3) Urea Herbicides diuron, linuron, chlortoluron, isoproturon, Fluometuron, isouron, tebuthiuron, methabenzthiazuron, Cumyluron, daimuron, methyl-daimuron and the others;

(4) Triazine Herbicides atrazine, ametoryn, cyanazine, simazine, propazine, simetryn, dimethametryn, prometryn, metribuzin, triazifam, indaziflam and the others;

(5) Bipyridinium Herbicides paraquat, diquat and the others;

(6) Hydroxybenznitrile Herbicides bromoxynil, ioxynil and the others;

(7) Dinitroaniline Herbicides pendimethalin, prodiamine, trifluralin and the others;

(8) Organophosphorous Herbicides amiprofos-methyl, butamifos, bensulide, piperophos, anilofos, glyphosate, glufosinate, glufosinate-P, bialaphos and the others;

(9) Carbamate Herbicides di-allate, tri-allate, EPTC, butylate, benthiocarb, esprocarb, molinate, dimepiperate, swep, chlorpropham, phenmedipham, phenisopham, pyributicarb, asulam and the others;

(10) Acid Amide Herbicides propanil, propyzamide, bromobutide, etobenzanid and the others;

(11) Chloroacetanilide Herbicides acetochlor, alachlor, butachlor, dimethenamid, propachlor, metazachlor, metolachlor, pretilachlor, thenylchlor, pethoxamid and the others;

(12) Diphenyl Ether Herbicides acifluorfen-sodium, bifenox, oxyfluorfen, lactofen, fomesafen, chlomethoxynil, aclonifen and the others;

(13) Cyclic Imide Herbicide oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, saflufenacil and the others;

(14) Pyrazole Herbicides benzofenap, pyrazolate, pyrazoxyfen, topramezone, pyrasulfotole and the others;

(15) Triketone Herbicides isoxaflutole, benzobicyclon, sulcotrione, mesotrione, tembotrione, tefuryltrione, bicyclopyrone and the others;

(16) Aryloxyphenoxypropionic Acid Herbicides clodinafop-propargyl, cyhalofop-butyl, diclofop-methyl, fenoxaprop-ethyl, fluazifop-butyl, haloxyfop-methyl, quizalofop-ethyl, metamifop and the others;

(17) Trione Oxyme Herbicides alloxydim-sodium, sethoxydim, butroxydim, clethodim, cloproxydim, cycloxydim, tepraloxydim, tralkoxydim, profoxydim and the others;

(18) Sulfonylurea Herbicides chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, propyrisulfuron, metazosulfuron, iofensulfuron-sodium and the others;

(19) Imidazolinone Herbicides imazamethabenz-methyl, imazamox, imazapic, imazapyr, imazaquin, imazethapyr and the others;

(20) Sulfonamide Herbicides flumetsulam, metosulam, diclosulam, florasulam, cloransulam-methyl, penoxsulam, pyroxsulam and the others;

(21) Pyrimidinyloxy Benzoic Acid Herbicides pyrithiobac-sodium, bispyribac-sodium, pyriminobac-methyl, pyribenzoxim, pyriftalid, pyrimisulfan, triafamone and the others; and

(22) Other Systematic Herbicides bentazone, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, methiozolin, fenoxasulfone and the others.

Examples of the active ingredient as the phytotoxicity reducing agents include the followings:

benoxacor, cloquintocet-mexyl, cyometrinil, dichlormid, fenchlorazole-ethyl, fenclorim, flurazole, furilazole, mefenpyr-diethyl, MG191, oxabetrinil, allidochlor, isoxadifenethyl, cyprosulfamide, fluxofenim, 1,8-naphthalic anhydride, AD-67 and the others.

Examples of the active ingredient as the plant growth regulators include the followings:

hymexazol, paclobutrazol, uniconazole-P, inabenfide, prohexadione-calcium, aviglycine, 1-naphthalene acetamide, abscisic acid, indolebutyric acid, ethychlozate, ethephon, cloxyfonac, chlormequat, dichlorprop, gibberellins, prohydrojasmon, benzyladenine, forchlorfenuron, maleic hydrazide, calcium peroxide, mepiquat-chloride, 4-CPA (4-chlorophenoxyacetic acid) and the others.

Examples of the active ingredient as the pesticides include the followings:

(1) Organophosphorous Compound acephate, butathiofos, chlorethoxyfos, chlorfenvinphos, chlorpyrifos, chlorpyrifos-methyl, cyanophos (abbrev: CYAP), diazinon, dichlofenthion (abbrev: ECP), dichlorvos (abbrev: DDVP), dimethoate, dimethylvinphos, disulfoton, EPN, ethion, ethoprophos, etrimfos, fenthion (abbrev: MPP), fenitrothion (abbrev: MEP), fosthiazate, formothion, isofenphos, isoxathion, malathion, mesulfenfos, methidathion (abbrev: DMTP), monocrotophos, naled (abbrev: BRP), oxydeprofos (abbrev: ESP), parathion, phosalone, phosmet (abbrev: PMP), pirimiphos-methyl, pyridafenthion, quinalphos, phenthoate (abbrev: PAP), profenofos, propaphos, prothiofos, pyraclorfos, salithion, sulprofos, tebupirimfos, temephos, tetrachlorvinphos, terbufos, thiometon, trichlorphon (abbrev: DEP), vamidothion, phorate, cadusafos and the others;

(2) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (abbrev: MIPC), metolcarb, methomyl, methiocarb, oxamyl, pirimicarb, propoxur (abbrev: PHC), XMC, thiodicarb, xylylcarb, aldicarb and the others;

(3) Pyrethroid Compounds acrinathrin, allethrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate, protrifenbute and the others;

(4) Nereis Toxin Compounds cartap, bensultap, thiocyclam, monosultap, bisultap;

(5) Neonicotinoid Compounds and the Others;

imidacloprid, nitenpyram, acetamiprid, thiamethoxam, thiacloprid, dinotefuran, clothianidin and the others;

(6) Benzoylurea Compounds chlorfluazuron, bistrifluron, diflubenzuron, fluazuron, flucycloxuron, flufenoxuron, hexaflumuron, lufenuron, novaluron, noviflumuron, teflubenzuron, triflumuron and the others;

(7) Phenylpyrazole Compounds acetoprole, ethiprole, fipronil, vaniliprole, pyriprole, pyrafluprole and the others;

(8) Bt Toxins live spores and crystal toxins originated from *Bacillus thuringiensis* and a mixture thereof;

(9) Hydrazine Compounds chromafenozide, halofenozide, methoxyfenozide, tebufenozide and the others;

(10) Organochlorine Compounds aldrin, dieldrin, chlordane, DDT, dienochlor, endosulfan, methoxychlor and the others; and

(11) Other Pesticide Active Ingredients machine oil, nicotine-sulfate; avermectin-B, bromopropylate, buprofezin, chlorphenapyr, cyromazine, DCIP (dichlorodiisopropyl ether), D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, aluminium phosphide, arsenous oxide, benclothiaz, calcium cyanamide, calcium polysulfide, DSP, flonicamid, flurimfen, formetanate, hydrogen phosphide, metam-ammonium, metam-sodium, methyl bromide, potassium oleate, spiromesifen, Sulfoxaflor, sulfur, metaflumizone, spirotetramat, pyrifluquinazone, spinetoram, chlorantraniliprole, tralopyril, diafenthiuron and the others.

A compound of formula (A):

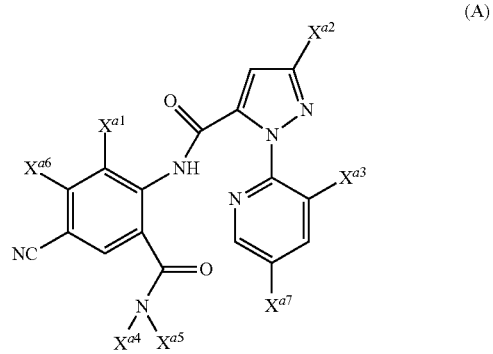

wherein $X^{a1}$ represents a methyl group, a chlorine atom, a bromine atom or a fluorine atom, $X^{a2}$ represents a fluorine atom, a chlorine atom, a bromine atom, a $C_1$-$C_4$ haloalkyl group or a $C_1$-$C_4$ haloalkoxy group, $X^{a3}$ represents a fluorine atom, a chlorine atom or a bromine atom, $X^{a4}$ represents an optionally substituted $C_1$-$C_4$ alkyl group, an optionally substituted $C_3$-$C_4$ alkenyl group, an optionally substituted $C_3$-$C_4$ alkynyl group, an optionally substituted $C_3$-$C_5$ cycloalkylalkyl group or a hydrogen atom, $X^{a5}$ represents a hydrogen atom or a methyl group, $X^{a6}$ represents a hydrogen atom, a fluorine atom or a chlorine atom, and $X^{a7}$ represents a hydrogen atom, a fluorine atom or a chlorine atom.

A compound of formula (B):

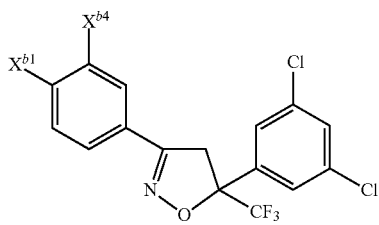

wherein
$X^{b1}$ represents a $X^{b2}$—NH—C(=O) group, a $X^{b2}$—C(=O)—NH—CH$_2$ group, a $X^{b3}$—S(O) group, an optionally substituted pyrrol-1-yl group, an optionally substituted imidazol-1-yl group, an optionally substituted pyrazol-1-yl group or an optionally substituted 1,2,4-triazol-1-yl group, $X^{b2}$ represents an optionally substituted $C_1$-$C_4$ haloalkyl group such as a 2,2,2-trifluoroethyl group or an optionally substituted $C_3$-$C_6$ cycloalkyl group such as a cyclopropyl group, $X^{b3}$ represents an optionally substituted $C_1$-$C_4$ alkyl group such as a methyl group, and $X^{b4}$ represents a hydrogen atom, a chlorine atom, a cyano group or a methyl group.

A compound of formula (C):

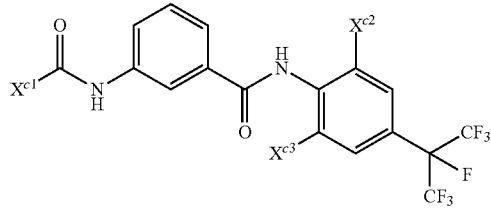

wherein
$X^{c1}$ represents an optionally substituted $C_1$-$C_4$ alkyl group such as a 3,3,3-trifluoropropyl group, an optionally substituted $C_1$-$C_4$ alkoxy group such as a 2,2,2-trichloroethoxy group, an optionally substituted phenyl group such as a 4-cyanophenyl group or an optionally substituted pyridyl group such as a 2-chloro-3-pyridyl group, $X^{c2}$ represents a methyl group or a trifluoromethylthio group, and $X^3$ represents a methyl group or a halogen atom.

Examples of the active ingredient as the miticides include the followings:
acequinocyl, amitraz, benzoximate, bifenazate, bromopropylate, chinomethionat, chlorobenzilate, CPCBS (chlorfenson), clofentezine, cyflumetofen, kelthane (which is also referred to as dicofol), etoxazole, fenbutatin oxide, fenothiocarb, fenpyroximate, fluacrypyrim, halfenprox, hexythiazox, propargite (abbrev: BPPS), polynactins, pyridaben, pyrimidifen, tebufenpyrad, tetradifon, spirodiclofen, spiromesifen, spirotetramat, amidoflumet, cyenopyrafen and the others.

Examples of the active ingredient as the nematicides include the followings:
DCIP, fosthiazate, levamisol, methyisothiocyanate, morantel tartarate, imicyafos and the others.

Examples of the active ingredient as the fungicides include the followings:
(1) Polyhaloalkylthio Compounds
captan, folpet and the others;

(2) Organophosphorous Compounds
IBP, EDDP, tolclofos-methyl and the others;
(3) Benzimidazole Compounds
benomyl, carbendazim, thiophanate-methyl, thiabendazole and the others;
(4) Carboxyamide Compounds
carboxin, mepronil, flutolanil, thifluzamid, furametpyr, boscalid, penthiopyrad and the others;
(5) Dicarboxyimide Compounds
procymidone, iprodione, vinclozolin and the others;
(6) Acylalanine Compounds
metalaxyl and the others;
(7) Azole Compounds
triadimefon, triadimenol, propiconazole, tebuconazole, cyproconazole, epoxiconazole, prothioconazole, ipconazole, triflumizole, prochloraz, penconazole, flusilazole, diniconazole, bromuconazole, difenoconazole, metconazole, tetraconazole, myclobutanil, fenbuconazole, hexaconazole, fluquinconazole, triticonazole, bitertanol, imazalil, flutriafol and the others;
(8) Morpholine Compounds
dodemorph, tridemorph, fenpropimorph and the others;
(9) Strobilurin Compounds
azoxystrobin, kresoxim-methyl, metominostrobin, trifloxystrobin, picoxystrobin, pyraclostrobin, fluoxastrobin, dimoxystrobin and the others;
(10) Antibiotics
validamycin A, blasticidin S, kasugamycin, polyoxin and the others;
(11) Dithiocarbamate Compounds
mancozeb, maneb, thiuram and the others; and
(12) Other Fungicidal Active Ingredients
fthalide, probenazole, isoprothiolane, tricyclazole, pyroquilon, ferimzone, acibenzolar S-methyl, carpropamid, diclocymet, fenoxanil, tiadinil, diclomezine, teclofthalam, pencycuron, oxolinic acid, TPN, triforine, fenpropidin, spiroxamine, fluazinam, iminoctadine, fenpiclonil, fludioxonil, quinoxyfen, fenhexamid, silthiofam, proquinazid, cyflufenamid, bordeaux mixture, dichlofluanid, cyprodinil, pyrimethanil, mepanipyrim, diethofencarb, pyribencarb, famoxadone, fenamidone, zoxamide, ethaboxam, amisulbrom, iprovalicarb, benthiavalicarb, cyazofamid, mandipropamid, metrafenone, fluopiram, bixafen and the others.

Examples of the active ingredient as the synergists include the followings:
piperonyl butoxide, sesamex, sulfoxide, N-(2-ethylhexyl)-8,9,10-trinorborn-5-ene-2,3-dicarboximide (MGK 264), N-declyimidazole), WARF-antiresistan, TBPT, TPP, IBP, PSCP, methyl iodide (CH$_3$I), t-phenylbutenone, diethylmaleate, DMC, FDMC, ETP, ETN and the others.

Examples of the subjects to be controlled by the present herbicide include the followings:
Weeds:
*Digitaria ciliaris, Eleusine indica, Setaria viridis, Setaria faberi, Setaria glauca, Echinochloa crus-galli, Panicum dichotomiflorum, Panicum texanum, Brachiaria platyphylla, Brachiaria plantaginea, Brachiaria decumbens, Sorghum halepense, Andropogon sorghum, Cynodon dactylon, Avena fatua, Lolium multiflorum, Alopecurus myosuroides, Bromus tectorum, Bromus sterilis, Phalaris minor, Apera spica-venti, Poa annua, Agropyron repens, Cyperus iria, Cyperus rotundus, Cyperus esculentus, Portulaca oleracea, Amaranthus retroflexus, Amaranthus hybridus, Amaranthus Amaranthus rudis, Abutilon theophrasti, Sida spinosa, Fallopia convolvulus, Polygonum scabrum, Persicaria pennsylvanica, Persicaria vulgaris, Rumex crispus, Rumex obtusifolius, Fallopia japonica, Chenopodium album, Kochia sco-* paria, Polygonum longisetum, Solanum nigrum, Datura stramonium, Ipomoea purpurea, Ipomoea hederacea, Ipomoea hederacea var. integriuscula, Ipomoea lacunosa, Convolvulus arvensis, Lamium purpureum, Lamium amplexicaule, Xanthium pensylvanicum, Helianthus annuus, Matricaria perforata or inodora, Matricaria chamomilla, Chrysanthemum segetum, Matricaria matricarioides, Ambrosia artemisiifolia, Ambrosia trifida, Erigeron canadensis, Artemisia princeps, Solidago altissima, Conyza bonariensis, Sesbania exaltata, Cassia obtusifolia, Desmodium tortuosum, Trifolium repens, Pueraria lobata, Vicia angustifolia, Commelina communis, Commelina benghalensis, Galium aparine, Stellaria media, Raphanus raphanistrum, Sinapis arvensis, Capsella bursa-pastoris, Veronica persica, Veronica hederifolia, Viola arvensis, Viola tricolor, Papaver rhoeas, Myosotis scorpioides, Asclepias syriaca, Euphorbia helioscopia, Chamaesyce nutans, Geranium carolinianum, Erodium cicutarium, Equisetum arvense, Leersia japonica, Echinochloa oryzicola, Echinochloa crus-galli var. formosensis, Leptochloa chinensis, Cyperus difformis, Fimbristylis miliacea, Eleocharis acicularis, Scirpus juncoides, Scirpus wallichii, Cyperus serotinus, Eleocharis kuroguwai, Bolboschoenus koshevnikovii, Schoenoplectus nipponicus, Monochoria vaginalis, Lindernia procumbens, Dopatrium junceum, Rotala indica, Ammannia multiflora, Elatine triandra, Ludwigia epilobioides, Sagittaria pygmaea, Alisma canaliculatum, Sagittaria trifolia, Potamogeton distinctus, Oenanthe javanica, Callitriche palustris, Lindernia micrantha, Lindernia dubia, Eclipta prostrata, Murdannia keisak, Paspalum distichum, Leersia oryzoides and the others;

Aquatic plants:

Alternanthera philoxeroides, Limnobium spongia, Ceratopteris (Salvinia sp.), Pistia stratiotes, Hydrotyle verticillata (Hydrocotyle sp.), filamentous algae (Pithophora sp., Cladophora sp.), Ceratophyllum demersum, duckweed (Lemna sp.), Cabomba caroliniana, Hydrilla verticillata, Najas guadalupensis, pond weeds (Potamogeton crispus, Potamogeton illinoensis, Potamogeton pectinatus and the like), watermeals (Wolffia sp.), watermillfoils (Myriophyllum spicatum, Myriophyllum heterophyllum and the like), Eichhornia crassipes and the others;

Moss, Liverworts, Hornworts;

Cyanobacterium;

Fern;

Sucher of perennial plants (such as pomaceous fruits, stone fleshy fruits, berry fruits, nuts, citrus fruits, hop and grape).

The present compound can be prepared, for example, according to the below-mentioned process.

Process 1

The present compound of formula (1a) wherein G represents a hydrogen atom can be prepared by heating a compound of formula (2) in the presence or absence of a base.

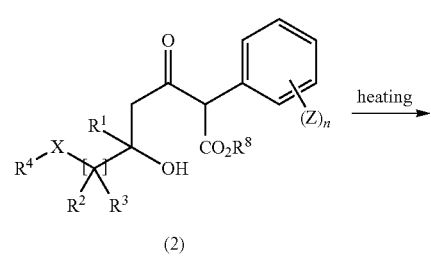

(2)

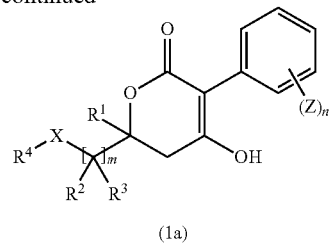

(1a)

[wherein, $R^1$, $R^2$, $R^3$, $R^4$, X, n, m and Z are the same as defined above; $R^8$ represents a methyl group, an ethyl group or an isopropyl group, preferably an isopropyl group]

The reaction is usually carried out in a solvent-free, and can be also carried out in a solvent. Examples of the solvent to be used in the reaction include aromatic hydrocarbons such as benzene, toluene and xylene; amides such as dimethylformamide and dimethylacetamide; and mixed solvents thereof, and preferably include toluene and xylene.

Examples of the base to be used in the reaction includes organic bases such as triethylamine, tripropylamine, pyridine, dimethylaminopyridine and 1,8-diazabicyclo[5.4.0]-7-undecene. The amount used of the base used in the reaction is usually within a range of 1 to 10 molar equivalents and preferably within a range of 2 to 5 molar equivalents as opposed to 1 mole of the compound of formula (2).

The reaction temperature is usually within a range of 100 t 200° C. and preferably within a range of 130 to 180° C.

The reaction period of the reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are acidified with an acid, are mixed with water, and are extracted with an organic solvent, and the resulting organic layers are treated (for example, drying and concentration) to obtain the compound of formula (1a).

Process 2

The present compound of formula (1a) wherein G represents a hydrogen atom can be prepared also by reacting a compound of formula (3) and a compound of formula (4) in the presence of a base.

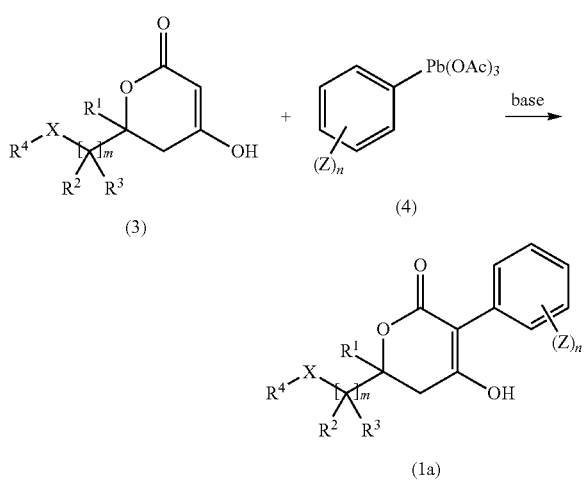

[wherein, $R^1$, $R^2$, $R^3$, $R^4$, X, n, m and Z are the same as defined above]

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof.

Examples of the base to be used in the reaction includes organic bases such as triethylamine, tripropylamine, pyridine, dimethylaminopyridine and 1,8-diazabicyclo[5.4.0]-7-undecene. The amount used of the base used in the reaction is usually within a range of 1 to 10 molar equivalents and preferably within a range of 2 to 5 molar equivalents as opposed to 1 mole of the compound of formula (3).

The reaction temperature is usually within a range of −60 to 180° C. and preferably within a range of −10 to 100° C. The reaction period of the reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are acidified with an acid, are mixed with water, and are extracted with an organic solvent, and the resulting organic layers are treated (for example, drying and concentration) to obtain the compound of the formula (1a).

Process 3

The present compound of formula (1b) wherein G group represents a group other than a hydrogen atom can be prepared by reacting a compound of formula (1a) and a compound of formula (5).

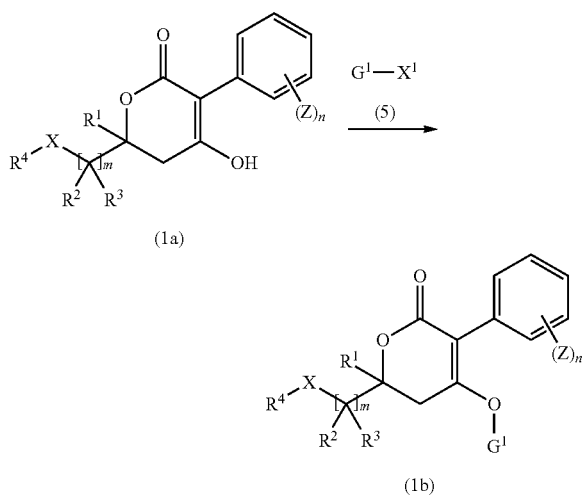

[wherein $G^1$ represents a group of any one of the formulae:

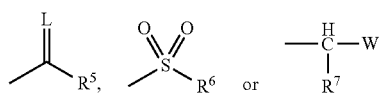

(wherein L, $R^5$, $R^6$, $R^7$ and W are the same as defined above);

$X^1$ represents a halogen atom (for example, a chlorine, atom, a bromine atom, an iodine atom and the like), an $C_{1-3}$ alkylsulfonyloxy group optionally substituted with one or more halogen atoms (for example, a methylsulfonyloxy group, a trifluoromethylsulfonyloxy group) or a group of a formula: $OG^1$ (with the proviso that when $G^1$ represents a group of formula:

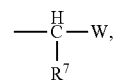

$X^1$ represents a halogen atom or an $C_{1-3}$ alkylsulfonyloxy group optionally substituted with one or more halogen atoms); and $R^1$, $R^2$, $R^3$, $R^4$, X, n, m and Z are the same as defined above] The reaction is usually carried in a solvent.

Examples of the solvent to be used includes aromatic hydrocarbons such as benzene and toluene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfoxides such as dimethyl sulfoxide; sulfones such as sulfolane; and mixed solvents thereof.

Examples of the compound of formula (5) to be used in the reaction include carboxylic halides such as acetylchloride, propionyl chloride, isobutyryl chloride, pivaloyl chloride, benzoyl chloride and cyclohexanecarboxylic acid chloride; carboxylic anhydrides such as acetic anhydride and trifluoroacetic anhydride; halides of carbonate half ester such as methyl chloroformate, ethyl chloroformate and phenyl chloroformate; carbamic halides such as dimethylcarbamoyl chloride; sulfonic halides such as methanesulfonyl chloride and p-toluenesulfohyl chloride; sulfonic anhydrides such as methanesulfonic anhydride and trifluoromethanesulfonic anhydride; alkyl halogenoalkyl ethers such as chloromethyl methyl ether and ethyl chloromethyl ether.

The amount used of the compound of formula (5) used in the reaction is usually within a range of 1 molar equivalent or more and preferably within a range of 1 to 3 molar equivalents as opposed to 1 mole of the compound of formula (1a).

The reaction is usually carried out in the presence of a base. Examples of the base to be used in the reaction include organic bases such as triethylamine, tripropylamine, pyridine, dimethylaminopyridine, 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate and sodium hydride. The amount used of the base is usually within a range of 0.5 to 10 molar equivalents and preferably within a range of 1 to 5 molar equivalents as opposed to 1 mole of the compound of formula (1a).

The reaction temperature is usually within a range of −30 to 180° C. and preferably within a range of −10 to 50° C. The reaction period of the reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are mixed with water and are extracted with an organic solvent, and the resulting organic layers are treated (for example, drying and concentration) to obtain the compound of formula (1b).

The compound of formula (5) is a known compound, or may be prepared from a known compound.

Process 4

The present compound wherein X represents S(O) can be prepared by oxidizing a compound wherein X represents S, that is, a compound of formula (1c). When an alkylthio group or an alkylsulfinyl group is contained at any position other than X in a compound of a formula (1c), these groups may be also oxidized.

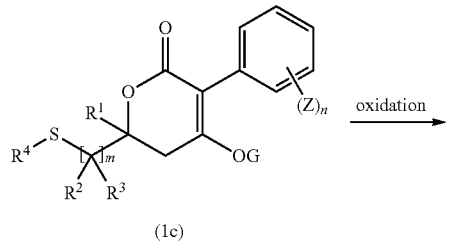

(1c)

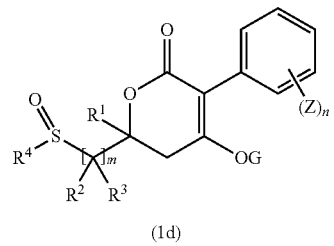

(1d)

layers are treated (for example, drying and concentration) to obtain the compound of formula (1d).

Process 5

The present compound wherein X represents $S(O)_2$ can be prepared by oxidizing a compound of formula (1e) wherein X represents S or S(O). When an alkylthio group, an alkylsulfinyl group, a haloalkylthio group and/or a haloalkylsulfinyl group is/are contained at any position other than X in the compound of formula (1e), these groups may be also oxidized.

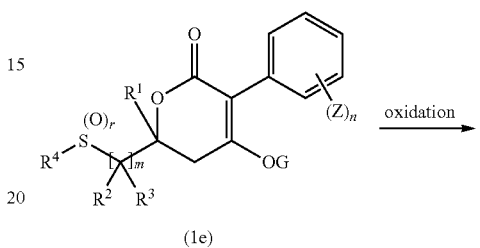

(1e)
r = 0
r = 1

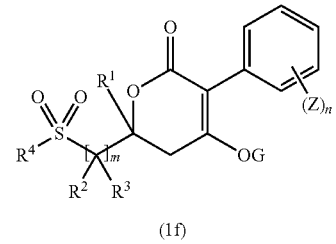

(1f)

[wherein $R^1$, $R^2$, $R^3$, $R^4$, G, n, m and Z are the same as defined above]

An oxidizing agent is used in the reaction. Examples of the oxidizing agent to be used in the reaction includes hydrogen peroxide; peracids such as peracetic acid, perbenzoic acid and m-chloroperbenzoic acid; sodium periodate, ozone, selenium dioxide, chromic acid, dinitrogen tetraoxide, acetyl nitrate, iodine, bromine, N-bromosuccinimide and iodosylbenzene. The oxidizing agent is used usually within a range of 0.8 to 1.2 molar equivalents as opposed to 1 mole of the compound of formula (1c).

The reaction is usually carried out in a solvent. Examples of the solvent to be used in the reaction include saturated hydrocarbons such as hexane, heptane, octane and cyclohexane; aromatic hydrocarbons such as benzene, toluene, xylene, chlorobenzene and dichlorobenzene; halogenated hydrocarbons such as dichloromethane, chloroform, 1,2-dichloroethane and carbon tetrachloride; alcohols such as methanol, ethanol and propanol; nitriles such as acetonitrile; amides such as dimethylformamide and dimethylacetamide; sulfones such as sulfolane; organic acids such as acetic acid and propionic acid; water; and mixed solvents thereof.

The reaction temperature is usually within a range of −50 to 100° C. and preferably within a range of 0 to 50° C.

The reaction period of the reaction is usually within a range of 10 minutes to 10 hours.

The completion of the reaction can be confirmed by analyzing a part of the reaction mixtures on analytical means such as thin-layer chromatography and high-performance liquid chromatography. When the reaction is completed, for example, the reaction mixtures are mixed with water and are extracted with an organic solvent, and the resulting organic

[wherein r is 0 or 1, and $R^1$, $R^2$, $R^3$, $R^4$, G, n, m and Z are the same as defined above]

The reaction is usually carried out in a solvent. Examples of the solvent to be used in the reaction include saturated hydrocarbons such as hexane, heptane, octane and cyclohexane; aromatic hydrocarbons such as benzene, toluene, xylene, chlorobenzene and dichlorobenzene; halogenated hydrocarbons such as dichloromethane, chloroform, 1,2-dichloroethane and carbon tetrachloride; alcohols such as methanol, ethanol and propanol; nitriles such as acetonitrile; amides such as dimethylformamide and dimethylacetamide; sulfones such as sulfolane; organic acids such as acetic acid and propionic acid; water; and mixed solvents thereof.

An oxidizing agent is used in the reaction. Examples of the oxidizing agent include hydrogen peroxide; peracids such as peracetic acid, perbenzoic acid and m-chloroperbenzoic acid; sodium metaperiodate, ozone, selenium dioxide, chromic acid, dinitrogen tetraoxide, acetyl nitrate, iodine, bromine, N-bromosuccinimide, iodosylbenzene, a combination of hydrogen peroxide and tungsten catalyst, a combination of hydrogen peroxide and vanadium catalyst, and potassium permanganate.

When the compound of formula (1e) wherein r is 0 is used, the amount used of the oxidizing agent is usually within a range of 2 to 10 molar equivalents and preferably within a range of 2 to 4 molar equivalents as opposed to 1 mole of the compound of formula (1e). Also when the compound of formula (1e) wherein r is 1 is used, the amount used of the oxidizing agent is usually within a range of 1 to 10 molar equivalents and preferably within a range of 1 to 3 molar equivalents as opposed to 1 mole of the compound of formula (1e).

The reaction temperature is usually within a range of 0 to 200° C. and preferably 20 to 150° C. The reaction period of the reaction is usually within a range of 30 minutes to 10 hours.

The completion of the reaction can be confirmed by analyzing a part of the reaction mixtures on analytical means such as thin-layer chromatography and high-performance liquid chromatography. When the reaction is completed, for example, the reaction mixtures are mixed with water and are extracted with an organic solvent, and the resulting organic layers are treated (for example, drying and concentration) to obtain the compound of formula (1f).

Process 6

The present compound of formula (1g) can be prepared by reacting a compound of formula (21) and a compound of formula (20) in the presence of a base.

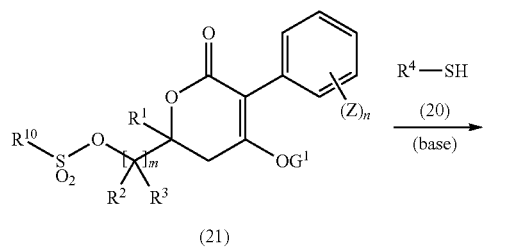

(21)

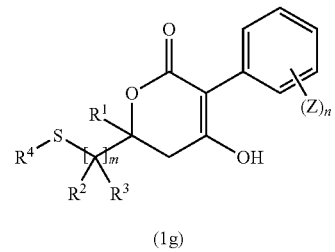

(1g)

[wherein $R^{10}$ represents an $C_{1-6}$ alkyl group or an $C_{6-10}$ aryl group (with the proviso that the $C_{1-6}$ alkyl group and the $C_{6-10}$ aryl group may have optionally one or more halogen atoms, and when two or more halogen atoms exist, the halogen atoms may be same or different to each other; and the $C_{6-10}$ aryl group may have optionally one or more $C_{1-6}$ alkyl groups, and when two or more $C_{1-6}$ alkyl groups exist, the alkyl groups may be same or different to each other; and $R^1$, $R^2$, $R^3$, $R^4$, n, m, Z and $G^1$ are the same as defined above]

The reaction is usually carried out in a solvent. Examples of the solvent to be used in the reaction include ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; and mixed solvents thereof. The amount used of the compound of formula (20) to be used in the reaction is usually within a range of 1 molar equivalent or more and preferably within a range of 1 to 5 molar equivalents as opposed to 1 mole of the compound of formula (21).

Examples of the base to be used in the reaction includes organic bases such as triethylamine, tripropylamine, pyridine, dimethylaminopyridine and 1,8-diazabicyclo[5.4.0]-7-undecene. The amount used of the base is usually within a range of 1 to 10 molar equivalents and preferably within a range of 2 to 5 molar equivalents as opposed to 1 mole of the compound of formula (21).

The reaction temperature is usually within a range of −60 to 180° C. and preferably within a range of −10 to 100° C. The reaction period of the reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, an acid is added to the reaction mixtures, and the reaction mixtures are then mixed with water and are extracted with an organic solvent, and the resulting organic layers are treated (for example, drying and concentration) to obtain the compound of formula (1g).

The compounds that are prepared according to the above-mentioned processes 1 to 5 may be isolated and/or purified by other known means such as concentration, concentration under reduced pressure, extraction, re-extraction, crystallization, recrystallization and chromatography.

Reference Process 1

The present compound of formula (2) can be prepared, for example, by reacting the compound of formula (6) and tetrabutylammonium fluoride (hereinafter, sometimes described as "TBAF") in the presence of a base.

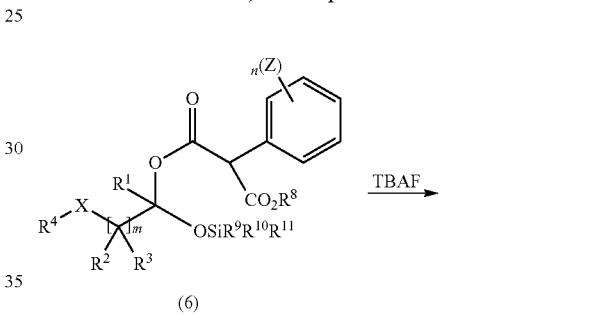

(6)

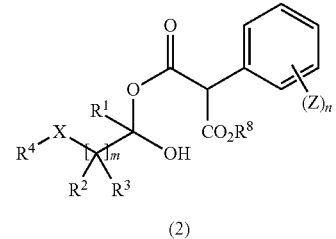

(2)

[wherein, $R^1$, $R^2$, $R^3$, $R^4$, $R^8$, X, Z, n and m are the same as defined above; $R^9$, $R^{10}$ and $R^{11}$ represent a methyl group, an ethyl group, a t-butyl group, an isopropyl group or a phenyl group, preferably a methyl group]

The reaction is usually carried out in a solvent under an inert gas atmosphere. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof.

Examples of the inert gas to be used in the reaction include nitrogen and argon.

The amount used of tetrabutylammonium fluoride used in the reaction is usually within a range of 1 molar equivalent or more and preferably within a range of 1 to 3 molar equivalents as opposed to 1 mole of the compound of formula (6).

Examples of the base to be used in the reaction includes alkaline metal amides such as lithium diisopropylamide, sodium bis(trimethylsilyl)amide, lithium bis(trimethylsilyl)amide and potassium bis(trimethylsilyl)amide; organic bases such as triethylamine, tripropylamine, pyridine, dimethylaminopyridine, 1,8-diazabicyclo[5.4.0]-7-undecene and N,N-diisopropylethylamine; metal alkoxides such as potassium tert-butoxide; and alkali metal hydrides such as sodium hydride, and preferably alkaline metal amides such as lithium diisopropylamide.

The amount used of the base used in the reaction is usually within a range of 1 to 10 molar equivalents and preferably within a range of 1 to 2 molar equivalents as opposed to 1 mole of the compound of formula (6).

The reaction temperature is usually within a range of −80 to 180° C., preferably within a range of −80 to 50° C. and more preferably within a range of −20 to 40° C. The reaction period of the reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are mixed with water, and are extracted with an organic solvent, and the resulting organic layers are treated (for example, drying and concentration) to obtain the compound of formula (2).

Reference Process 2

The compound of formula (6) can be prepared, for example, by reacting the compound of formula (7) and the compound of formula (8) in the presence of a base.

The amount used of the compound of formula (8) to be used in the reation is usually within a range of 1 molar equivalent or more and preferably within a range of 1 to 3 molar equivalents as opposed to 1 mole of the compound of formula (7).

Examples of the base to be used in the reaction includes alkaline metal amides such as lithium diisopropylamide, sodium bis(trimethylsilyl)amide, lithium bis(trimethylsilyl)amide and potassium bis(trimethylsilyl)amide.

The amount used of the base to be used in the reaction is usually within a range of 1 to 10 molar equivalents and preferably within a range of 1 to 2 molar equivalents as opposed to 1 mole of the compound of formula (8).

The reaction temperature is usually within a range of −80 to 180° C. and preferably within a range of −80 to 30° C. The reaction period of the reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are mixed with water, and are extracted with an organic solvent, and the resulting organic layers are treated (for example, drying and concentration) to obtain the compound of formula (6).

The compound of formula (8) is a known compound, or may be prepared from a known compound.

Reference Process 3

The compound of formula (7) can be prepared by, for example, reacting the compound of formula (9) and the compound (A).

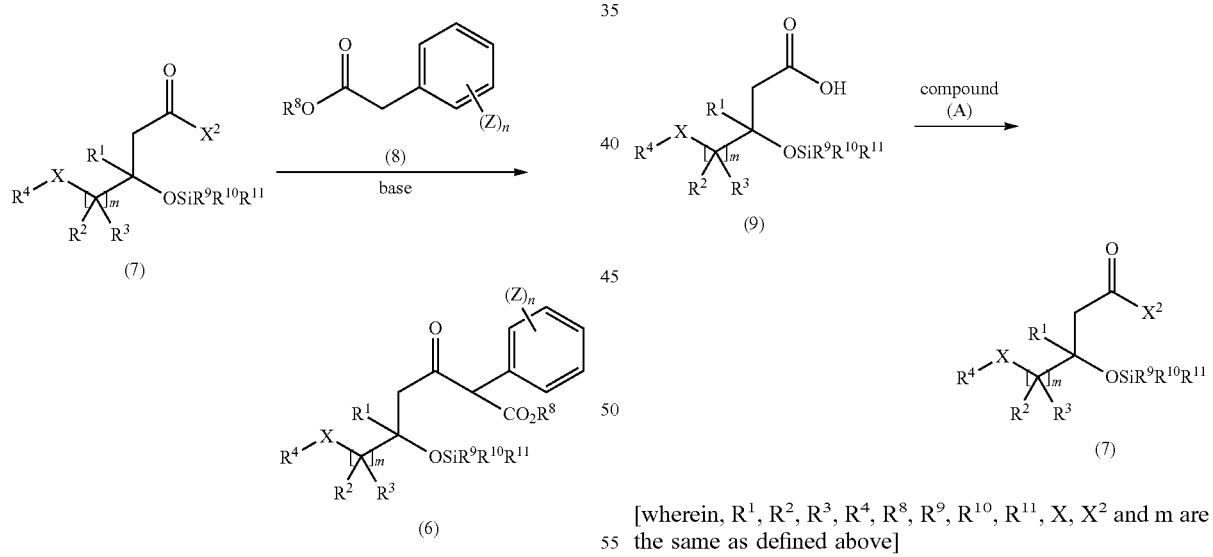

[wherein, $R^1$, $R^2$, $R^3$, $R^4$, $R^8$, $R^9$, $R^{10}$, $R^{11}$, Z, X, n and m are the same as defined above; Also, $X^2$ represents a halogen atom (for example, chlorine atom, a bromine atom or an iodine atom)]

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; and mixed solvents thereof.

[wherein, $R^1$, $R^2$, $R^3$, $R^4$, $R^8$, $R^9$, $R^{10}$, $R^{11}$, X, $X^2$ and m are the same as defined above]

Examples of the compound (A) to be used in the reaction include thionyl chloride, phosphorus tribromide, phosphorus triiodide and 1-chloro-2-methyl-1-propenyl dimethyl amine. Preferable example includes 1-chloro-2-methyl-1-propenyl dimethyl amine.

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide;

sulfones such as sulfolane; and mixed solvents thereof. Preferable example includes halogenated hydrocarbons such as dichloromethane, chloroform and 1,2-dichloroethane.

The amount used of the compound (A) to be used in the reaction is usually within a range of 1 molar equivalent or more and preferably within a range of 1 to 2 molar equivalents as opposed to 1 mole of the compound of formula (9).

The reaction temperature is usually within a range of −30 to 150° C. and preferably within a range of −10 to 30° C. The reaction period of the reaction is usually within a range of 10 minutes to 30 hours.

The completion of the reaction can be confirmed by sampling a part of the reaction mixtures followed by concentrating the reaction mixtures under reduced pressure and performing analytical means such as nuclear magnetic resonance instrument on the resulting organic materials. When the reaction is completed, for example, the reaction solutions are treated (for example, concentration under reduced pressure) to obtain the compound of formula (7).

Reference Process 4

The compound of formula (9) can be prepared by, for example, reacting a compound of formula (10) and a base.

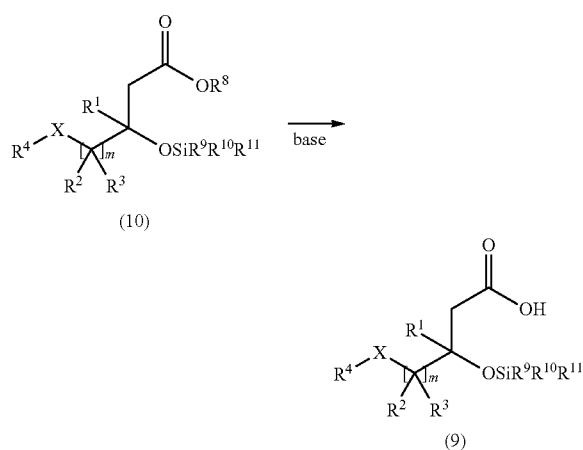

(10)

(9)

[wherein, $R^1$, $R^2$, $R^3$, $R^4$, $R^8$, $R^9$, $R^{10}$, $R^{11}$, X and m are the same as defined above]

The reaction is usually carried out in a solvent. Examples of the solvent to be used in the reaction include ethers such as diethyl ether, diisopropylether, dioxane, tetrahydrofuran and dimethoxyethane; alcohols such as methanol and ethanol; amides such as dimethylformamide and dimethylacetamide; and mixed solvents thereof.

Examples of the base to be used in the reaction include inorganic bases such as lithium hydroxide, sodium hydroxide, potassium hydroxide, sodium methoxide and sodium ethoxide.

The amount used of the base to be used in the reaction is usually within a range of 1 to 10 molar equivalents and preferably within a range of 1 to 5 molar equivalents as opposed to 1 mole of the compound of formula (10).

The reaction temperature is usually within a range of −60 to 180° C. and preferably within a range of −10 to 100° C. The reaction period of the reaction is usually within a range of 10 minutes to 30 hours.

The completion of the reaction can be confirmed by analyzing a part of the reaction mixtures by thin-layer chromatography and high-performance liquid chromatography and the like. When the reaction is completed, for example, to the reaction mixtures is added an acid and the resulting reaction mixture is mixed with water, and is extracted with organic solvent, and the resulting organic layer is treated (for example, drying and concentration) to obtain the compound of formula (9).

Reference Process 5

The compound of formula (10) can be prepared by, for example, reacting a compound of formula (12) and a compound of formula (11) in the presence of a base.

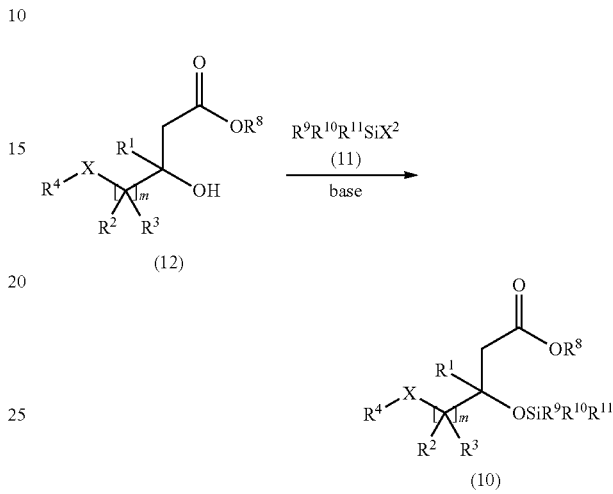

(12)

(10)

[wherein, $R^1$, $R^2$, $R^3$, $R^4$, $R^8$, $R^9$, $R^{10}$, $R^{11}$, X, $X^2$ and m are the same as defined above]

The reaction is usually carried out in a solvent. Examples of the solvent to be used in the reaction include aromatic hydrocarbons such as benzene and toluene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof.

Examples of the compound of formula (11) to be used in the reaction include chlorotrimethylsilane and tert-butyldimethylchlorosilane.

The amount used of the compound of formula (11) to be used in the reaction is usually within a range of 1 molar equivalent or more and preferably within a range of 1 to 3 molar equivalents as opposed to 1 mole of the compound of formula (12).

Examples of the base to be used in the reaction includes alkaline metal amides such as lithium diisopropylamide, sodium bis(trimethylsilyl)amide, lithium bis(trimethylsilyl) amide and potassium bis(trimethylsilyl)amide; organic bases such as triethylamine, tripropylamine, pyridine, dimethylaminopyridine, 1,8-diazabicyclo[5.4.0]-7-undecene, N,N-diisopropylethylamine and imidazole; metal alkoxides such as potassium tert-butoxide; and alkali metal hydrides such as sodium hydride, and preferably organic bases such as imidazole.

The amount used of the base to be used in the reaction is usually within a range of to 1 to 10 molar equivalents and preferably within a range of 1 to 2 molar equivalents as opposed to 1 mole of the compound of formula (12).

The reaction temperature is usually within a range of −80 to 180° C. and preferably within a range of −10 to 100° C. The reaction period of this reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are mixed with water, and are extracted with an organic solvent, and the resulting organic layers are treated (for example, drying and concentration) to obtain the compound of formula (10).

Reference Process 6

The compound of formula (12) can be prepared by, for example, reacting a compound of formula (13) and a base, followed by reacting with a compound of formula (14).

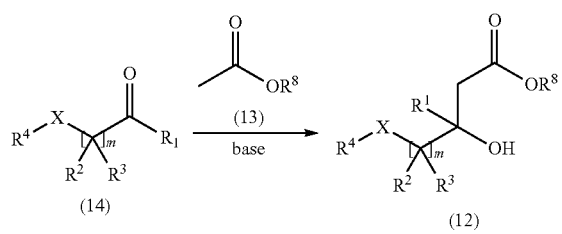

[wherein, $R^1$, $R^2$, $R^3$, $R^4$, $R^8$, X and m are the same as defined above]

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof.

Examples of the compound of formula (13) to be used in the reaction include methyl acetate, ethyl acetate and isopropyl acetate.

The amount used of the compound of formula (13) to be used in the reaction is usually within a range of 1 molar equivalent or more and preferably within a range of 1 to 3 molar equivalents as opposed to 1 mole of the compound of formula (14).

Examples of the base to be used in the reaction includes alkaline metal amides such as lithium diisopropylamide, sodium bis(trimethylsilyl)amide, lithium bis(trimethylsilyl) amide and potassium bis(trimethylsilyl)amide; organic bases such as triethylamine, tripropylamine, pyridine, dimethylaminopyridine, 1,8-diazabicyclo[5.4.0]-7-undecene and N,N-diisopropylethylamine; metal alkoxides such as potassium tert-butoxide; and alkali metal hydrides such as sodium hydride, and preferably alkaline metal amides such as lithium diisopropylamide.

The amount used of the base to be used in the reaction is usually within a range of to 1 to 10 molar equivalents and preferably within a range of 1 to 2 molar equivalents as opposed to 1 mole of the compound of formula (13).

The reaction temperature is usually within a range of −80 to 180° C. and preferably within a range of −80 to 50° C. The reaction period of this reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are mixed with water, and are extracted with an organic solvent, and the resulting organic layers are treated (for example, drying and concentration) to obtain the compound of formula (12).

The compound of formula (13) is a known compound, or may be prepared from a known compound.

Reference Process 7

The compound of formula (3) can be prepared by, for example, reacting a compound of formula (15) in the presence of an acid.

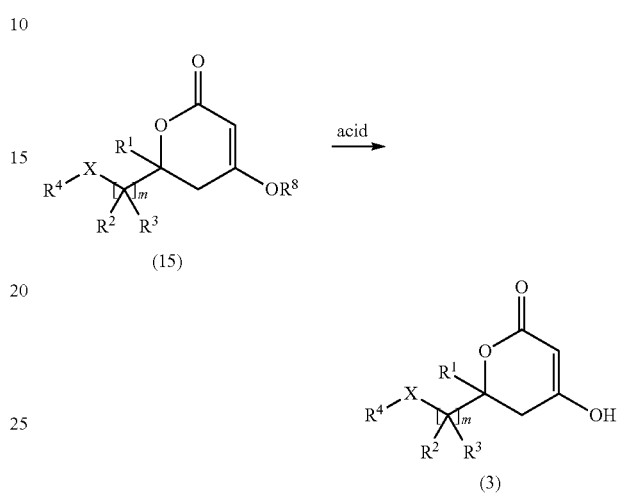

[wherein, $R^1$, $R^2$, $R^3$, $R^4$, $R^8$, X and m are the same as defined above] The reaction is usually carried out in a solvent.

Examples of the solvent to be used in the reaction include ethers such as diethyl ether, diisopropylether, dioxane, tetrahydrofuran and dimethoxyethane; alcohols such as methanol and ethanol; amides such as dimethylformamide and dimethylacetamide; and mixed solvents thereof.

Examples of the acid to be used in the reaction include hydrochloric acid and boron tribromide. The amount used of the acid to be used in the reaction is usually within a range of 1 to 10 molar equivalents as opposed to 1 mole of the compound of formula (15).

The reaction temperature is usually within a range of −80 to 180° C. and preferably within a range of −80 to 50° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, an acid is added to the reaction mixture and the resulting reaction mixture is mixed with water, and is extracted with an organic solvent, and the resulting organic layer is treated (for example, drying and concentration) to obtain the compound of formula (3).

Reference Process 8

The compound of formula (15) can be prepared by, for example, reacting a compound of formula (16) in the presence of a base.

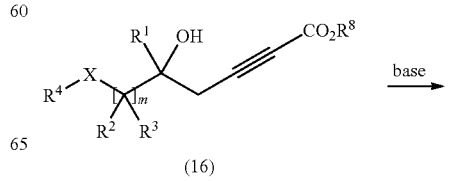

-continued

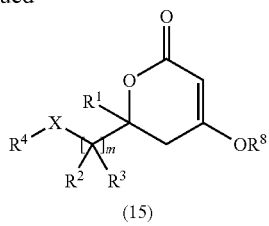

(15)

[wherein, $R^1$, $R^2$, $R^3$, $R^4$, $R^8$, X and m are the same as defined above] The reaction is usually carried out in a solvent.

Examples of the solvent to be used in the reaction include ethers such as diethyl ether, diisopropylether, dioxane, tetrahydrofuran and dimethoxyethane; alcohols such as methanol and ethanol; amides such as dimethylformamide and dimethylacetamide; and mixed solvents thereof, and preferably alcohols such as methanol and ethanol.

Examples of the base to be used in the reaction include metal alkoxides such as sodium methoxide.

The amount used of the base to be used in the reaction is usually within a range of 1 to 10 molar equivalents as opposed to 1 mole of the compound of formula (16).

The reaction temperature is usually within a range of −80 to 180° C. and preferably within a range of −80 to 50° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, an acid is added to the reaction mixture and the resulting reaction mixture is mixed with water and are extracted with an organic solvent, and the resulting organic layers are treated (for example, drying and concentration) to obtain the compound of formula (15).

Reference Process 9

The compound of formula (16) can be prepared by, for example, reacting a compound of formula (18) and a compound of formula (17) in the presence of a base and a Lewis acid.

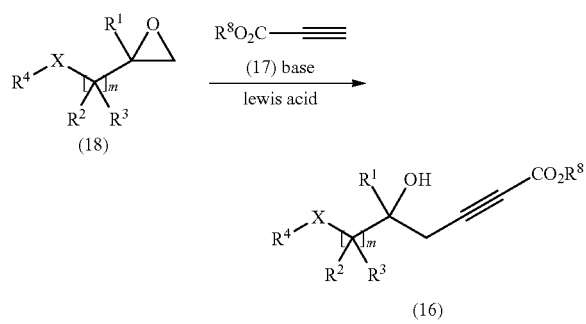

[wherein, $R^1$, $R^2$, $R^3$, $R^4$, $R^8$, X and m are the same as defined above]

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof.

Examples of the compound of formula (17) to be used in the reaction include methyl propionate and ethyl propionate.

The amount used of the compound of formula (17) to be used in the reaction is usually within a range of 1 molar equivalent or more and preferably within a range of 1 to 3 molar equivalents as opposed to 1 mole of the compound of formula (18).

Examples of the base to be used in the reaction includes organic lithiums such as n-butyl lithium, phenyl lithium and methyl lithium; alkaline metal amides such as lithium diisopropylamide, sodium bis(trimethylsilyl)amide, lithium bis (trimethylsilyl)amide and potassium bis(trimethylsilyl)amide; organic bases such as triethylamine, tripropylamine, pyridine, dimethylaminopyridine, 1,8-diazabicyclo[5.4.0]-7-undecene and N,N-diisopropylethylamine; metal alkoxides such as potassium tert-butoxide; and alkali metal hydrides such as sodium hydride.

The amount used of the base to be used in the reaction is usually within a range of 1 to 10 molar equivalents and preferably within a range of 1 to 2 molar equivalents as opposed to 1 mole of the compound of formula (17).

Examples of the Lewis acid to be used in the reaction include boron trifluoride. The amount used of the Lewis acid to be used in the reaction is usually within a range of 1 to 10 molar equivalents and preferably within a range of 1 to 5 molar equivalents as opposed to 1 mole of the compound of formula (18).

The reaction temperature is usually within a range of −80 to 180° C. and preferably within a range of −80 to 50° C. The reaction period of this reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixture is mixed with water, and is extracted with an organic solvent, and the resulting organic layer is treated (for example, drying and concentration) to obtain the compound of formula (16).

The compound of formula (17) is a known compound, or may be prepared from a known compound.

The compound of formula (18) can be prepared according to a method described in Journal of Organic Chemistry (2009), vol. 74, p. 9509-9512, Journal of Organic Chemistry (2008), vol. 73, p. 9479-9481 or Canadian Journal of Chemistry (1981) vol. 59, p. 1415 to 1424, or the similar methods thereto.

Reference Process 10

A compound of formula (4) can be prepared by, for example, reaction a compound of formula (19) with zinc tetraacetate in the presence of a base according to Marie-Luise Huber and John T. Pinhey, Journal of Chemical Society Perkin Transion 1 (1990), p. 721.

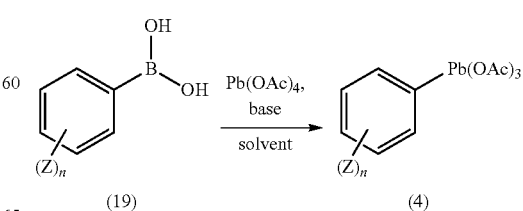

[wherein Z and n are the same as defined above]

The compound of formula (19) is a known compound, or may be prepared from a known compound. For example, the compound of formula (19) can be prepared according to a method described in JP 2008-133252 A or a similar method thereto.

Reference Process 11

The compound of formula (21) can be prepared by reacting a compound of formula (23) and a compound of a formula (22).

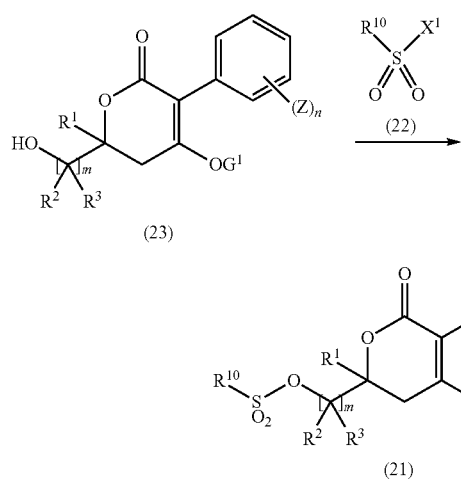

[wherein, $R^{10}$, $X^1$, $R^1$, $R^2$, $R^3$, n, m, $G^1$ and Z are the same as defined above]

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfoxides such as dimethyl sulfoxide; sulfones such as sulfolane; and mixed solvents thereof.

Examples of the compound of formula (22) to be used in the reaction include sulfonic halides such as methanesulfonyl chloride and p-toluenesulfonyl chloride; sulfonic anhydrides such as methanesulfonic anhydride and trifluoromethanesulfonic anhydride. The amount used of the compound of formula (22) to be used in the reaction is usually within a range of 1 molar equivalent or more and preferably within a range of 1 to 3 molar equivalents as opposed to 1 mole of the compound of formula (23).

The reaction is usually carried out in the presence of a base. Examples of the base to be used in the reaction include organic bases such as triethylamine, tripropylamine, pyridine, dimethylaminopyridine, 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate and sodium hydride. The amount used of the base to be used in the reaction is usually within a range of 0.5 to 10 molar equivalents and preferably within a range of 1 to 5 molar equivalents as opposed to 1 mole of the compound of formula (23).

The reaction temperature is usually within a range of −30 to 180° C. and preferably within a range of −10 to 50° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, the reaction mixtures are mixed with water and are extracted with an organic solvent, and the resulting organic layers are treated (for example, drying and concentration) to obtain the compound of formula (21).

The compound of formula (22) is a known compound, or may be prepared from a known compound.

Reference Process 12

The compound of formula (23) can be prepared, for example, by reacting a compound of formula (24) in the presence of a metal.

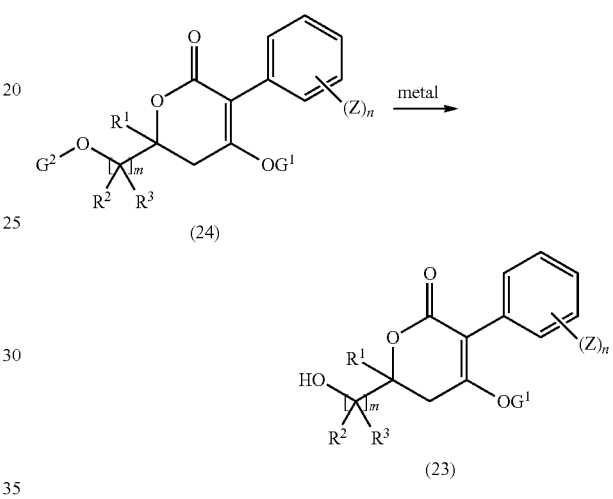

[wherein, $G^2$ represents a benzyl group or a para-methoxybenzyl group; and $R^1$, $R^2$, $R^3$, n, m, $G^1$ and Z are the same as defined above]

The reaction is usually carried out in a solvent. Examples of the solvent to be used in the reaction include aromatic hydrocarbons such as benzene and toluene; ethers such as diethyl ether, diisopropylether, dioxane, tetrahydrofuran and dimethoxyethane; alcohols such as methanol and ethanol; esters such as ethyl acetate; and mixed solvents thereof.

Examples of the metal to be used in the reaction include palladium and platinum. The amount used of the metal to be used in the reaction is usually within a range of 0.01 molar equivalents or more and preferably within a range of 0.01 to 0.5 molar equivalents as opposed to 1 mole of the compound of formula (24).

The reaction temperature is usually within a range of −30 to 180° C. and preferably within a range of −10 to 50° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, the reaction mixtures are filtered through Celite (registered trademark) and the resulting filtrates are treated (for example, concentration under reduced pressure) to obtain the compound of formula (23).

Reference Process 13

The compound of formula (24) can be prepared by reacting a compound of formula (26) and a compound of formula: $G^1$-$X^1$ in the presence of a base.

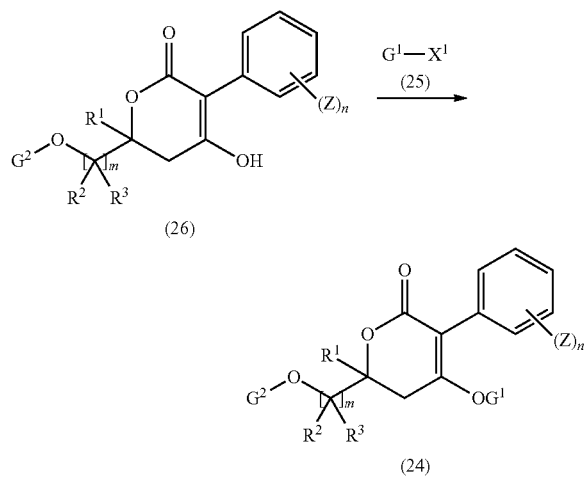

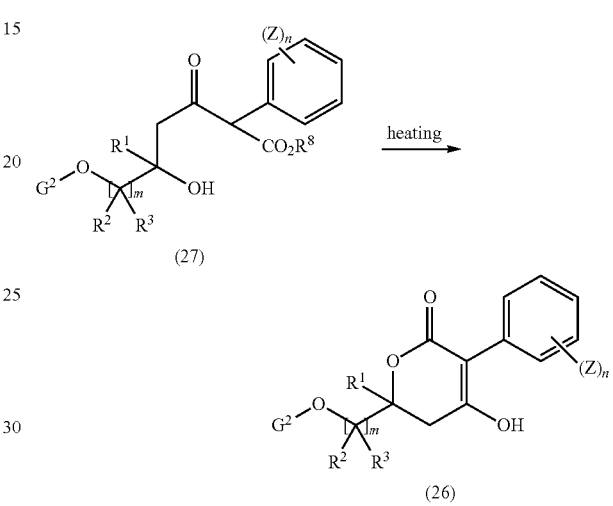

[wherein, $R^1$, $R^2$, $R^3$, $X^1$, n, m, Z, $G^2$ and $G^1$ are the same as defined above]

The reaction is usually carried out in a solvent. Examples of the solvent to be used in the reaction include aromatic hydrocarbons such as benzene and toluene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfoxides such as dimethyl sulfoxide; sulfones such as sulfolane; and mixed solvents thereof.

Examples of the compound of formula: $G^1$-$X^1$ to be used in the reaction include carboxylic halides such as acetyl chloride, propionyl chloride, isobutyryl chloride, pivaloyl chloride, benzoyl chloride and cyclohexanecarboxylic acid chloride; carboxylic anhydrides such as acetic anhydride and trifluoroacetic anhydride; halides of carbonate ester such as methyl chloroformate, ethyl chloroformate and phenyl chloroformate; carbamic halides such as dimethylcarbamoyl chloride; sulfonic halides such as methanesulfonyl chloride and p-toluenesulfonyl chloride; sulfonic anhydrides such as methanesulfonic anhydride and trifluoromethanesulfonic anhydride; alkyl halogenoalkyl ethers such as chloromethyl methyl ether and ethyl chloromethyl ether.

The amount used of the compound of formula: $G^1$-$X^1$ to be used in the reaction is usually within a range of 1 molar equivalent or more and preferably within a range of 1 to 3 molar equivalents as opposed to 1 mole of the compound of formula (26).

Examples of the base to be used in the reaction includes organic bases such as triethylamine, tripropylamine, pyridine, dimethylaminopyridine, 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate and sodium hydride.

The amount used of the base to be used in the reaction is usually within a range of 0.5 to 10 molar equivalents and preferably within a range of 1 to 5 molar equivalents as opposed to 1 mole of the compound of formula (26).

The reaction temperature is usually within a range of −30 to 180° C. and preferably within a range of −10 to 50° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, the reaction mixtures are mixed with water, and are extracted with an organic solvent, and the resulting organic layers are treated (for example, drying and concentration) to obtain the compound of formula (24).

The compound of formula: $G^1$-$X^1$ is a known compound, or may be prepared from a known compound.

Reference Process 14

The compound of formula (26) can be prepared by heating a compound of formula (27) in the presence or absence of a base.

[wherein, $R^1$, $R^2$, $R^3$, $R^8$, n, m, Z and $G^2$ are the same as defined above]

The reaction is usually carried out in a solvent-free, and can be also carried out in a solvent. Examples of the solvent to be used in the reaction include aromatic hydrocarbons such as benzene, toluene and xylene; amides such as dimethylformamide and dimethylacetamide; and mixed solvents thereof, and preferably include toluene and xylene.

Examples of the base to be used in the reaction includes organic bases such as triethylamine, tripropylamine, pyridine, dimethylaminopyridine and 1,8-diazabicyclo[5.4.0]-7-undecene. The amount used of the base to be used in the reaction is usually within a range of 1 to 10 molar equivalents and preferably within a range of 2 to 5 molar equivalents as opposed to 1 mole of the compound of formula (27).

The reaction temperature is usually within a range of 100 to 200° C. and preferably within a range of 130 to 180° C. The reaction period of the reaction is usually within a range of 10 minutes to 30 hours.

The completion of the reaction can be confirmed by sampling a part the reaction mixtures followed by performing analytical means such as thin-layer chromatography and high-performance liquid chromatography. When the reaction is completed, for example, the reaction mixtures are acidified with an acid, are mixed with water, and are extracted with an organic solvent, and the resulting organic layers are treated (for example, drying and concentration) to obtain the compound of formula (1a).

Reference Process 15

The compound of formula (27) can be prepared by, for example, reacting a compound of formula (29) and a compound of formula (28) in the presence of two molar equivalents of a base.

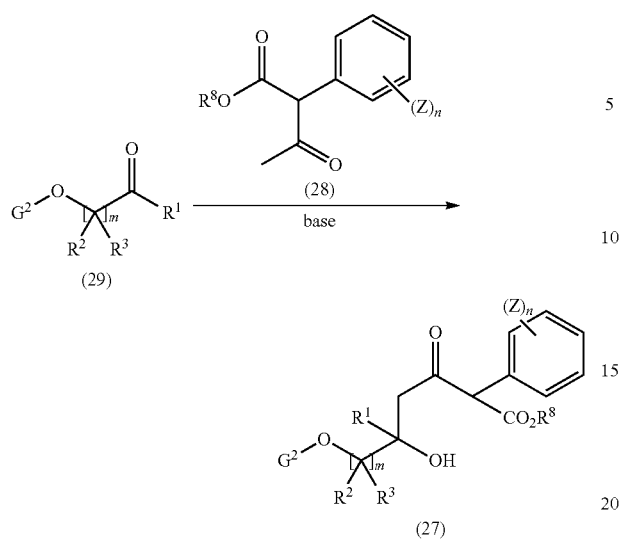

[wherein, $R^1$, $R^2$, $R^3$, $R^4$, $R^8$, Z, n, m and $G^2$ are the same as defined above]

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; and mixed solvents thereof.

The amount used of the compound of formula (28) to be used in the reaction is usually within a range of 1 molar equivalent or more and preferably within a range of 1 to 3 molar equivalents as opposed to 1 mole of the compound of formula (29).

Examples of the base to be used in the reaction includes alkaline metal amides such as lithium diisopropylamide, sodium bis(trimethylsilyl)amide, lithium bis(trimethylsilyl) amide and potassium bis(trimethylsilyl)amide; and inorganic bases such as sodium hydroxide, potassium hydroxide, calcium hydroxide, sodium carbonate, potassium carbonate, sodium hydrogen carbonate, calcium carbonate, sodium hydride and potassium hydride.

The amount used of the base to be used in the reaction is usually within a range of to 2 to 10 molar equivalents and is preferably 2 molar equivalents, as opposed to 1 mole of the compound of formula (29).

The reaction temperature is usually within a range of –80 to 180° C. and preferably within a range of –40 to 30° C. The reaction period of this reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are mixed with water, and are extracted with an organic solvent, and the resulting organic layers are treated (for example, drying and concentration) to obtain the compound of formula (27).

The compound of formula (28) can be prepared, for example, according to a method described in WO 2007/144625.

Some examples of the present compounds that can be prepared according to the above-mentioned processes are shown below. Hereinafter, the compound of formula (a-b) means the present compound (a-b).

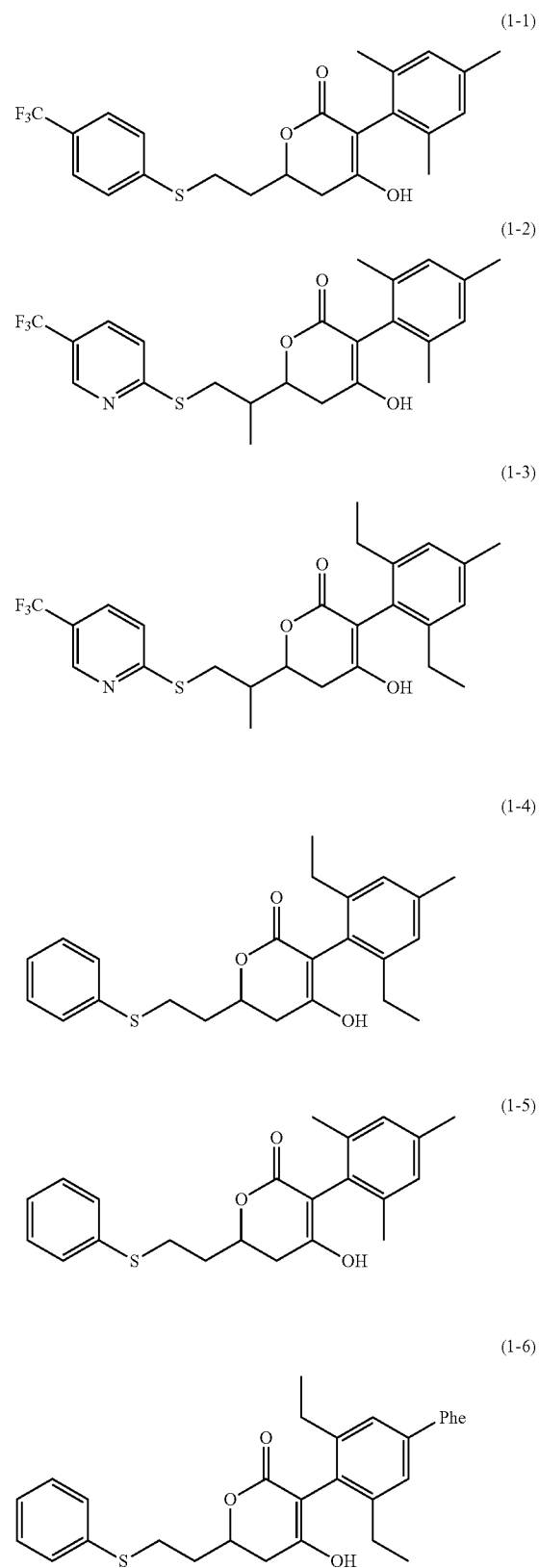

(1-7)
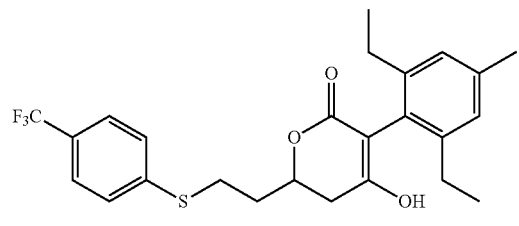
(1-8)
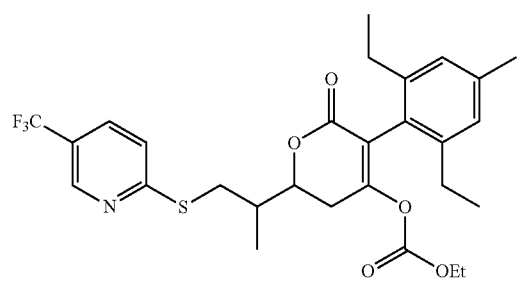
(1-9)
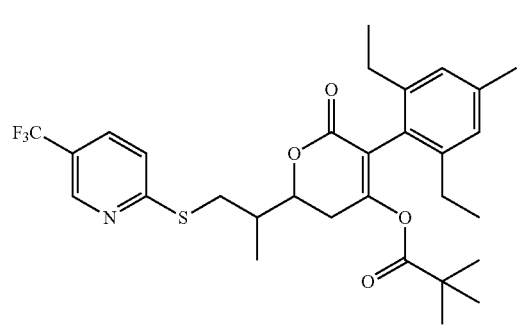
(1-10)
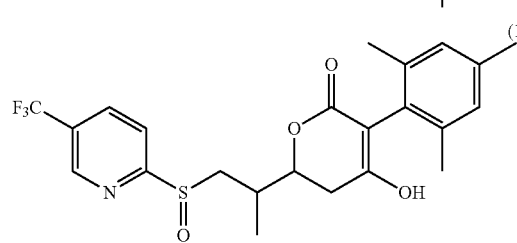
(1-11)
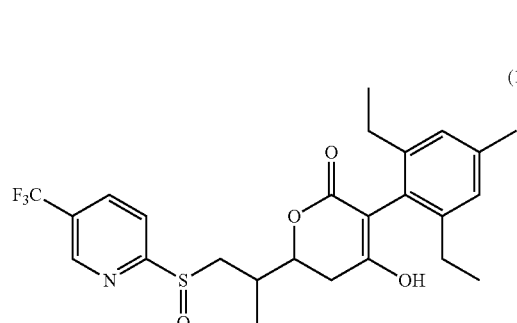
(1-12)
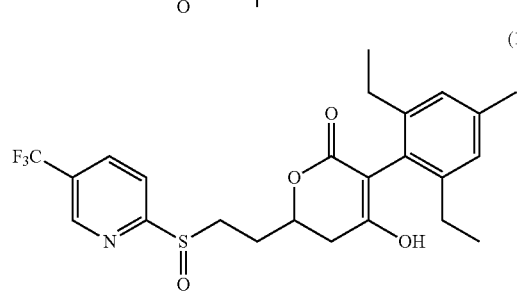
(1-13)
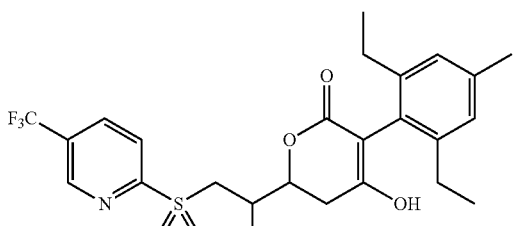
(1-14)
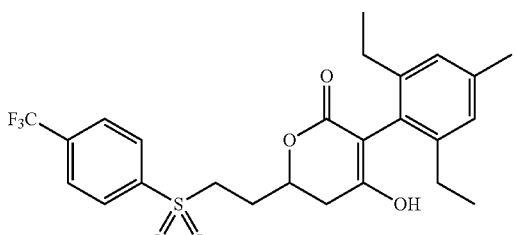
(1-15)
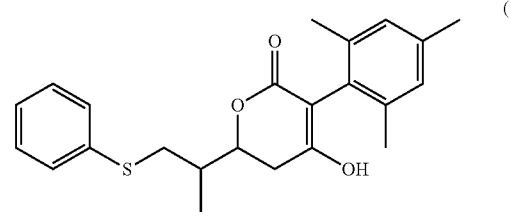
(1-16)
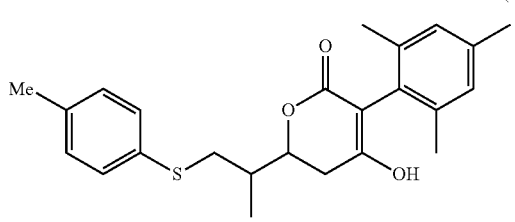
(1-17)
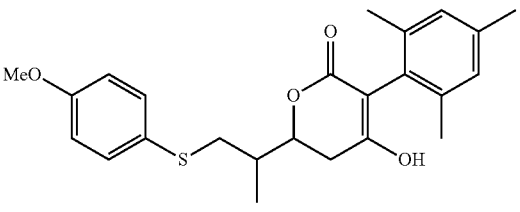
(1-18)
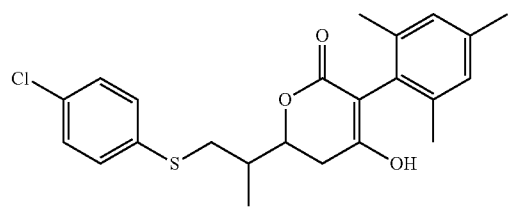

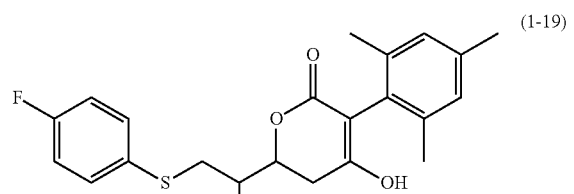
(1-19)
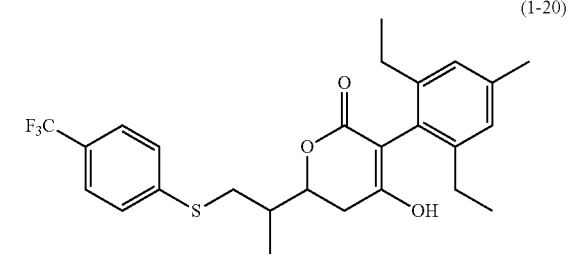
(1-20)
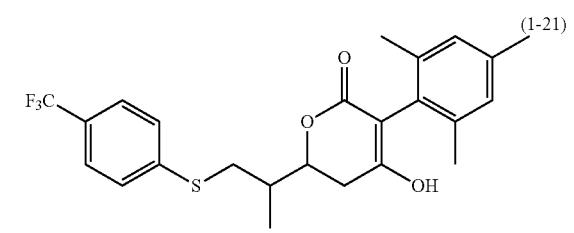
(1-21)
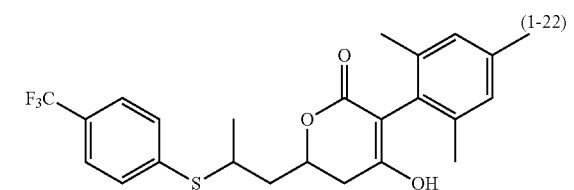
(1-22)
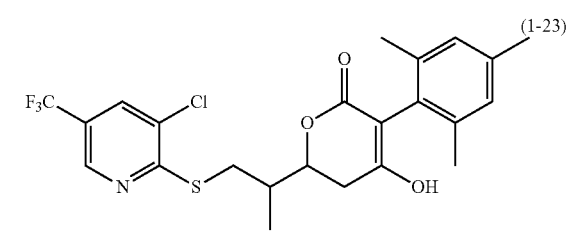
(1-23)
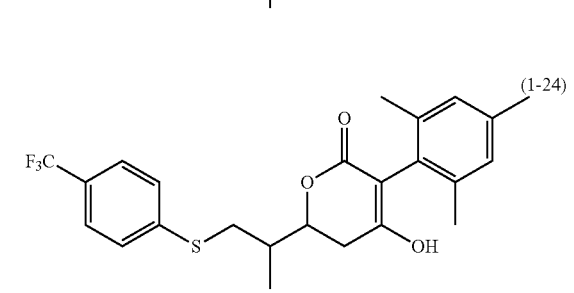
(1-24)
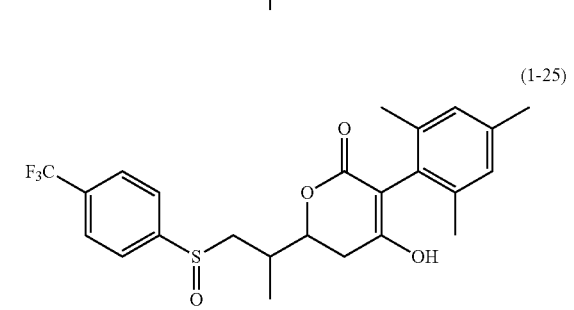
(1-25)
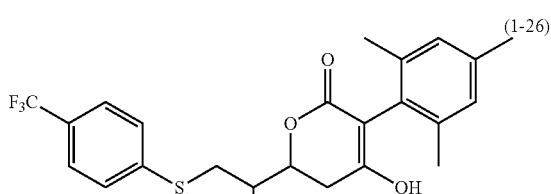
(1-26)
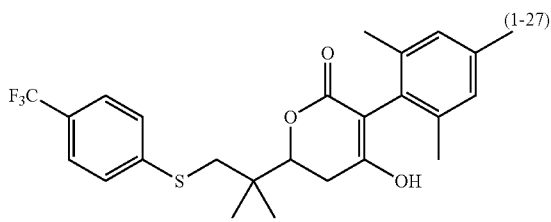
(1-27)
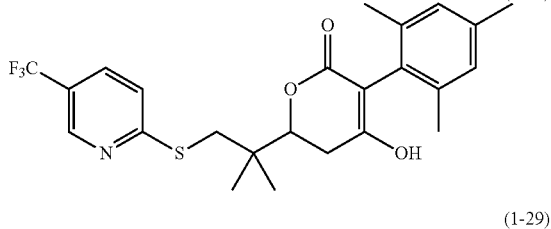
(1-28)
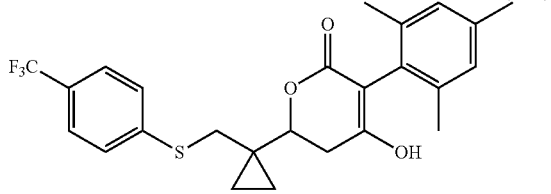
(1-29)
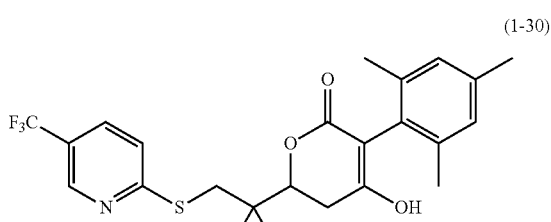
(1-30)
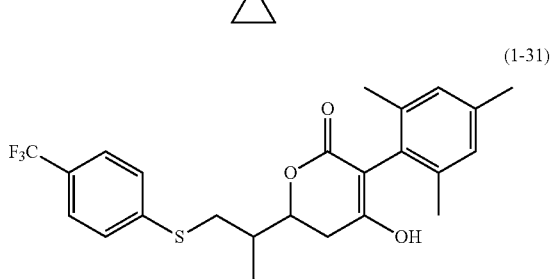
(1-31)
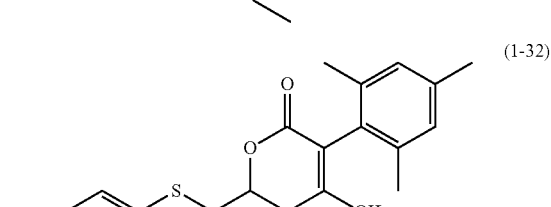
(1-32)

(1-33)
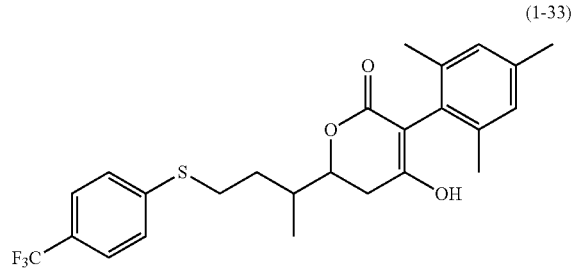
(1-34)
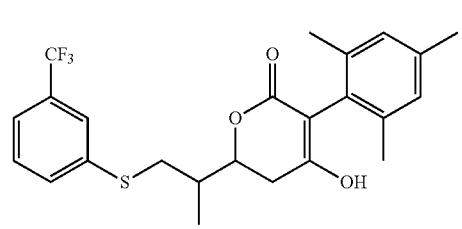
(1-35)
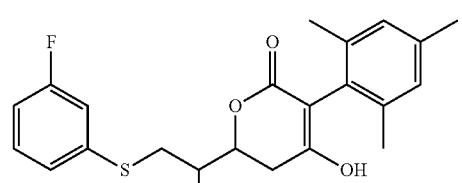
(1-36)
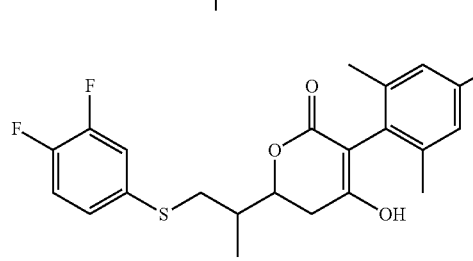
(1-37)
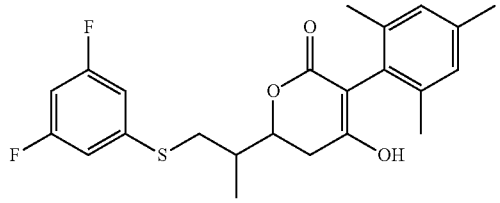
(1-38)
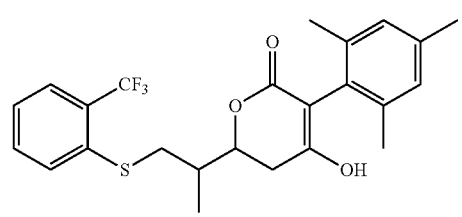
(1-39)
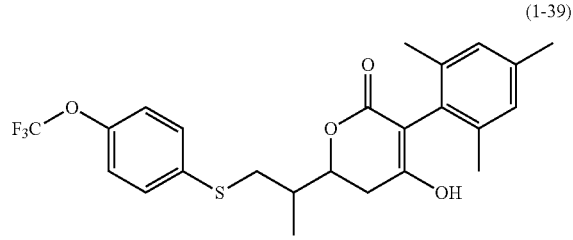
(1-40)
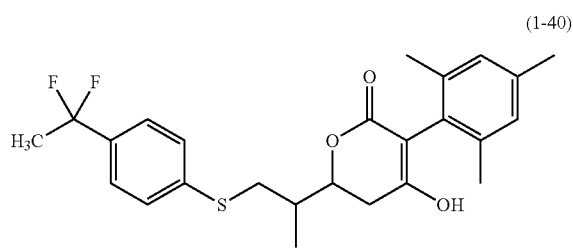
(1-41)
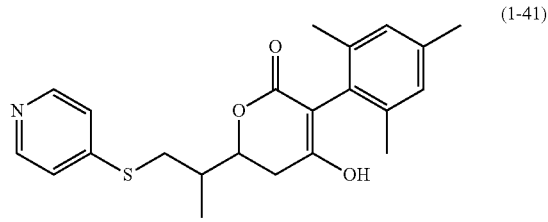
(1-42)
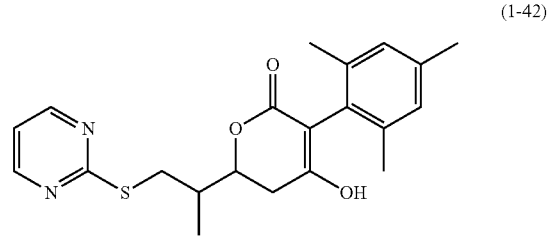
(1-43)
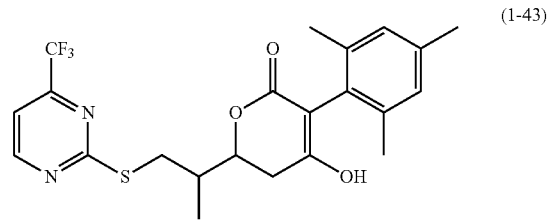
(1-44)
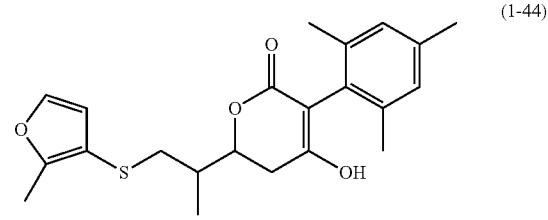
(1-45)
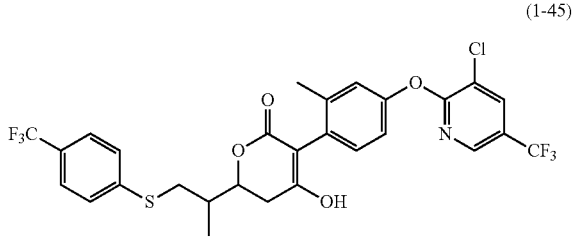
(1-46)
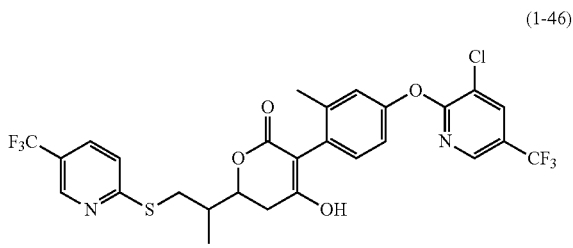

(1-47)
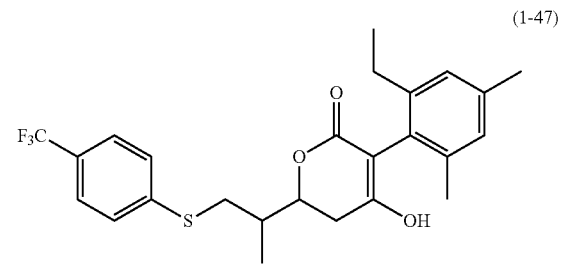
(1-48)
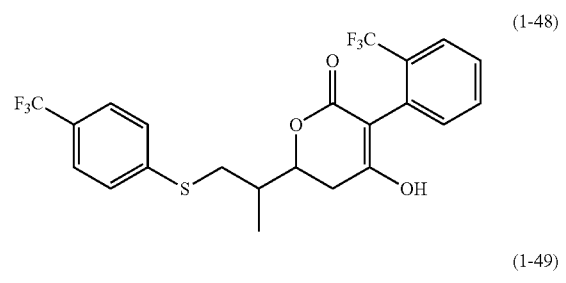
(1-49)
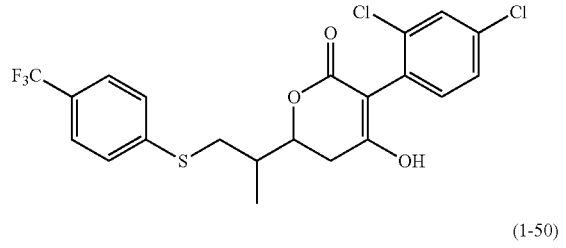
(1-50)
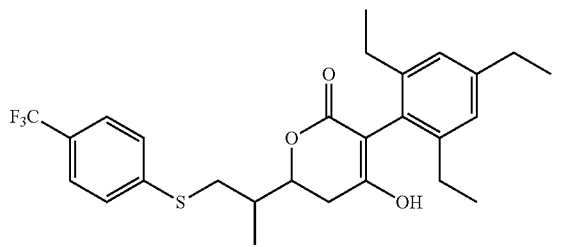
(1-51)
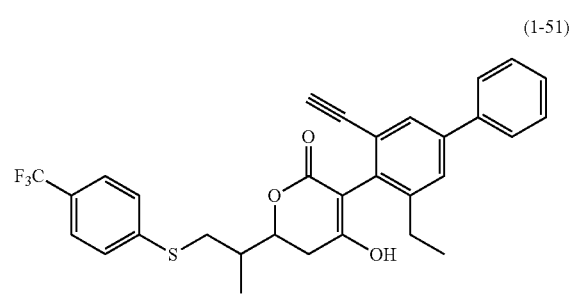
(1-52)
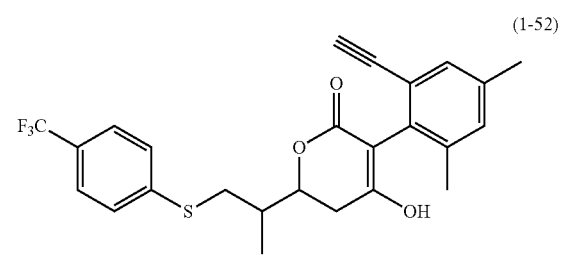
(1-53)
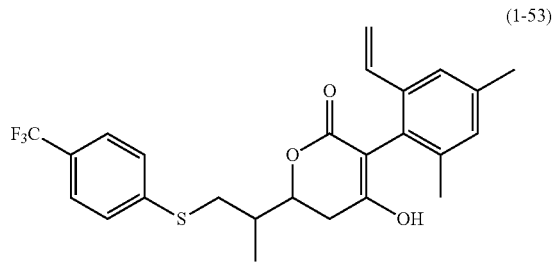
(1-54)
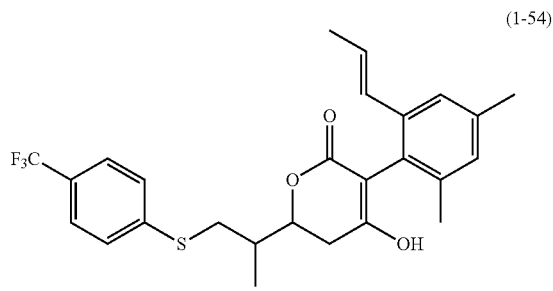 [SMILES: CCc1cc(C)cc(CC)c1C1=C(O)CC(C(C)CSc2ccc(C(F)(F)F)cn2)OC1=O]
(1-55)
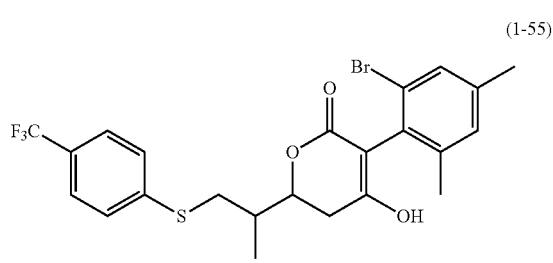
(1-56)
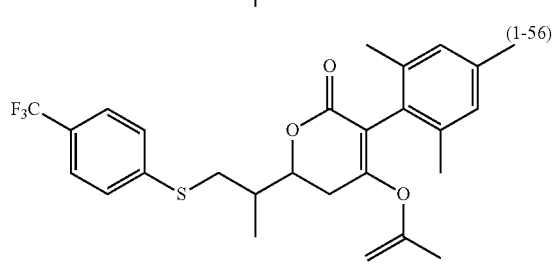
(1-57)
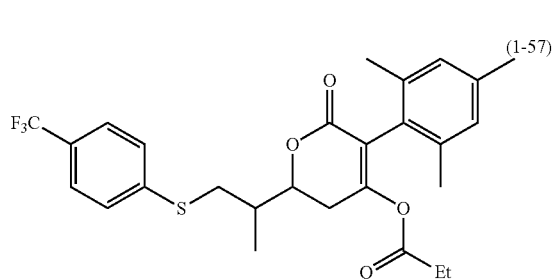
(1-58)
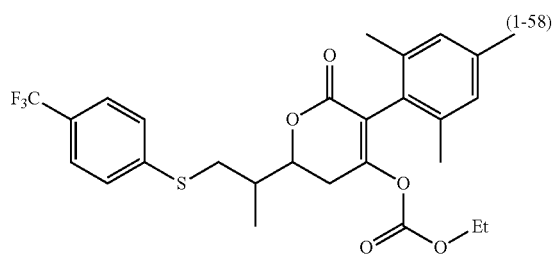

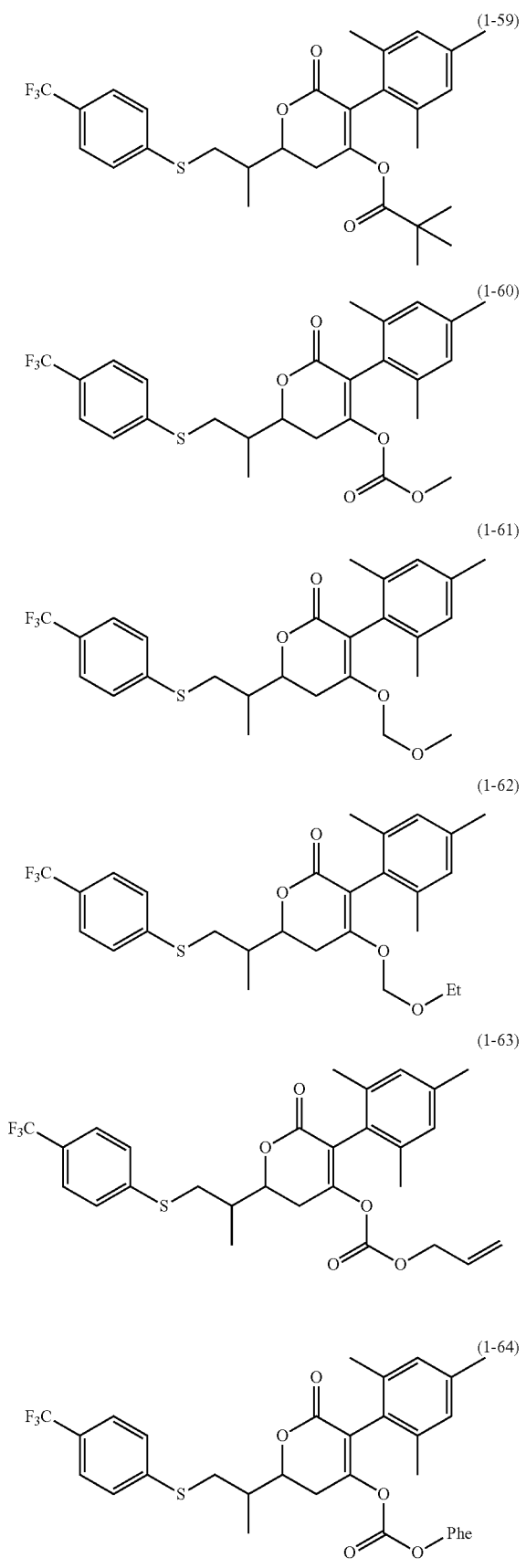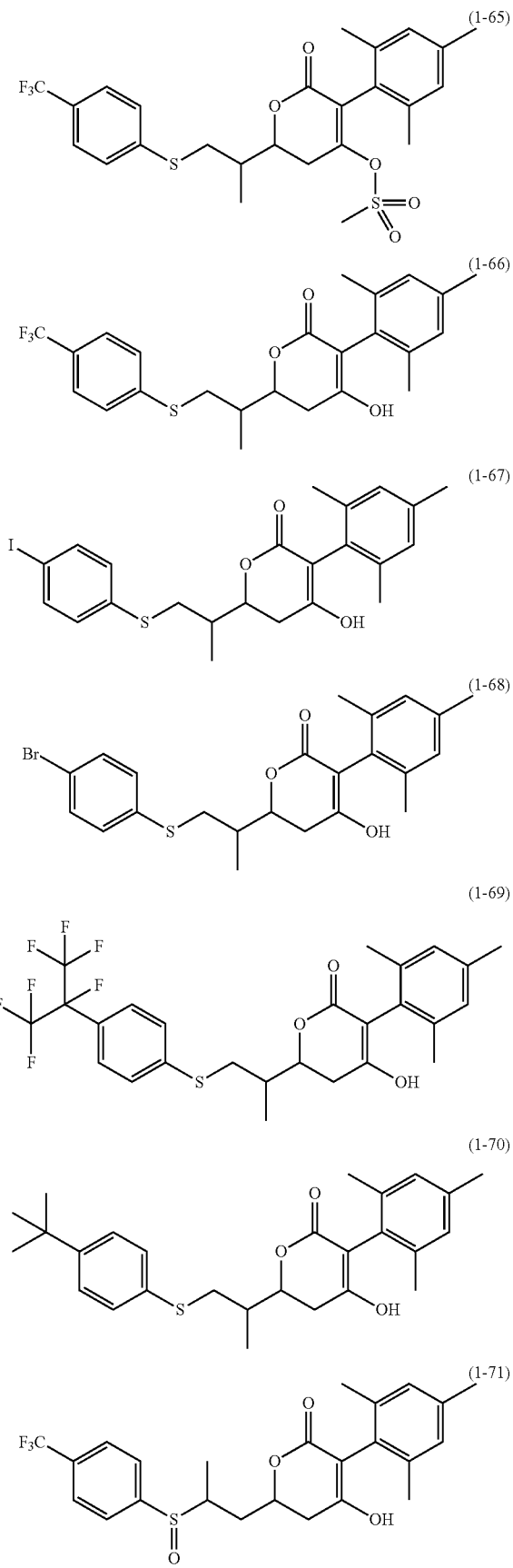

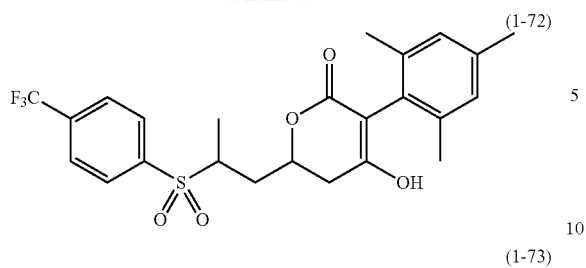
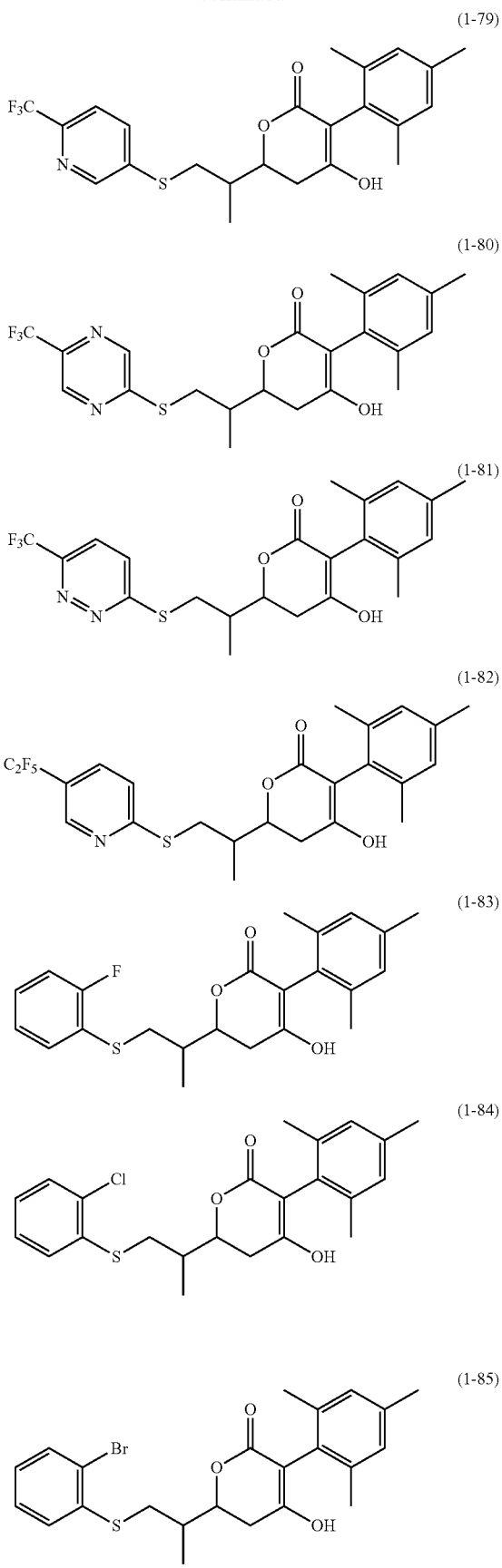

(1-86) 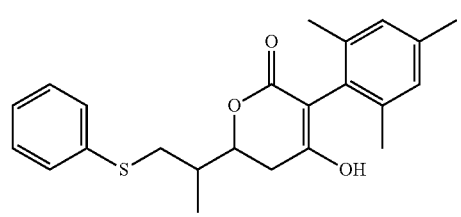
(1-87) 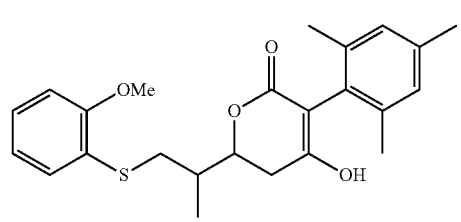
(1-88) 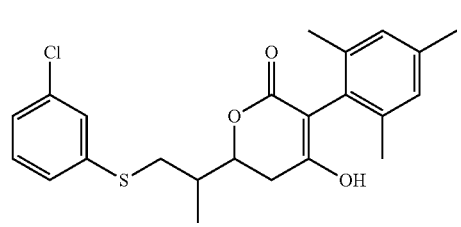
(1-89) 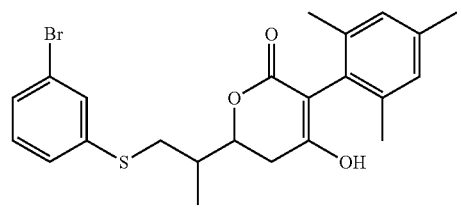
(1-90) 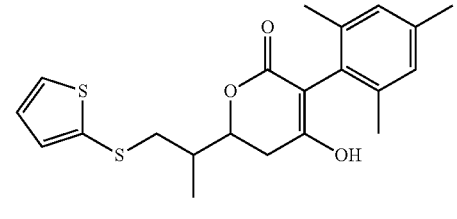
(1-91) 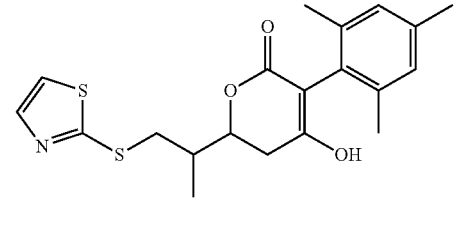
(1-92) 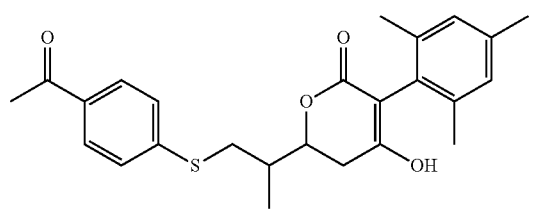
(1-93) 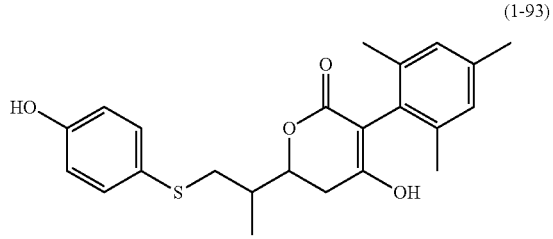
(1-94) 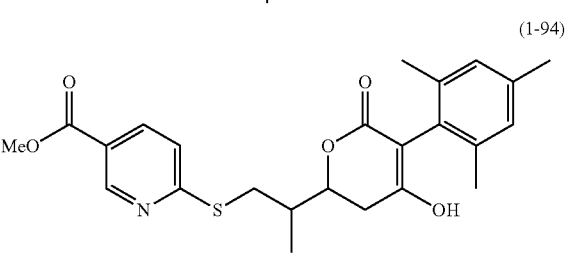
(1-95) 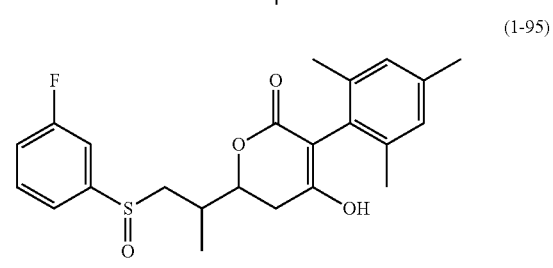
(1-96) 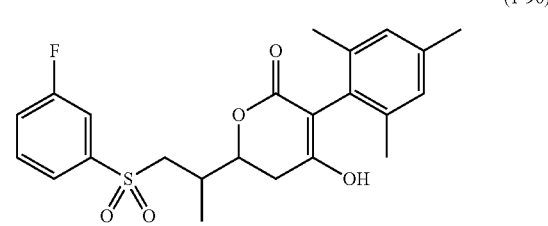
(1-97) 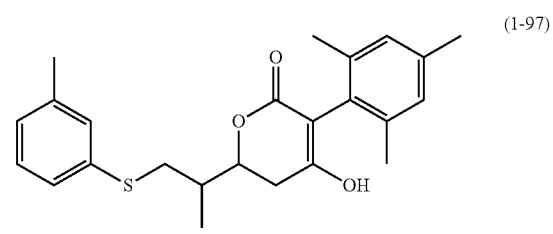
(1-98) 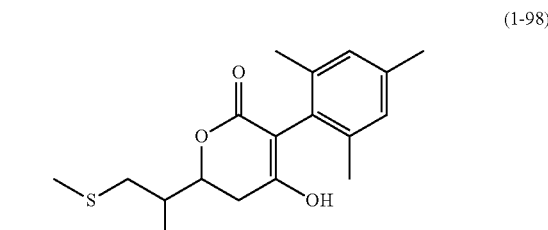
(1-99) 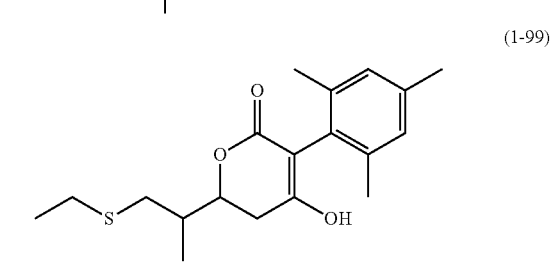

(1-100) 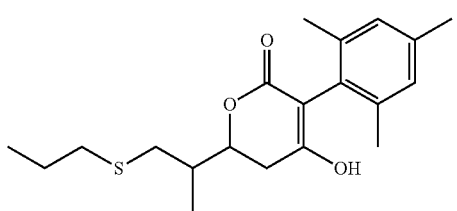

(1-101) 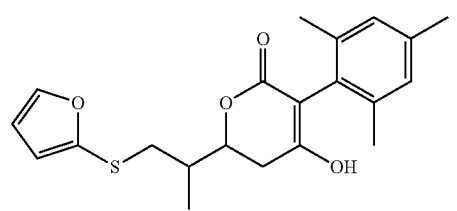

(1-102) 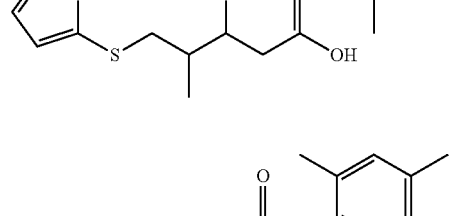

(1-103) 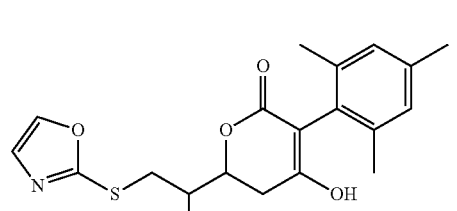

(1-104) 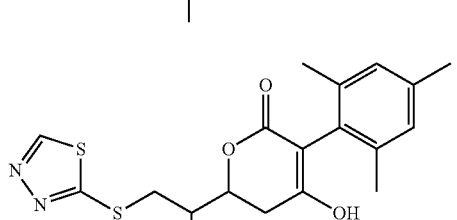

(1-105) 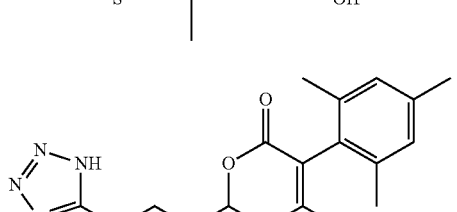

(1-106) 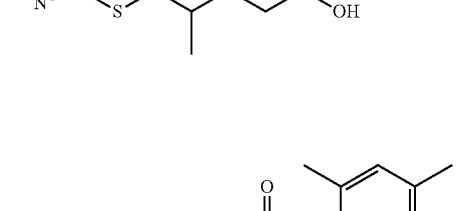

(1-107) 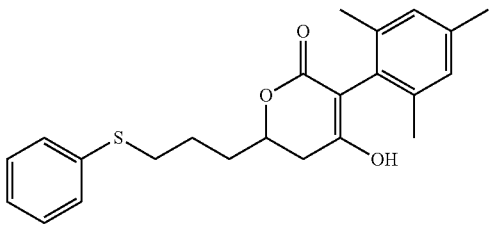

(1-108) 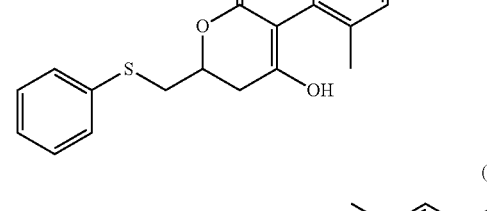

(1-109) 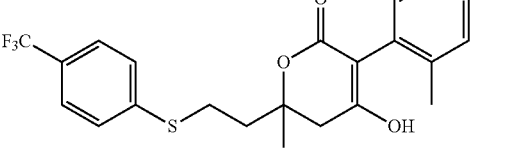

EXAMPLES

The present invention is described below in more detail with Preparation Examples, Reference Examples, Formulation Examples and Test Examples, but the present invention should not be construed to be limited thereto.

The "room temperature" (hereinafter sometimes abbreviated to as "RT") described in Preparation Example and Reference Examples means usually 10 to 30° C. $^1$H NMR means a proton nuclear magnetic resonance spectrum and Tetramethyl silane is used as an internal standard and chemical shift (δ) is expressed in ppm.

The following abbreviations are sometimes used in Preparation Examples and Reference Examples. CDCl$_3$: Deuterated chloroform, s: singlet, d: doublet, t: triplet, q: quartet, m: multiplet, Me: methyl group, Et: ethyl group, Phe: phenyl group, OMe: methoxy group, EtOAc: ethyl acetate, TBS: tert-butyldimethylsilyl group, eq.: equivalent, petether: petroleum ether and RM: reaction mixture.

Preparation Example 1-1

Preparation of a Compound of Formula (1-1)

Preparation of a Compound of Formula 14-1

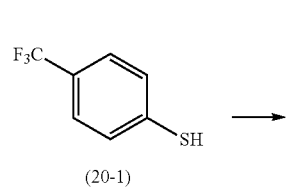

(20-1)

-continued

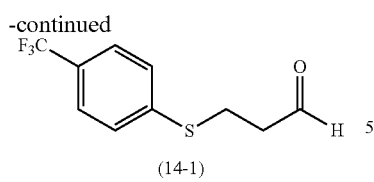

(14-1)

At RT, a compound of formula (20-1) 15 g and tetrahydrofuran 45 ml were mixed and then stirred. The resulting mixture was cooled to 0° C., and thereto were then added acrolein (90%) 8.1 ml and triethylamine 0.4 ml drop wise. The resulting mixture was stirred under ice-cooling for 3 hours; To the resulting reaction mixture was then added water. The resulting mixture was extracted with tert-butyl methyl ether. The organic layer was washed with water and dried over anhydrous Na$_2$SO$_4$, and concentrated under reduced pressure to afford the compound of formula (14-1) 19.8 g.

$^1$H NMR (CDCl$_3$)

δ ppm: 9.79 (1H, s), 7.54 (2H, d), 7.38 (2H, d), 3.25 (2H, t), 2.84 (2H, t)

Preparation of a Compound of Formula 12-1

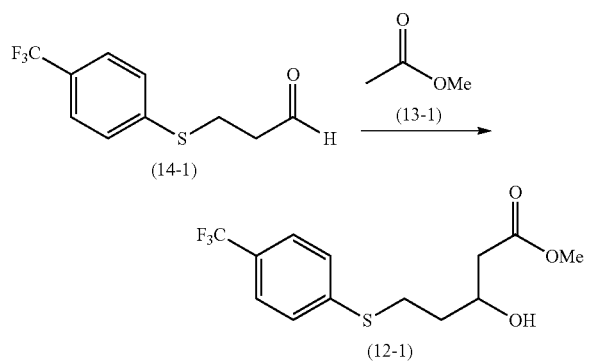

Under nitrogen atmosphere, diisopropylamine 14.4 ml was diluted with tetrahydrofuran 85 ml. The resulting solution was cooled to −78° C. and thereto was added n-butyl lithium (1.63 M hexane solution) 63.4 ml drop wise. The reaction solution was then stirred at 0° C. for about 10 minutes and cooled to −78° C. again, and thereto was added slowly a compound of formula (13-1) 8.0 ml drop wise. The resulting mixture was stirred at the same temperature for about 1 hour. To the resulting solution was added slowly a diluted solution of a compound of formula (14-1) 19.8 g in tetrahydrofuran 100 ml drop wise over about 1 hour. The resulting reaction solution was stirred at the same temperature for about two hours. To the reaction solution was then added aqueous saturated ammonium chloride solution 300 ml, and the organic layer were extracted with ethyl acetate and washed with saturated saline, and dried over anhydrous MgSO$_4$. The resulting organic layer was concentrated under reduced pressure to afford crude compound of formula (12-1) 26 g.

$^1$H NMR (d-DMSO)

δ ppm: 7.51 (2H, d), 7.37 (2H, d), 4.21-4.17 (1H, m), 3.72 (3H, s), 3.24-3.04 (3H, m), 2.55-2.43 (2H, m), 1.93-1.73 (2H, m)

Preparation of a Compound of Formula 10-1

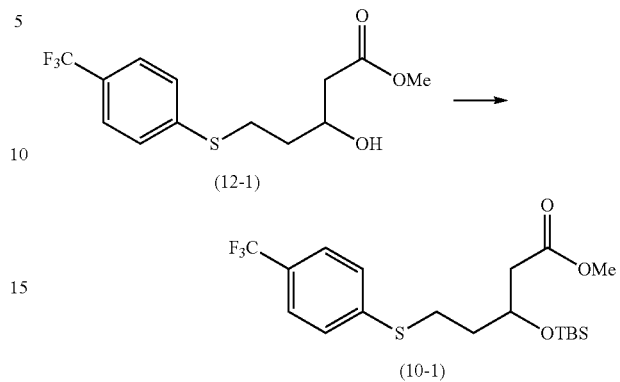

The compound of formula (12-1) 25.9 g and imidazole 14.3 g were dissolved in anhydrous N,N-dimethylformamide 150 ml. To the resulting mixture was added at RT tert-butyl dimethylchlorosilane 15.2 g and the resulting mixture was stirred for about 12 hours. To the reaction mixture was added water 200 ml and the resulting mixture was extracted with tert-butyl methyl ether. The organic layer was washed with saturated brine, and dried over anhydrous MgSO$_4$, and concentrated under reduced pressure to afford crude product of a compound of formula (10-1). The crude product was purified by column chromatography using (SiO$_2$) by eluting EtOAc:hexane (1:20) to afford the compound of formula (10-1) 34 g as pale yellow oil.

$^1$H NMR (CDCl$_3$)

δ ppm: 7.51 (2H, d), 7.35 (2H, d), 4.30-4.24 (1H, m), 3.65 (3H, s), 3.09-2.95 (2H, m), 2.50 (2H, ddd), 1.87 (2H, td), 0.88 (9H, s), 0.07 (3H, s), 0.06 (3H, s)

Preparation of a Compound of Formula 9-1

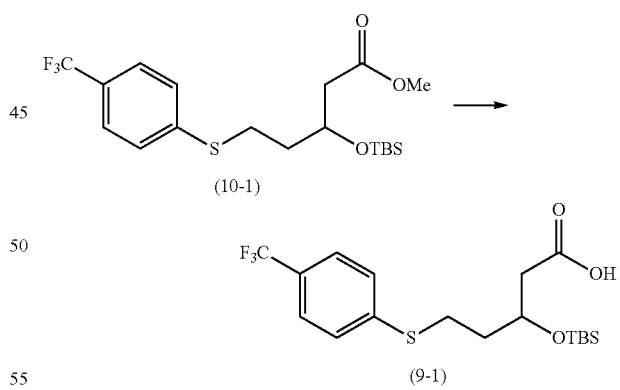

The compound of formula (10-1) 34 g was dissolved in a mixed solution of tetrahydrofuran 60 ml and water 40 ml. To the resulting solution was added lithium hydroxide monohydroxide 8.45 g and the resulting mixture was heated under reflux for about 4 hours. The resulting reaction solution was then cooled to RT and thereto was added 3N hydrochloric acid 130 ml, and the resulting mixture was extracted with ethyl acetate. The obtained organic layer was dried over anhydrous MgSO$_4$ and filtered. The obtained filtrate was concentrated under reduced pressure to afford a compound of formula (9-1) 31.8 g.

¹H NMR (CDCl₃)

δ ppm: 7.51 (2H, d), 7.35 (2H, d), 4.31-4.25 (1H, m), 3.12-2.96 (2H, m), 2.56-2.53 (2H, m), 1.90 (2H, td), 0.89 (9H, s), 0.09 (6H, s)

Preparation of a Compound of Formula 6-1

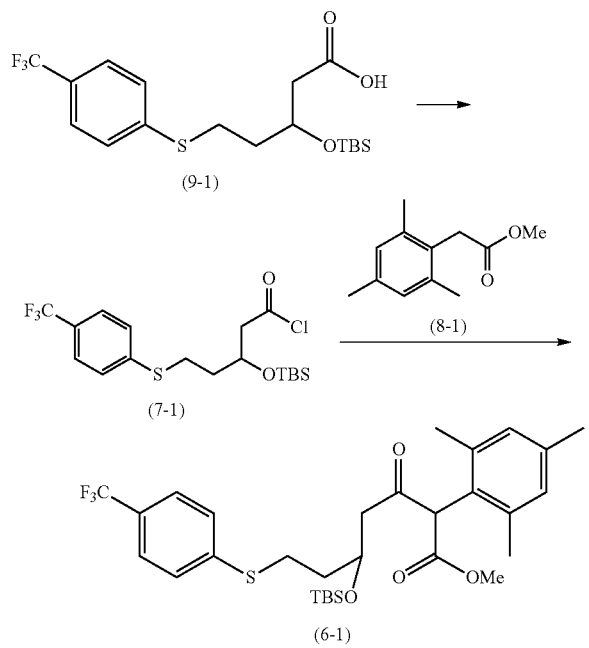

At 0° C. under ice-cooling, a compound of formula (9-1) 2.0 g was dissolved in dehydrated chloroform 40 ml, and to the resulting solution was added 1-chloro-2-methyl-1-propenyl dimethylamine 0.78 ml. The resulting mixture was then raised to RT and stirred for about 3 hours. The resulting reaction solution was then concentrated under reduced pressure.

Under nitrogen atmosphere, diisopropylamine 1.67 ml was diluted with tetrahydrofuran 18 ml and the resulting solution was cooled to −78° C. and thereto was added n-butyl lithium (1.63 M hexane solution) 6.7 ml drop wise. The reaction solution was then stirred at 0° C. for about 10 minutes and cooled to −78° C. again. Thereto was added slowly a solution of a compound of formula (8-1) 1.0 g in tetrahydrofuran 6 ml drop wise and the resulting mixture was stirred at the same temperature for about 1 hour. To the resulting solution was added slowly a solution of a compound of formula (7-1) in tetrahydrofuran 12 ml drop wise. The resulting reaction solution was stirred at the same temperature for about 5 hours. The resulting reaction solution was poured into 0.5 N hydrochloric acid 100 ml, and the organic layer was extracted with ethyl acetate and washed with saturated brine, and dried over anhydrous MgSO₄. The resulting organic layer was concentrated under reduced pressure to afford crude product of a compound of formula (6-1) 3.35 g. The obtained oil was purified by column chromatography using (SiO₂) by eluting EtOAc:hexane (1:99) to afford a compound of formula (6-1) 640 mg.

¹H NMR (CDCl₃)

δ ppm: 13.19 (1H, s), 7.62 (2H, d), 7.44 (2H, d), 7.00-6.98 (2H, m), 4.20-4.14 (1H, m), 3.80 (3H, s), 3.05-3.00 (2H, m), 2.44-2.35 (5H, m), 2.18-2.15 (6H, m), 1.95-1.79 (2H, m), 0.95 (9H, s), 0.14 (3H, s), 0.08 (3H, s)

Preparation of a Compound of Formula 2-1

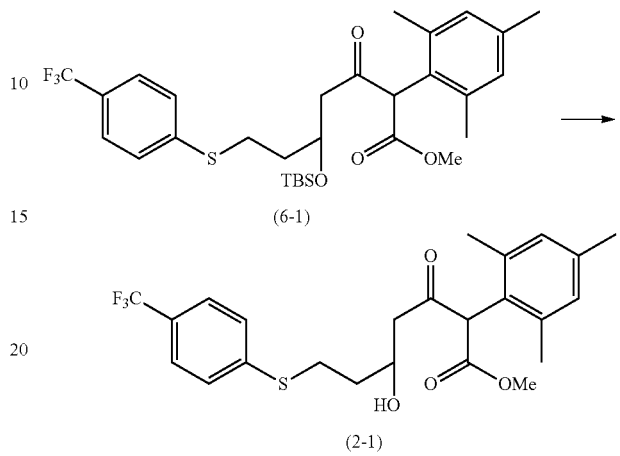

The compound of formula (6-1) 640 mg was dissolved in tetrahydrofuran 5 ml. To the resulting mixture was added at RT tetrabutylammonium fluoride 1.44 ml drop wise and the reaction mixture was stirred at RT for 4 hours. To the reaction mixture were added 0.5 N hydrochloric acid 30 ml and ethyl acetate 30 ml and the organic layer was separated. The obtained organic layer was dried over anhydrous MgSO₄ and concentrated under reduced pressure to crude product of a compound of formula (2-1) 570 mg.

¹H NMR (CDCl₃)

δ ppm: 13.34 (1H, s), 7.49 (2H, d), 7.31 (2H, d), 6.86 (2H, s), 4.13-4.06 (1H, m), 3.69 (3H, s), 3.35-3.30 (2H, s), 3.09-2.92 (2H, m), 2.31-2.04 (12H, m)

Preparation of a Compound of Formula 1-1

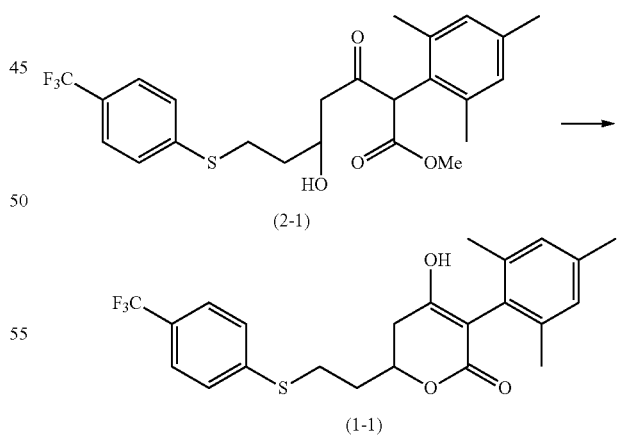

Under nitrogen atmosphere, the compound of formula (2-1) 570 mg was heated under reflux with stirring in oil bath which set outside temperature to 150° C. for about 30 minutes. The resulting mixture was then cooled to RT and the obtained oil was purified by column chromatography using (SiO₂) by eluting EtOAc:hexane (1:2) to afford a compound of formula (1-1) 154 mg.

$^1$H NMR (CDCl$_3$)

δ ppm: 7.54 (2H, d), 7.41 (2H, d), 6.96 (2H, s), 5.79 (1H, s), 4.75-4.68 (1H, m), 3.35-3.17 (2H, m), 2.78-2.53 (2H, m), 2.32-2.01 (11H, m)

Preparation Example 1-2

Preparation of a Compound of Formula (1-2)

Preparation of a Compound of Formula 14-2

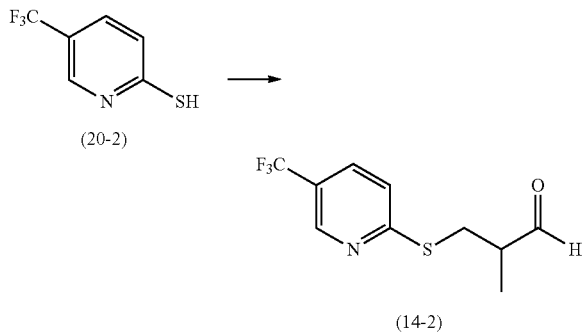

At RT, a compound of formula (20-2) 15 g and tetrahydrofuran 90 ml were mixed and stirred, and the resulting mixture was cooled to 0° C. and thereto were then added methacrolein 9.0 ml and triethylamine 1.1 ml drop wise successively, and the resulting mixture was stirred under ice-cooling for 5 hours. To the resulting mixture was then added water and the resulting mixture was extracted with test-butyl methyl ether. The organic layer was washed with water and dried over anhydrous Na$_2$SO$_4$ and concentrated under reduced pressure to a compound of formula (14-2) 20.8 g.

$^1$H NMR (CDCl$_3$)

δ ppm: 9.73 (1H, s), 8.66 (1H, s), 7.67 (1H, d), 7.27 (1H, d), 3.59-3.54 (1H, m), 3.38-3.33 (1H, m), 2.86-2.81 (1H, m), 1.26 (3H, d)

Preparation of a Compound of Formula 12-2

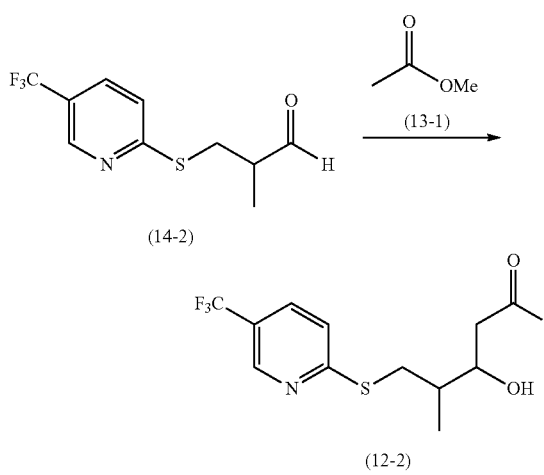

Under nitrogen atmosphere, diisopropylamine 14.0 ml was diluted with tetrahydrofuran 85 ml, and the resulting solution was cooled to −78° C. and thereto was then added n-butyl lithium (1.63 M hexane solution) 62.3 ml drop wise. The reaction solution was then stirred at 0° C. for about 10 minutes and cooled to −78° C. again, and thereto was added slowly a diluted solution of a compound of formula (13-1) 8.0 ml in tetrahydrofuran 45 ml drop wise and the resulting mixture was stirred at the same temperature for about 1 hour. To the resulting solution was added slowly a diluted solution of a compound of formula (14-2) 20.8 g in tetrahydrofuran 100 ml drop wise over about 1 hour. The resulting reaction solution was stirred at the same temperature for about 2 hours. To the above-mentioned reaction solution was then added aqueous saturated ammonium chloride solution 330 ml, and the organic layer was extracted with ethyl acetate and washed with saturated saline, and dried over anhydrous MgSO$_4$. The obtained organic layer was concentrated under reduced pressure to afford crude product of a compound of formula (12-2) 18.5 g.

$^1$H NMR (d-DMSO)

δ ppm: 8.63 (1H, s), 7.68 (1H, d), 7.34-7.30 (1H, m), 4.69-4.26 (1H, m), 4.07-3.88 (1H, m), 3.71 (3H, d), 3.53-3.41 (1H, m), 3.39-3.00 (1H, m), 2.66-2.57 (1H, m), 2.52-2.41 (1H, m), 1.07-1.02 (3H, m)

Preparation of a Compound of Formula 10-2

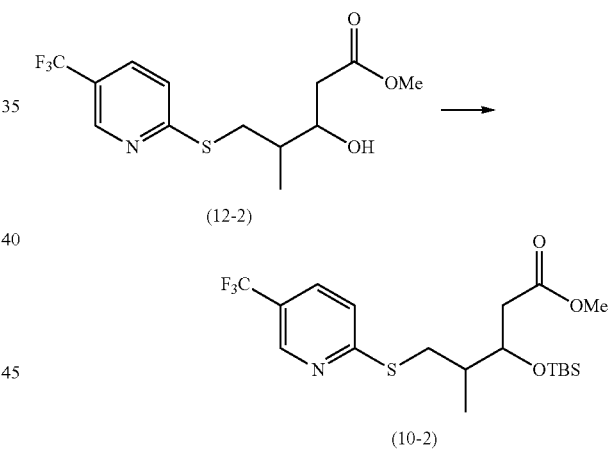

The compound of formula (12-2) 18.3 g and imidazole 9.62 g were dissolved in anhydrous N,N-dimethylformamide 150 ml. To the resulting mixture was added at RT tert-butyl dimethylchlorosilane 10.2 g and the resulting mixture was stirred for about twelve hours. To the reaction mixture was added water 200 ml and the resulting mixture was extracted with tert-butyl methyl ether. The organic layer was washed with saturated saline and dried over anhydrous MgSO$_4$, and concentrated under reduced pressure to afford crude product of a compound of formula (10-2). The crude product was purified by column chromatography using (SiO$_2$) by eluting EtOAc:hexane (1:10) to afford a compound of formula (10-2) as pale yellow oil 15.1 g.

$^1$H NMR (CDCl$_3$)

δ ppm: 8.63 (1H, s), 7.64 (1H, d), 7.26 (1H, d), 4.36-4.24 (1H, m), 3.66 (3H, d), 3.48-3.31 (1H, m), 3.11-2.81 (1H, m), 2.62-2.44 (2H, m), 2.05-1.90 (1H, m), 1.03 (3H, dd), 0.87 (9H, d), 0.11-0.03 (6H, m)

Preparation of a Compound of Formula 9-2

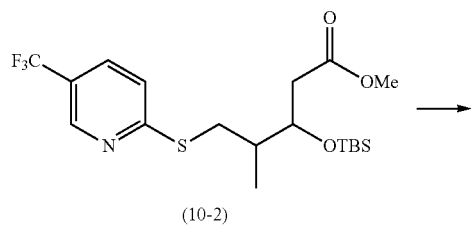

(10-2)

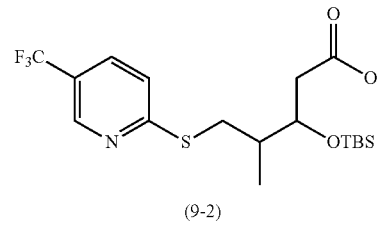

(9-2)

A compound of formula (10-2) 15 g was added to a mixed solution of tetrahydrofuran 27 ml and water 18 ml. To the resulting solution was added 98% lithium hydroxide 2.1 g and the resulting mixture was heated under reflux for about 4 hours. The resulting reaction solution was then cooled to RT, and to the reaction solution was added 0.1 N aqueous sodium hydrogen sulfate solution 100 ml so as to make pH 3. The resulting mixture was then extracted with ethyl acetate. The obtained organic layer was dried over anhydrous MgSO₄ and filtered. The obtained filtrate was concentrated under reduced pressure to afford a compound of formula (9-2) 14.7 g.

¹H NMR (CDCl₃)
δ ppm: 8.65 (1H, s), 7.64 (1H, d), 7.26 (1H, d), 4.35-4.23 (1H, m), 3.48-3.33 (1H, m), 3.10-2.82 (1H, m), 2.67-2.51 (2H, m), 2.07-1.97 (1H, m), 1.09-1.02 (3H, m), 0.91-0.84 (9H, m), 0.11-0.05 (6H, m)

Preparation of a Compound of Formula 7-2

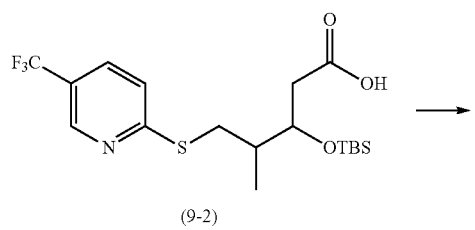

(9-2)

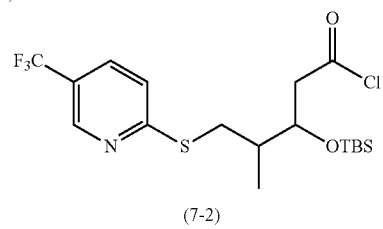

(7-2)

At 0° C. under ice-cooling, a compound of formula (9-2) 2 g was dissolved in dehydrated chloroform 40 ml and to the resulting solution was added 1-chloro-2-methyl-1-propenyl dimethylamine 0.75 ml, and the resulting mixture was then raised to RT and stirred for about 3 hours. The resulting reaction solution was then concentrated under reduced pressure to afford crude product of a compound of formula (7-2). The compound of formula (7-2) was used in the next reaction without further purification.

Preparation of a Compound of Formula 1-2

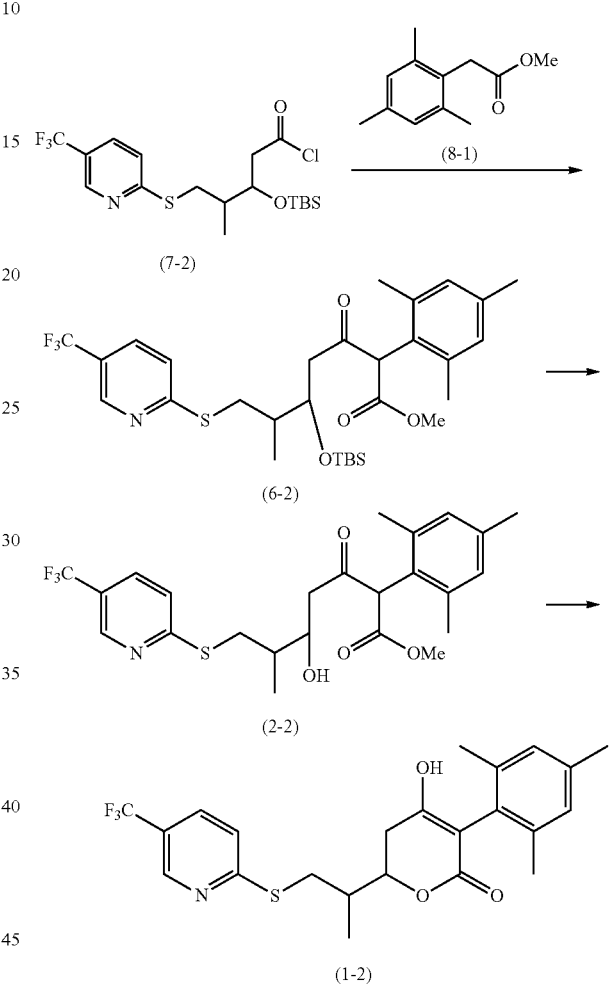

Under nitrogen atmosphere, diisopropylamine 3.8 ml was diluted with tetrahydrofuran 50 ml and the resulting solution was cooled to −78° C., and thereto was then added n-butyl lithium (1.63 M hexane solution) 16 ml drop wise. The reaction solution was then stirred at 0° C. for about 10 minutes and cooled to −78° C. again. Thereto was added slowly a solution of a compound of formula (8-1) 2.4 g in tetrahydrofuran 30 ml drop wise, and the resulting mixture was stirred at the same temperature for about 1 hour. To the resulting solution was added slowly a solution of a compound of formula (7-2) in tetrahydrofuran 15 ml drop wise. The resulting reaction solution was stirred at the same temperature for about 5 hours. The resulting reaction solution was poured into 1N hydrochloric acid 260 ml, and the organic layer was extracted with ethyl acetate and washed with saturated saline and then dried over anhydrous MgSO₄. The obtained organic layer was concentrated under reduced pressure to afford crude product of a compound of formula (6-2) 9.27 g.

Successively, the crude product of the compound of formula (6-2) 9.27 g was dissolved in tetrahydrofuran 150 ml. To the resulting mixture was added at RT tetrabutylammonium fluoride 16.2 ml drop wise and the resulting mixture was stirred at RT for 4 hours. To the reaction mixture were added water and ethyl acetate 30 ml and the organic layer was separated. The obtained organic layer was dried over anhydrous MgSO₄ and then concentrated under reduced pressure to afford crude product of a compound of formula (2-2) 2.5 g.

Under nitrogen atmosphere, the crude product of compound of formula (2-2) 2.5 g was heated in oil bath which set outside temperature to 150° C. for about 30 minutes. The reaction mixture was then cooled to RT and the obtained oil was purified by column chromatography using (SiO₂) by eluting EtOAc:hexane (1:2) to afford a compound of formula (1-2) 166.8 mg.

¹H NMR (CDCl₃)

δ ppm: 8.61 (1H, d), 7.66 (1H, dd), 7.28 (1H, dd), 6.88 (2H, s), 4.67-4.42 (1H, m), 3.66-3.61 (0.5H, m), 3.43 (0.5H, dd), 3.24 (0.5H, dd), 3.10 (0.5H, dd), 2.83-2.73 (1H, m), 2.49-2.24 (5H, m), 2.07 (6H, s), 1.20-1.13 (3H, m)

The present compound as shown below was prepared according to a process of Preparation example 1-2 using 2,6-diethyl-4-methyl phenyl acetic acid methyl ester instead of a compound of formula (8-1).

Compound of Formula 1-3

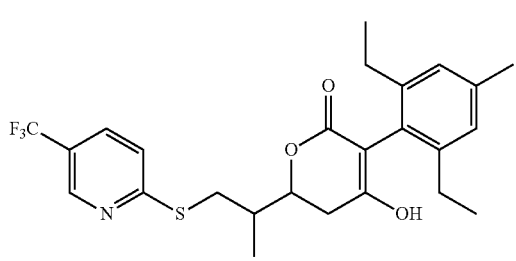

(1-3)

¹H NMR (CDCl₃)

δ ppm: 8.67-8.65 (1H, m), 7.68 (1H, dd), 7.33-7.28 (1H, m), 7.00 (1H, s), 6.97 (1H, s), 6.06 (1H, s), 4.72-4.68 (1H, m), 3.72-3.48 (1H, m), 3.31-3.15 (1H, m), 2.94-2.85 (1H, m), 2.61-2.17 (9H, m), 1.29-1.02 (9H, m)

Preparation Example 1-3

Preparation of a Compound Formula (1-15)

Preparation of a Compound of Formula 30-15

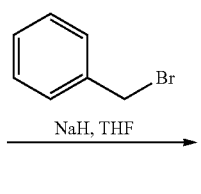

(31-15)

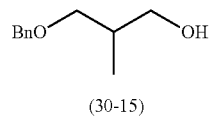

(30-15)

To a suspension of NaH (40 g, 1666.69 mmol) in dry THF (1000 mL) was added 2-methylpropane-1,3-diol (31-15) (150 g, 1666.69 mmol; 1 eq.) in dry THF (500 mL) at 0° C. over a period of 10 min. The reaction mixture was heated to 50° C. for 1 h. At the same temperature Benzyl bromide (98.89 g, 555.57 mmol) was added and reaction mixture was heated to 65° C. for 12 h. After completion, the reaction mixture was poured into saturated NH₄Cl solution, extracted with EtOAc (2 times), EtOAc layer was washed with water, brine, dried over anhydrous Na₂SO₄, filtered and the solvent was evaporated under reduced pressure to get crude compound. The crude compound was purified by silica gel (60-120 mesh) column chromatography, eluted with 20% EtOAc/pet ether to afford 3-(benzyloxy)-2-methylpropan-1-ol (30-15) as brown colour liquid (117 g, 78%); ¹H NMR (400 MHz, cdcl₃) δ 7.38-7.24 (m, 5H), 4.52 (s, 2H), 3.61 (dt, J=6.7, 4.2 Hz, 2H), 3.59-3.50 (m, 1H), 3.43 (dd, J=9.1, 8.0 Hz, 1H), 2.56 (dd, J=6.5, 4.2 Hz, 1H), 2.14-2.01 (m, 1H), 0.89 (d, J=7.0 Hz, 3H); Mass (M+H): 181, LCMS Purity: 66.04%.

Preparation of a Compound of Formula 29-15

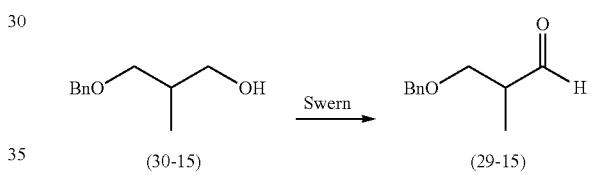

To a solution dimethyl sulfoxide (62 mL, 833.1 mmol) in dichloromethane (100 mL) was added oxalyl chloride (38.5 mL, 416.55 mmol) at −78° C. and stirred the reaction mixture for 20 min. and 3-(benzyloxy)-2-methylpropan-1-ol (30-15) (50 g, 277.7 mmol) in dry dichloromethane (400 mL) was added to the reaction mixture and again stirred for 20 min at −78° C. Followed by the addition of triethyl amine (168 mL, 11110.8 mmol) at −78° C. and stirred at RT for 18 h. After completion, the RM was diluted with water, extracted with EtOAc (2 times), EtOAc layer was washed with water, brine, dried over anhydrous Na₂SO₄, filtered and the solvent was evaporated under reduced pressure to get crude compound. The crude compound was purified by silica gel (60-120 mesh) column chromatography, eluted with 5% EtOAc/pet ether to afford 3-(benzyloxy)-2-methylpropanal (29-15) as brown colour liquid (37 g, 75%); ¹H NMR (400 MHz, cdcl₃) δ 9.73 (d, J=1.6 Hz, 1H), 7.44-7.20 (m, 5H), 4.53 (s, 2H), 3.65 (td, J=9.6, 6.0 Hz, 2H), 2.73-2.62 (m, 1H), 1.14 (d, J=7.1 Hz, 3H); Mass (M+H): 179, LCMS Purity: 84.57%.

Preparation of a Compound of Formula 28-15

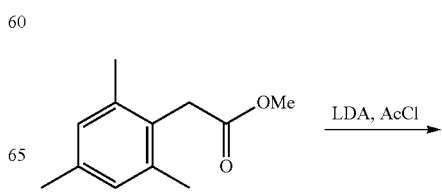

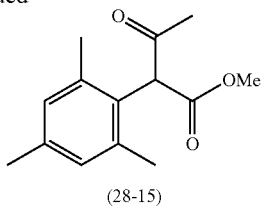

(28-15)

To the solution of methyl 2-mesitylacetate (86 g, 447.91 mmoles) in THF (860 mL) was added LDA (286 mL, 492.7 mmoles) at −78° C. and stirred at the same temperature for 30 min. followed by the addition of Acetyl chloride (34.9 mL, 537.49 mmoles) and the RM was stirred at the same temperature for 4 h and stirred at RT for 3 h. After completion, the RM was quenched with saturated ammonium chloride solution at 0° C., extracted with EtOAc (2 times), EtOAc layer was washed with water, brine, dried over anhydrous $Na_2SO_4$, filtered and the solvent was evaporated under reduced pressure to get crude compound. The crude compound was purified by silica gel (100-200 mesh) column chromatography, eluted with 1% EtOAc/pet ether to afford methyl 2-mesityl-3-oxobutanoate (28-15) as off white solid (10 g, 20%); $^1$H NMR (400 MHz, cdcl$_3$) δ 12.97 (d, J=1.0 Hz, 1H), 6.89 (s, 2H), 3.67 (s, 3H), 2.29 (s, 3H), 2.08 (s, 6H), 1.68 (s, 3H); Mass (M+H): 235, LCMS Purity: 91.62%.

Preparation of a Compound of Formula 27-15

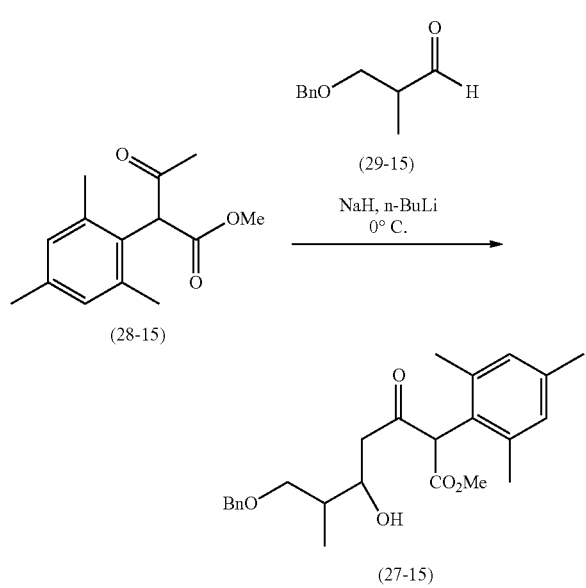

To a suspension of NaH (9.4 g, 237.18 mmoles) in THF(100 mL) was added the solution of methyl 2-mesityl-3-oxobutanoate (28-15)(18.5 g, 79.05 mmoles) in THF (190 mL) at 0° C. and stirred for 30 min. The RM was cooled to −40° C., followed by the addition of n-BuLi (197 mL, 316.23 mmoles) and stirred for 30 min. at the same temperature the solution of 3-(benzyloxy)-2-methylpropanal (29-15) (42 g, 237.18 mmoles) in THF (40 mL) was added over a period of 20 min. stirred at the same temperature for 30 min. After completion, the RM was quenched with saturated ammonium chloride solution at 0° C., extracted with EtOAc (2 times), EtOAc layer was washed with water, brine, dried over anhydrous $Na_2SO_4$, filtered and the solvent was evaporated under reduced pressure to get crude product. The crude compound was purified by silica gel (100-200 mesh) column chromatography, eluted with 20% EtOAc/pet ether to afford methyl 7-(benzyloxy)-5-hydroxy-2-mesityl-6-methyl-3-oxoheptanoate (27-15) as brown liquid (26 g, 80%); $^1$H NMR (400 MHz, cdcl$_3$) δ13.26 (d, J=10.0 Hz, 1H), 7.40-7.23 (m, 5H), 6.86 (d, J=3.6 Hz, 2H), 4.38 (s, 2H), 4.2-3.8 (m,1H), 3.67 (s, 3H), 3.44-3.31 (m, 2H), 2.27 (d, J=2.0 Hz, 3H), 2.12-2.04 (m, 9H), 1.8 (br s,1H) 0.79 (dd, J=19.2, 7.0 Hz, 3H); Mass (M+H): 413, LCMS Purity: 84.22%.

Preparation of a Compound of Formula 26-15

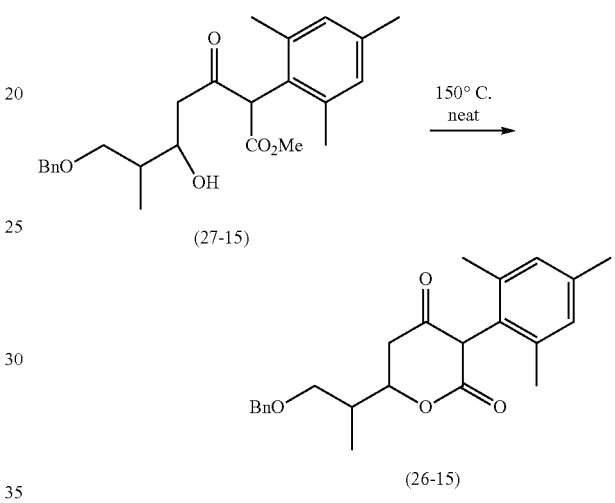

The methyl 7-(benzyloxy)-5-hydroxy-2-mesityl-6-methyl-3-oxoheptanoate (27-15) (26 g, 62.4 mmoles) was heated to 150° C. for 3 h. After completion, the RM was poured into ice water, extracted with EtOAc (2 times), EtOAc layer was washed with water, brine, dried over anhydrous $Na_2SO_4$, filtered and the solvent was evaporated under reduced pressure to get crude compound. The crude compound was purified by silica gel (100-200 mesh) column chromatography, eluted with 10% EtOAc/pet ether to afford 6-(1-(benzyloxy)propan-2-yl)-3-mesityldihydro-2H-pyran-2,4(3H)-dione (26-15) as brown liquid (14 g, 58%); $^1$H NMR (400 MHz, dmso) δ 10.66 (s, 1H), 7.39-7.26 (m, 5H), 6.84-6.77 (m, 2H), 4.56-4.39 (m, 3H), 3.62-3.39 (m, 2H), 2.81 (dt, J=17.1, 12.8 Hz, 1H), 2.57-2.51 (m, 1H), 2.21 (s, 3H), 2.19-2.04 (m, 1H), 2.00 (d, J=9.0 Hz, 6H), 1.01 (t, J=6.9 Hz, 3H); Mass (M+H): 380, LCMS Purity: 95.53%.

Preparation of a Compound of Formula 24-15

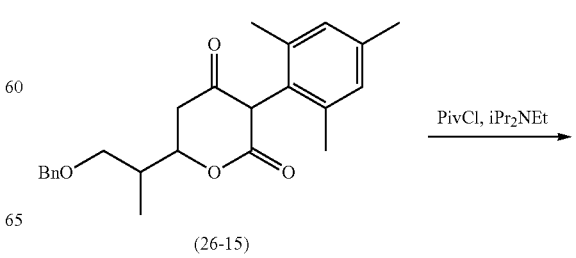

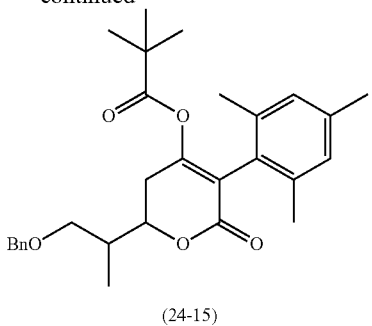

(24-15)

To a solution of Pivaloyl chloride (9.3 mL, 73.16 mmol) in pyridine (77 mL) was added 6-(1-(benzyloxy)propan-2-yl)-3-mesityldihydro-2H-pyran-2,4(3H)-dione (26-15) (14 g, 36.40 mmol) at RT and stirred at the same temperature for 18 h. After completion, the RM was poured into ice water, extracted with EtOAc (2 times), EtOAc layer was washed with 1N HCl, water, brine, dried over anhydrous Na$_2$SO$_4$, filtered and the solvent was evaporated under reduced pressure to afford 2-(1-(benzyloxy)propan-2-yl)-5-mesityl-6-oxo-3,6-dihydro-2H-pyran-4-yl pivalate (24-15) as oil mass (14 g, 82%); $^1$H NMR (400 MHz, cdcl$_3$) δ 7.38-7.26 (m, 5H), 6.83 (d, J=7.6 Hz, 2H), 4.87-4.70 (m, 1H), 4.61-4.47 (m, 2H), 3.65-3.54 (m, 2H), 3.02 (ddd, J=24.8, 17.4, 12.7 Hz, 1H), 2.48 (ddd, J=17.5, 9.9, 3.6 Hz, 1H), 2.31 (p, J=7.8, 7.1 Hz, 1H), 2.24 (s, 3H), 2.14-2.09 (m, 6H), 1.12 (dd, J=12.8, 7.0 Hz, 3H), 0.92 (s, 9H); Mass (M+H): 465, LCMS Purity: 98.58%.

Preparation of a Compound of Formula 23-15

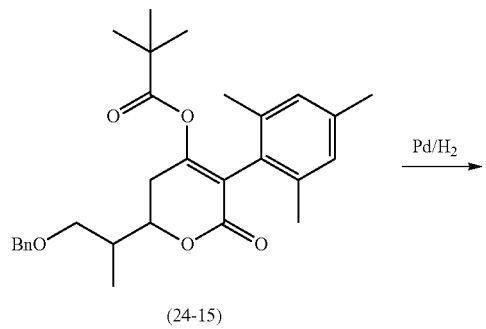

To a solution of 2-(1-(benzyloxy)propan-2-yl)-5-mesityl-6-oxo-3,6-dihydro-2H-pyran-4-yl pivalate (24-15) (8 g, 21.39 mmol) in of EtOH (12 mL) was added 10% of Pd on carbon (1.6 g) and hydrogenated at 20 psi for 18 h. After completion, the RM was filtered through celite pad and the filtrate was evaporated under reduced pressure to afford 2-(1-hydroxypropan-2-yl)-5-mesityl-6-oxo-3,6-dihydro-2H-pyran-4-yl pivalate (23-15) as off white solid (5.1 g, 80%); $^1$H NMR (400 MHz, cdcl$_3$) δ 6.83 (d, J=7.6 Hz, 2H), 4.87-4.47 (m, 2H), 3.65-3.54 (m, 2H), 3.02 (ddd, J=24.8, 17.4, 12.7 Hz, 1H), 2.48 (ddd, J=17.5, 9.9, 3.6 Hz, 1H), 2.31 (p, J=7.8, 7.1 Hz, 1H), 2.24 (s, 3H), 2.14-2.09 (m, 6H), 1.12 (dd, J=12.8, 7.0 Hz, 3H), 0.92 (s, 9H); Mass (M+H): 375, LCMS Purity: 97.80%.

Preparation of a Compound of Formula 21-15

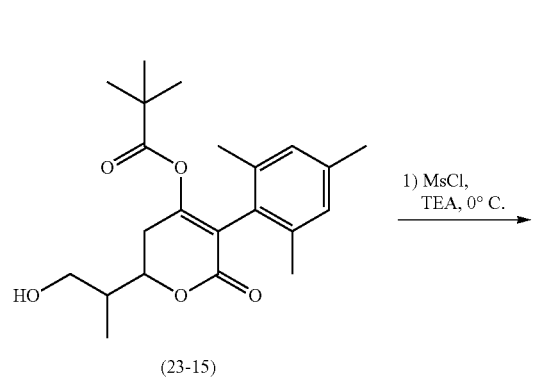

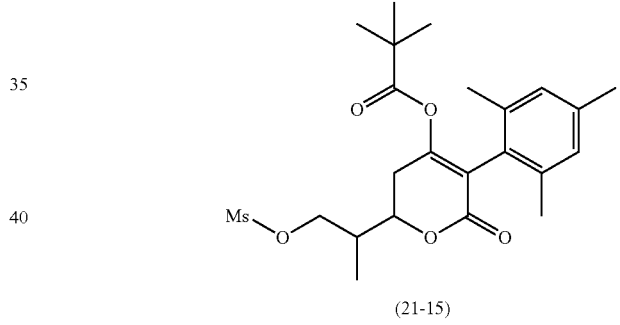

(21-15)

To a solution of 2-(1-hydroxypropan-2-yl)-5-mesityl-6-oxo-3,6-dihydro-2H-pyran-4-yl pivalate (23-15) (10 g, 27.7 mmol) in THF (100 mL) at 0° C. was added Triethylamine (8 mL, 0.554 mmol) followed by the addition of Mesyl chloride (2.7 mL, 34.9 mmol) and the RM was stirred at the same temperature for 2 h. After completion, the RM was poured into ice water, extracted with EtOAc (2 times), EtOAc layer was washed with water, brine, dried over anhydrous Na$_2$SO$_4$, filtered and the solvent was evaporated under reduced pressure to afford 5-mesityl-2-(1-(methylsulfonyloxy)propan-2-yl)-6-oxo-3,6-dihydro-2H-pyran-4-yl pivalate (21-15) as off white solid (11 g, 91%); $^1$H NMR (400 MHz, cdcl$_3$) δ 6.85 (d, J=7.9 Hz, 2H), 4.89-4.57 (m, 1H), 4.47-4.25 (m, 2H), 3.06 (d, J=1.7 Hz, 2H), 2.95 (dd, J=17.6, 12.0 Hz, 1H), 2.56 (ddd, J=57.4, 17.4, 3.8 Hz, 2H), 2.42-2.28 (m, 1H), 2.25 (s, 3H), 2.10 (d, J=2.6 Hz, 6H), 1.19 (dd, J=7.0, 3.1 Hz, 3H), 0.93 (d, J=1.5 Hz, 9H); Mass (M+H): 453, LCMS Purity: 92.91%.

Preparation of a Compound of Formula 1-15

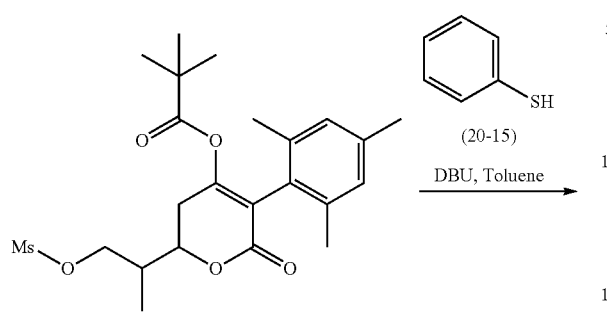

To a solution of 5-mesityl-2-(1-(methylsulfonyloxy)propan-2-yl)-6-oxo-3,6-dihydro-2H-pyran-4-yl pivalate (21-15) (0.639 mmol) and compound of formula (20-15) (1.27 mmol) in toluene (9 mL) was added solution DBU (1.923 mmol) as drop wise and stirred at RT for 2 h. After completion, the RM was poured into water, acidified with 1N HCl, extracted with EtOAc (2 times), EtOAc layer was washed with water, brine, dried over anhydrous $Na_2SO_4$, filtered and the solvent was evaporated under reduced pressure to get crude Compound (1-15). The crude compound was purified by silica gel (100-200 mesh) column chromatography, eluted with 20% EtOAc/pet ether to afford Compound (1-15).

off white solid (24%): $^1$H NMR (400 MHz, cdcl$_3$) δ 7.38 (dd, J=10.5, 7.7 Hz, 2H), 7.34-7.27 (m, 3H), 6.95 (d, J=5.1 Hz, 2H), 5.50 (s, 1H), 4.80-4.46 (m, 1H), 3.32 (ddd, J=24.7, 13.3, 5.9 Hz, 1H), 3.01-2.69 (m, 2H), 2.44 (ddd, J=46.8, 17.1, 3.7 Hz, 1H), 2.29 (s, 3H), 2.12 (d, J=4.6 Hz, 7H), 1.21-1.17 (dd, 3H); Mass (M–H): 381, HPLC Purity: 99.04%.

The present compound as shown below was prepared according to a process of Preparation example 1-3 using 4-fluorophenylthiophenol instead of a compound of formula (20-15).

Compound of Formula 1-19

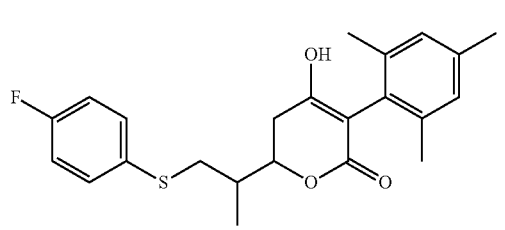

off white solid (56%): $^1$H NMR (400 MHz, cdcl$_3$) δ 7.39 (ddd, J=9.2, 7.9, 5.2 Hz, 2H), 7.05-6.92 (m, 4H), 5.56 (s, 1H), 4.75-4.42 (m, 1H), 3.34-3.18 (m, 1H), 2.94-2.67 (m, 2H), 2.44 (ddd, J=49.5, 17.2, 3.7 Hz, 1H), 2.29 (s, 3H), 2.11 (d, J=6.2 Hz, 6H), 2.01 (dd, J=6.9, 3.5 Hz, 1H), 1.19 (dd, J=16.0, 6.9 Hz, 3H); Mass (M+H): 401, HPLC Purity: 97.91%.

The present compound as shown below was prepared according to a process of Preparation example 1-3 using 4-chlorophenylthiophenol instead of a compound of formula (20-15).

Compound of Formula 1-18

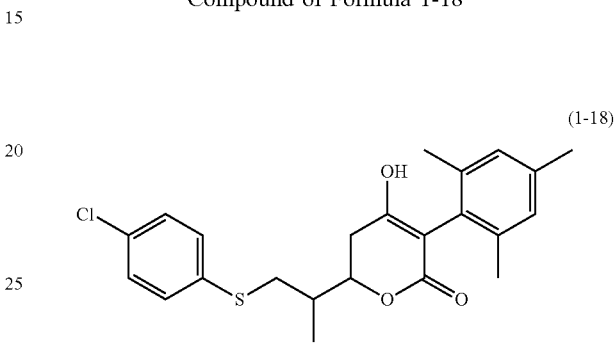

off white solid (25%): $^1$H NMR (300 MHz, cdcl$_3$) δ 7.37-7.26 (m, 4H), 6.95 (d, J=2.9 Hz, 2H), 5.61 (s, 1H), 4.79-4.38 (m, 1H), 3.41-3.21 (m, 1H), 3.00-2.67 (m, 2H), 2.54 (d, J=3.8 Hz, 1H), 2.29 (s, 3H), 2.11 (d, J=2.4 Hz, 7H), 1.25-1.14 (m, 3H); Mass (M+H): 417, HPLC Purity: 95.66%.

The present compound as shown below was prepared according to a process of Preparation example 1-3 using 4-bromophenylthiophenol instead of a compound of formula (20-15).

Compound of Formula 1-68

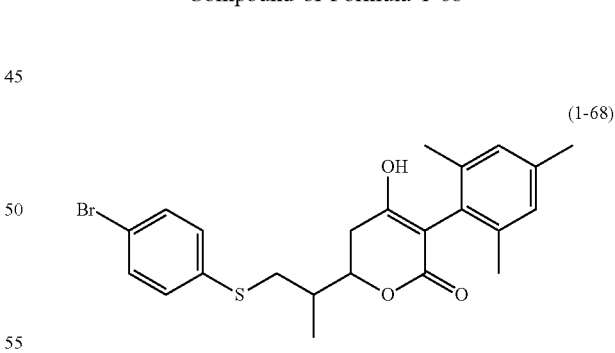

off white solid (40%): $^1$H NMR (300 MHz, cdcl$_3$) δ 7.41 (dt, J=8.3, 1.7 Hz, 2H), 7.23 (dd, J=8.6, 2.1 Hz, 2H), 6.95 (d, J=3.1 Hz, 2H), 5.73 (s, 1H), 4.79-4.65 (m, 1H), 3.49-3.21 (m, 1H), 3.00-2.65 (m, 2H), 2.52-2.37 (dd, J=17.2, 3.5 Hz, 1H), 2.29 (d, J=1.8 Hz, 3H), 2.12 (t, J=2.0 Hz, 6H), 2.08-1.99 (m, 1H), 1.28-1.14 (m, 3H); Mass (M–H): 459, HPLC Purity: 93.23%.

The present compound as shown below was prepared according to a process of Preparation example 1-3 using p-tolylthiophenol instead of a compound of formula (20-15).

Compound of Formula 1-16

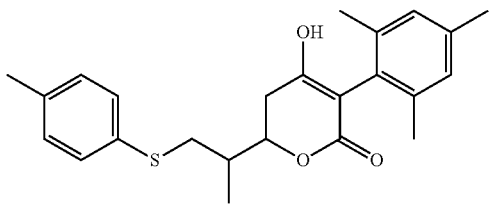

(1-16)

off white solid (53%): ¹H NMR (400 MHz, cdcl₃) δ 7.33-7.27 (m, 2H), 7.11 (d, J=7.7 Hz, 2H), 6.95 (d, J=4.6 Hz, 2H), 5.53 (s, 1H), 4.74 (d, J=13.1 Hz, 1H), 4.55-4.46 (m, 1H), 3.32-3.19 (m, 1H), 2.97-2.68 (m, 1H), 2.42 (ddd, J=41.6, 17.2, 3.7 Hz, 1H), 2.30 (d, J=12.2 Hz, 6H), 2.12 (d, J=5.8 Hz, 7H), 1.19 (dd, J=16.0, 6.8 Hz, 3H); Mass (M+H): 397, HPLC Purity: 97.74%.

The present compound as shown below was prepared according to a process of Preparation example 1-3 using 4-(trifluoromethoxy)phenylthiophenol instead of a compound of formula (20-15).

Compound of Formula 1-39

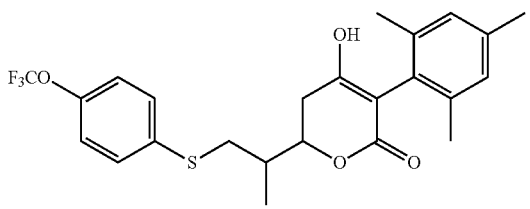

(1-39)

off white solid (59%): ¹H NMR (400 MHz, cdcl₃) δ 7.44-7.35 (m, 2H), 7.15 (d, J=8.2 Hz, 2H), 6.96 (d, J=5.0 Hz, 2H), 4.74-4.47 (ddd, J=11.9, 7.3, 3.8 Hz, 1H), 3.43-3.24 (m, 1H), 2.94 (ddd, J=13.2, 9.2, 7.7 Hz, 1H), 2.88-2.69 (m, 2H), 2.46 (ddd, J=56.1, 17.1, 3.7 Hz, 1H), 2.29 (s, 3H), 2.14-2.10 (m, 7H), 1.20 (dd, J=19.1, 6.9 Hz, 3H); Mass (M−H): 465, HPLC Purity: 99.36%.

The present compound as shown below was prepared according to a process of Preparation example 1-3 using 3-fluorophenylthiophenol instead of a compound of formula (20-15).

Compound of Formula 1-35

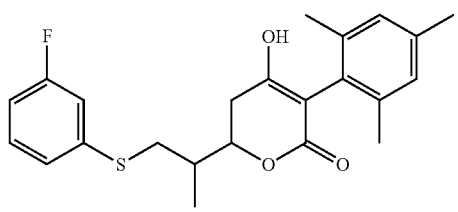

(1-35)

off white solid (49%): ¹H NMR (300 MHz, cdcl₃) δ 7.28 (s, 1H), 7.10 (dt, J=22.4, 9.0 Hz, 2H), 6.91 (dd, J=20.2, 6.3 Hz, 3H), 5.76 (s, 1H), 4.61 (ddt, J=76.1, 12.4, 3.5 Hz, 1H), 3.33 (dd, J=26.2, 13.2, 5.5 Hz, 1H), 2.95 (ddd, J=15.6, 7.1, 3.3 Hz, 1H), 2.88-2.67 (m, 1H), 2.44 (dd, J=40.6, 17.1, 3.7 Hz, 1H), 2.28 (s, 3H), 2.12 (d, J=3.3 Hz, 7H), 1.20 (dd, J=14.6, 6.7 Hz, 3H); Mass (M+H): 401, HPLC Purity: 98.05%.

The present compound as shown below was prepared according to a process of Preparation example 1-3 using 3-chlorophenylthiophenol instead of a compound of formula (20-15).

Compound of Formula 1-88

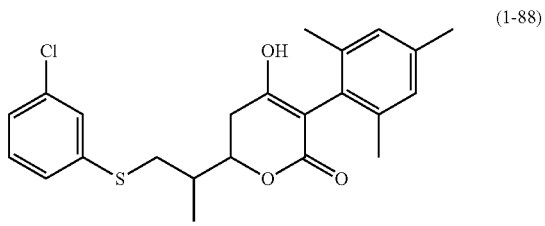 [SMILES: Cc1cc(C)c(C2=C(O)CC(C(C)CSc3cccc(Cl)c3)OC2=O)c(C)c1]

(1-88)

off white solid (43%): ¹H NMR (300 MHz, cdcl₃) δ 7.37-7.27 (m, 1H), 7.23 (d, J=5.5 Hz, 2H), 7.20-7.10 (m, 1H), 6.95 (d, J=3.4 Hz, 2H), 5.70 (s, 1H), 4.60 (ddt, J=79.0, 11.2, 3.7 Hz, 1H), 3.33 (ddd, J=24.3, 13.2, 5.7 Hz, 1H), 3.02-2.89 (m, 1H), 2.89-2.68 (m, 1H), 2.45 (dd, J=39.9, 17.2, 3.7 Hz, 1H), 2.29 (s, 3H), 2.12 (d, J=3.2 Hz, 6H), 2.06 (s, 1H), 1.20 (dd, J=14.5, 6.8 Hz, 3H); Mass (M+H): 416, HPLC Purity: 95.14%.

The present compound as shown below was prepared according to a process of Preparation example 1-3 using m-tolyithiophenol instead of a compound of formula (20-15).

Compound of Formula 1-97

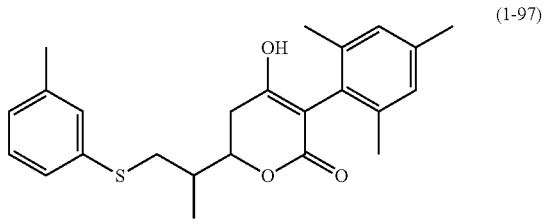 [SMILES: Cc1cccc(SCC(C)C2CC(O)=C(c3c(C)cc(C)cc3C)C(=O)O2)c1]

(1-97)

white solid (61%): ¹H NMR (300 MHz, cdcl₃) δ 7.19 (td, J=7.5, 6.2, 1.9 Hz, 3H), 6.97 (dd, J=12.8, 4.6 Hz, 3H), 5.49 (s, 1H), 4.80-4.45 (m, 1H), 3.29 (td, J=13.9, 13.3, 5.9 Hz, 1H), 2.99-2.87 (m, 1H), 2.87-2.69 (m, 1H), 2.44 (ddd, J=34.6, 17.9, 4.5 Hz, 1H), 2.33 (s, 6H), 2.28 (s, 6H), 2.05 (dd, J=7.1, 3.5 Hz, 1H), 1.20 (dd, J=13.5, 6.8 Hz, 3H); Mass (M+H): 397, HPLC Purity: 99.47%.

The present compound as shown below was prepared according to a process of Preparation example 1-3 using o-tolylthiophenol instead of a compound of formula (20-15).

Compound of Formula 1-86

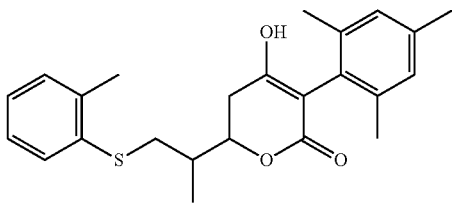

off white solid (44%): ¹H NMR (400 MHz, cdcl₃) δ 7.34 (dd, J=20.2, 7.7 Hz, 2H), 7.20-7.07 (m, 2H), 6.96 (d, J=5.1 Hz, 2H), 5.54 (s, 1H), 4.75-4.4 (m, 1H), 3.23 (d, J=6.7 Hz, 1H), 2.98-2.70 (m, 2H), 2.51 (dd, J=17.0, 3.9 Hz, 1H), 2.44-2.38 (m, 3H), 2.29 (s, 3H), 2.13 (dd, J=5.4, 2.7 Hz, 7H), 1.23 (dd, J=16.5, 6.8 Hz, 3H); Mass (M+H): 397, HPLC Purity: 97.13%.

The present compound as shown below was prepared according to a process of Preparation example 1-3 using 2-chlorophenylthiophenol instead of a compound of formula (20-15).

Compound of Formula 1-84

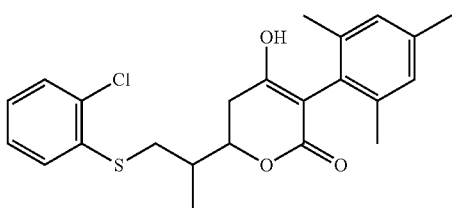

off white solid (51%): ¹H NMR (400 MHz, cdcl₃) δ 7.44-7.34 (m, 2H), 7.23 (dd, J=7.8, 1.4 Hz, 1H), 7.16-7.09 (m, 1H), 6.95 (d, J=5.2 Hz, 2H), 5.57 (s, 1H), 4.84-4.44 (m, 1H), 3.45-3.24 (m, 1H), 3.02-2.69 (m, 2H), 2.48 (ddd, J=54.9, 17.1, 3.7 Hz, 1H), 2.29 (s, 3H), 2.13 (t, J=2.5 Hz, 6H), 2.11-2.04 (m, 1H), 1.24 (dd, J=15.8, 6.9 Hz, 3H); Mass (M+H): 417, HPLC Purity: 98.57%.

The present compound as shown below was prepared according to a process of Preparation example 1-3 using 3,5-difluorophenylthiophenol instead of compound of formula (20-15).

Compound of Formula 1-37

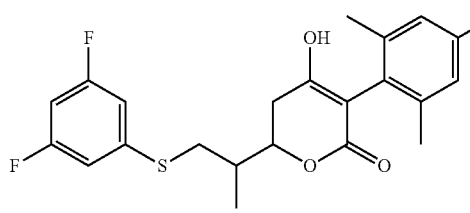

off white solid (18%): ¹H NMR (400 MHz, cdcl₃) δ 6.96 (d, J=5.2 Hz, 2H), 6.92-6.79 (m, 2H), 6.61 (ddd, J=8.8, 7.6, 2.2 Hz, 1H), 5.60 (s, 1H), 4.79-4.41 (m, 1H), 3.45-3.23 (m, 1H), 3.03-2.71 (m, 2H), 2.47 (ddd, J=59.1, 17.1, 3.7 Hz, 1H), 2.29 (s, 3H), 2.27 (s, 1H), 2.13 (t, J=2.6 Hz, 6H), 2.10 (s, 1H), 1.27-1.16 (m, 3H); Mass (M+H): 419, HPLC Purity: 98.08%.

The present compound as shown below was prepared according to a process of Preparation example 1-3 using 3,4-difluorophenylthiophenol instead of a compound of formula (20-15).

Compound of Formula 1-36

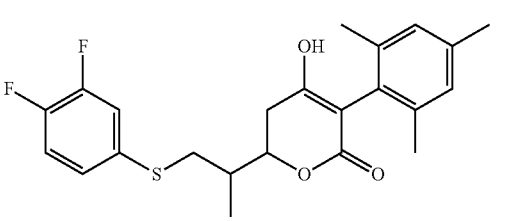

Brown solid (69%): ¹H NMR (300 MHz, cdcl₃): δ 7.25-7.03 (m, 3H), 6.95 (d, J=3.1 Hz, 2H), 5.75 (brs, 1H), 4.72 (dt, J=13.2, 3.4 Hz, 1H), 4.52-4.31 (m, 1H), 3.44-3.17 (m, 1H), 2.97-2.67 (m, 3H), 2.63-2.36 (m, 1H), 2.32-1.94 (m, 8H), 1.31-0.95 (m, 3H); Mass (M+H): 419, HPLC Purity: 98.82%.

The present compound as shown below was prepared according to a process of Preparation example 1-3 using 6-(trifluoromethyl)pyridin-3-ylthiophenol instead of a compound of formula (20-15).

Compound of Formula 1-79

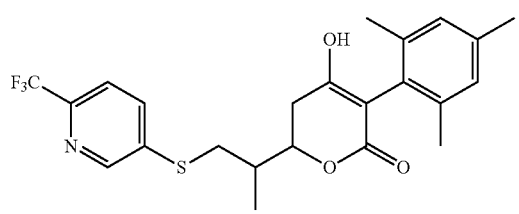

white solid (50%). ¹H NMR (300 MHz, cdcl₃) δ 8.63 (d, J=5.5 Hz, 1H), 7.83 (dd, J=15.7, 8.2 Hz, 1H), 7.60 (d, J=8.4 Hz, 1H), 6.96 (d, J=4.1 Hz, 2H), 5.59 (s, 1H), 4.74-4.41 (m, 1H), 3.61-3.34 (m, 1H), 3.10-2.92 (m, 1H), 2.92-2.67 (m, 2H), 2.65-2.31 (m, 1H), 2.29 (s, 3H), 2.17-2.06 (m, 6H), 1.30-1.16 (m, 3H); Mass (M+H): 452, HPLC Purity: 97.15%.

The present compound as shown below was prepared according to a process of Preparation example 1-3 using methylthiophenol instead of a compound of formula (20-15).

Compound of Formula 1-98

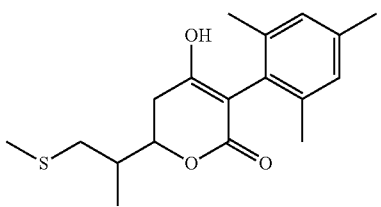

Brown solid (33%). $^1$H NMR (300 MHz, cdcl$_3$) δ 6.96 (d, J=3.7 Hz, 2H), 4.78-4.47 (m, 1H), 2.93-2.69 (m, 2H), 2.61-2.38 (m, 2H), 2.29 (m, 4H), 2.17 (m, 10H), 1.17 (dd, J=15.2, 6.9 Hz, 3H); Mass (M+H): 321, HPLC Purity: 95.55%.

The present compound as shown below was prepared according to a process of Preparation example 1-3 using ethylthiophenol instead of a compound of formula (20-15).

Compound of Formula 1-99

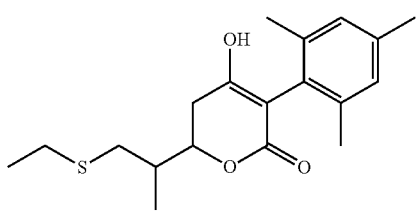

off white solid (28%): $^1$H NMR (300 MHz, cdcl$_3$) δ 6.96 (d, J=3.9 Hz, 2H), 5.59 (s, 1H), 4.72-4.53 (m, 1H), 2.94-2.69 (m, 2H), 2.57 (ddt, J=10.8, 7.2, 3.1 Hz, 3H), 2.51-2.37 (m, 1H), 2.29 (s, 3H), 2.14 (d, J=6.1 Hz, 7H), 1.28 (td, J=7.3, 1.2 Hz, 3H), 1.17 (dd, J=16.8, 6.8 Hz, 3H); Mass (M+H): 335, HPLC Purity: 95.08%.

The present compound as shown below was prepared according to a process of Preparation example 1-3 using propylthiophenol instead of a compound of formula (20-15).

Compound of Formula 1-100

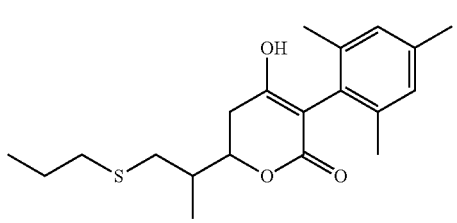

off white solid (22%): $^1$H NMR (300 MHz, cdcl$_3$) δ 6.96 (d, J=3.8 Hz, 2H), 5.52 (s, 1H), 4.78-4.47 (m, 1H), 2.93-2.69. (m, 2H), 2.64-2.39 (m, 5H), 2.29 (s, 3H), 2.14 (d, J=6.1 Hz, 6H), 1.63 (q, J=7.3 Hz, 2H), 1.17 (dd, J=16.4, 6.9 Hz, 3H), 1.00 (t, J=7.3 Hz, 3H); Mass (M–H): 347, HPLC Purity: 95.38%.

The present compound as shown below was prepared according to a process of Preparation example 1-3 using pyrimidin-2-ylthiol instead of a compound of formula (20-15).

Compound of Formula 1-42

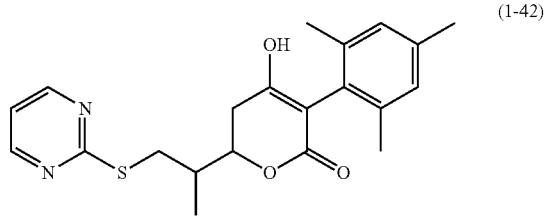 [SMILES: Cc1cc(C)c(C2=C(O)CC(C(C)CSc3ncccn3)OC2=O)c(C)c1]

off white solid (33%): $^1$H NMR (300 MHz, cdcl$_3$) δ 8.52 (dd, J=4.8, 1.2 Hz, 2H), 7.02-6.92 (m, 3H), 5.53 (s, 1H), 4.77-4.61 (d, J=12.6 Hz, 1H), 3.65-3.39 (m, 1H), 3.21 (dd, J=21.8, 13.8, 7.4 Hz, 1H), 2.99-2.84 (m, 1H), 2.64-2.39 (m, 1H), 2.29 (s, 3H), 2.14 (d, J=2.0 Hz, 6H), 1.24 (dd, J=14.6, 6.8 Hz, 3H); Mass (M+H): 385, HPLC Purity: 95.06%.

The present compound as shown below was prepared according to a process of Preparation example 1-3 using thiophen-2-ylthiol instead of a compound of formula (20-15).

Compound of Formula 1-90

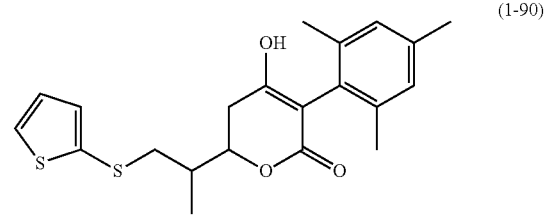 [SMILES: Cc1cc(C)c(C2=C(O)CC(C(C)CSc3cccs3)OC2=O)c(C)c1]

Brown solid (55%): $^1$H NMR (300 MHz, cdcl$_3$) δ 7.34 (s, 1H), 7.15 (d, J=4.3 Hz, 1H), 6.96 (s, 3H), 5.52 (s, 1H), 4.81-4.47 (m, 1H), 3.25-3.07 (m, 1H), 2.92-2.66 (m, 2H), 2.42 (t, J=19.0 Hz, 1H), 2.28 (s, 3H), 2.13 (dd, J=10.4, 4.4 Hz, 7H), 1.20 (dd, J=7.1, 3.0 Hz, 3H); Mass (M+H): 389, HPLC Purity: 93.57%.

The present compound as shown below was prepared according to a process of Preparation example 1-3 using oxazol-2-ylthiol instead of a compound of formula (20-15).

Compound of Formula 1-102

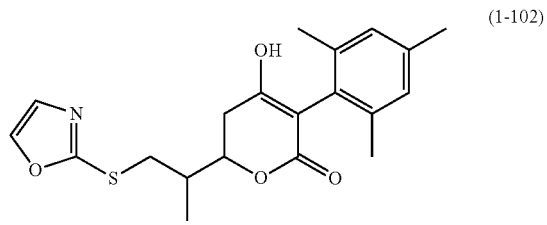 [SMILES: Cc1cc(C)c(C2=C(O)CC(C(C)CSc3ncco3)OC2=O)c(C)c1]

off white solid (50%): ¹H NMR (300 MHz, cdcl₃) δ 7.69-7.65 (m, 1H), 7.09, (s, 1H), 6.96 (s, 2H), 5.59 (s, 1H), 4.84-4.48 (m, 1H), 3.65-3.40 (m, 1H), 3.23 (dt, J=13.5, 8.0 Hz, 1H), 2.88 (td, J=16.4, 12.8 Hz, 2H), 2.61-2.32 (m, 3H), 2.29 (s, 6H), 2.18-2.10 (m, 1H), 1.22 (dd, J=13.6, 7.0 Hz, 3H); Mass (M+H): 374, HPLC Purity: 98.10%.

The present compound as shown below was prepared according to a process of Preparation example 1-3 using thiazol-2-ylthiol instead of a compound of formula (20-15).

Compound of Formula 1-91

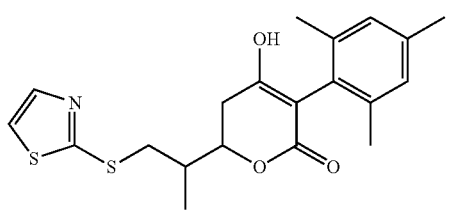

(1-91)

off white solid (23%): ¹H NMR (400 MHz, cdcl₃) δ 7.65 (d, J=3.4 Hz, 1H), 7.22 (dd, J=3.4, 1.9 Hz, 1H), 6.95 (d, J=3.7 Hz, 2H), 5.62 (d, J=24.8 Hz, 1H), 4.83-4.50 (m, 1H), 3.66-3.51 (m, 1H), 3.27 (ddd, J=19.6, 13.5, 7.3 Hz, 1H), 2.87 (ddd, J=20.1, 17.2, 13.0 Hz, 1H), 2.50-2.32 (m, 1H), 2.28 (s, 3H), 2.25 (d, J=3.7 Hz, 1H), 2.18-2.11 (m, 6H), 1.23 (dd, J=13.6, 6.9 Hz, 3H); Mass (M+H): 390, HPLC Purity: 99.13%.

The present compound as shown below was prepared according to a process of Preparation example 1-3 using 1,3,4-thiadiazol-2-ylthiol instead of a compound of formula (20-15).

Compound of Formula 1-103

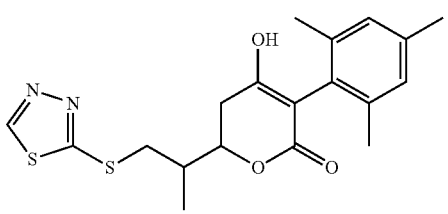

(1-103)

white solid (38%)¹H NMR (300 MHz, cdcl₃) δ 9.00 (dd, J=3.4, 1.5 Hz, 1H), 6.96 (s, 2H), 5.73 (d, J=11.1 Hz, 1H), 4.80 (d, J=12.5 Hz, 1H), 3.75 (ddd, J=63.5, 13.4, 5.4 Hz, 1H), 3.41 (ddd, J=28.3, 13.4, 7.5 Hz, 1H), 3.07-2.80 (m, 1H), 2.68-2.37 (m, 2H), 2.29 (s, 3H), 2.20-2.08 (m, 6H), 1.32-1.20 (m, 3H); Mass (M+H): 391, HPLC Purity: 95.43%.

The present compound as shown below was prepared according to a process of Preparation example 1-3 using cyclohexylthiol instead of a compound of formula (20-15).

Compound of Formula 1-105

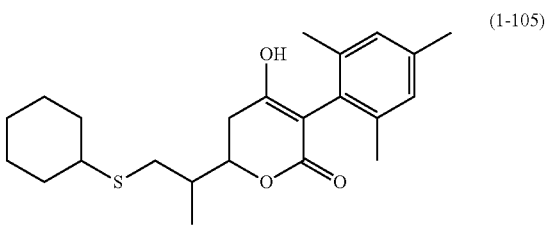 [SMILES: Cc1cc(C)c(C2=C(O)CC(C(C)CSC3CCCCC3)OC2=O)c(C)c1]

(1-105)

white solid (22%): ¹H NMR (400 MHz, cdcl₃) δ 6.96 (d, J=5.5 Hz, 2H), 5.54 (s, 1H), 4.76-4.48 (m, 1H), 2.92-2.80 (m, 2H), 2.61 (tdd, J=12.7, 7.7, 5.2 Hz, 2H), 2.47 (ddd, J=32.0, 17.1, 3.7 Hz, 1H), 2.29 (s, 3H), 2.15 (d, J=8.0 Hz, 7H), 1.99 (dd, J=8.4, 5.2 Hz, 3H), 1.77 (s, 2H), 1.62 (d, J=10.3 Hz, 1H), 1.40-1.23 (m, 5H), 1.19 (d, J=6.8 Hz, 2H); Mass (M+H): 389, HPLC Purity: 95.87%.

Preparation Example 1-4

Preparation of a Compound of Formula (1-106)

Preparation of a Compound of 3-(4-(trifluoromethyl)phenoxy)propan-1-ol

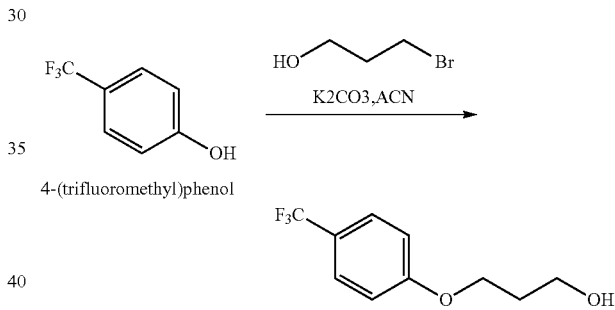

4-(trifluoromethyl)phenol

To a solution of 4-(trifluoromethyl) phenol (3 g, 18.50 mmol) in ACN (50 mL) was added K₂CO₃ (7.6 g, 55.50 mmol), followed by the addition of 3-bromo phenol (3 g, 22.20 mmol) and stirred the reaction at RT for 16 h. After completion, the RM was poured into water, extracted with EtOAc (2 times), EtOAc layer was washed with water, brine, dried over anhydrous Na₂SO₄, filtered and the solvent was evaporated under reduced pressure to get crude product. The crude compound was purified by silica gel (100-200 mesh) column chromatography, eluted with 20% EtOAc/pet ether to afford 3-(4-(trifluoromethyl)phenoxy)propan-1-ol as oily mass (3.0 g, 75%); ¹H NMR (300 MHz, cdcl₃) δ 7.54 (d, J=8.4 Hz, 2H), 6.97 (d, J=8.4 Hz, 2H), 4.17 (t, J=6.0 Hz, 2H), 3.87 (p, J=6.7, 6.2 Hz, 2H), 2.15-2.00 (m, 2H).

Preparation of a Compound of 3-(4-(trifluoromethyl)phenoxy)propanal

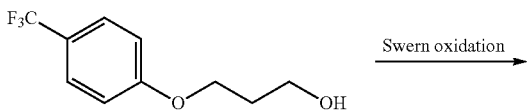

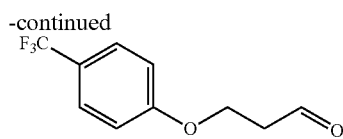

To a solution dimethyl sulfoxide (2.8 mL, 40.53 mmol) in dichloromethane (30 mL) was added oxalyl chloride (1.75 mL, 20.40 mmol) at −78° C. and stirred the reaction mixture for 30 min. at the same temperature the solution of 3-(4-(trifluoromethyl)phenoxy)propan-1-ol (3 g, 13.51 mmol) in dry dichloromethane (30 mL) was added to the reaction mixture and stirred for 30 min. Followed by the addition of triethyl amine (7.5 mL, 53.46 mmol) at −78° C. and stirred at RT for 1 h. After completion, the RM was poured into water, extracted with DCM (2 times), DCM layer was washed with water, brine, dried over anhydrous $Na_2SO_4$, filtered and evaporated under reduced pressure to get crude product. The crude compound was purified by silica gel (100-200 mesh) column chromatography, eluted with 5% EtOAc/pet ether to afford 3-(4-(trifluoromethyl)phenoxy)propanal as oily mass (1.5 g, reasonable pure); $^1$H NMR (400 MHz, cdcl$_3$) δ 9.88 (t, J=1.4 Hz, 1H), 7.63-7.44 (m, 2H), 6.93-6.87 (m, 2H), 4.35 (t, J=6.1 Hz, 2H), 2.95 (td, J=6.1, 1.4 Hz, 2H).

Preparation of a Compound of Methyl 5-hydroxy-2-mesityl-3-oxo-7-(4-(trifluoromethyl)phenoxy)heptanoate

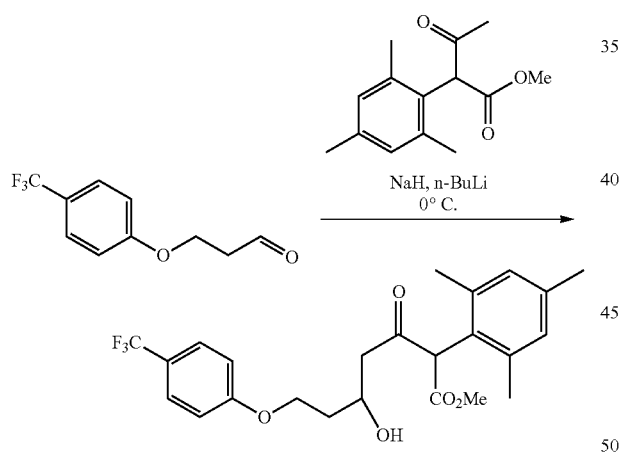

To a suspension of NaH (256 mg, 6.41 mmoles) in THF (5 mL) was added the solution of Methyl 2-mesityl-3-oxobutanoate (500 mg, 2.13 mmoles) in THF (5 mL) at 0° C. and stirred for 30 min. and cooled to −40° C. followed by the addition of n-BuLi (5.3 mL, 8.54 mmoles) and stirred for 30 min. followed by the addition of solution of 3-(4-(trifluoromethyl)phenoxy)propanal (1.5 g, 6.41 mmoles) in THF (2 mL) at −40° C. and stirred for 30 min. Reaction did not go completion, hence, the RM was quenched with saturated ammonium chloride solution at 0° C., extracted with EtOAc (2 times), EtOAc layer was washed with water, brine, dried over anhydrous $Na_2SO_4$, filtered and the solvent was evaporated under reduced pressure to get crude product. The crude compound was purified by silica gel (100-200 mesh) column chromatography, eluted with 10% EtOAc/pet ether to afford methyl 5-hydroxy-2-mesityl-3-oxo-7-(4-(trifluoromethyl)phenoxy)heptanoate as oily mass (260 mg, LCMS purity: 45%).; $^1$H NMR (400 MHz, cdcl$_3$) δ13.35 (d, J=1.1 Hz, 1H), 7.53 (td, J=6.8, 2.8 Hz, 2H), 7.00-6.76 (m, 4H), 4.37 (dd, J=7.2, 1.0 Hz, 2H), 3.69 (d, J=1.1 Hz, 3H), 2.28 (d, J=5.2 Hz, 3H), 2.24-2.14 (m, 2H), 2.20-2.14 (m, 2H), 2.08 (d, J=9.7 Hz, 6H), 1.86-1.82 (m, 2H); Mass (M+H): 451; LCMS Purity: 45.56%; Mass (M−H): 451, LCMS Purity: 45.56%.

Preparation of a Compound of Formula 1-106

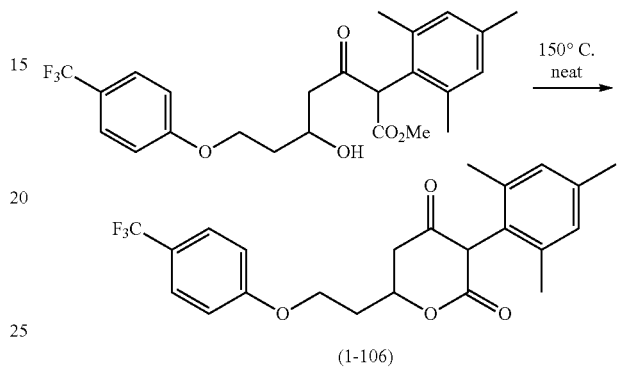

The methyl 5-hydroxy-2-mesityl-3-oxo-7-(4-(trifluoromethyl)phenoxy)heptanoate (260 mg, 0.57 mmoles) was heated to 150° C. for 3 h. After completion, the RM was poured into ice water, extracted with EtOAc (2 times), EtOAc layer was washed with water, brine, dried over anhydrous $Na_2SO_4$, filtered and evaporated under reduced pressure to get crude compound. The crude compound was purified by silica gel (100-200 mesh) column chromatography, eluted with 7% EtOAc/pet ether to afford 3-mesityl-6-(2-(4-(trifluoromethyl)phenoxy)ethyl)dihydro-2H-pyran-2,4(3H)-dione (1-106) as white solid (75 mg; 15.3%; over all yield for step-3 &4); $^1$H NMR (300 MHz, cdcl$_3$) δ 7.56 (d, J=8.4 Hz, 2H), 7.04-6.92 (m, 4H), 6.4-5.0 (br s, 1H), 4.84 (d, J=4.1 Hz, 1H), 4.29 (dd, J=23.4, 5.0 Hz, 2H), 2.84 (dd, J=17.2, 12.0 Hz, 1H), 2.65 (dd, J=17.3, 4.0 Hz, 1H), 2.29 (s, 5H), 2.14 (d, J=3.7 Hz, 6H); Mass (M+H): 421, HPLC Purity: 95.06%.

Preparation Example 1-5

Preparation of a Compound of Formula (1-107)

Preparation of a Compound of 4-(phenylthio)butan-1-ol

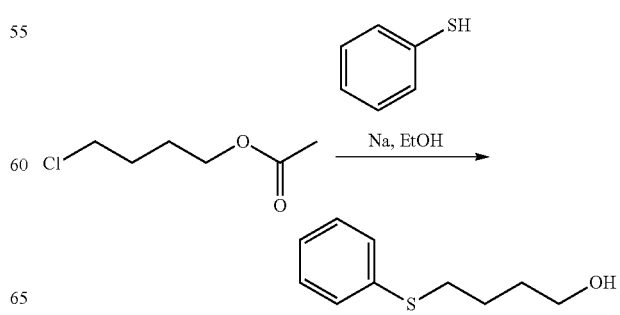

To a suspension of sodium ethoxide (4 g, 59.18 mmol) in EtOH (50 mL) was added thiophenol (5 g, 45.45 mmol) at 0° C., followed by drop-wise addition of 4-chlorobutyl acetate (7 g, 45.45 mmol) over a period of 20 min. and stirred the same temperature for 10 min. and heated at reflux for 6 h. The RM was cooled the reaction to RT, added KOH pellets (2.6 g, 45.45 mmol), heated at reflux for 4 h. After completion, the RM was poured into ice water, extracted with EtOAc (2 times), EtOAc layer was washed with water, brine, dried over anhydrous $Na_2SO_4$, filtered and the solvent was evaporated under reduced pressure to get crude compound. The crude compound was purified by silica gel (60-120 mesh) column chromatography, eluted with 8% EtOAc/pet ether to afford 4-(phenylthio)butan-1-ol as oily mass (6 g, 72%); $^1$H NMR (400 MHz, cdcl$_3$) δ 7.33 (dd, J=8.2, 1.6 Hz, 2H), 7.30-7.23 (m, 2H), 7.20-7.14 (m, 1H), 3.65 (td, J=5.0, 4.1, 3.0 Hz, 2H), 2.96 (t, J=6.9 Hz, 2H), 1.78-1.65 (m, 4H); Mass (M+H): 183, LCMS Purity: 99.83%.

Preparation of a Compound of 4-(phenylthio)butanal

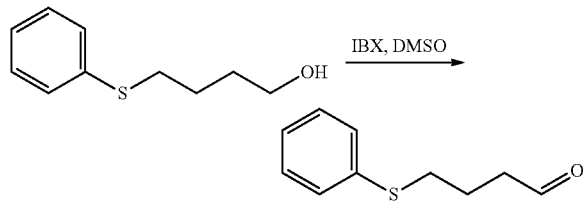

To a solution 4-(phenylthio)butan-1-ol (4 g, 21.9 mmol) in DMSO (20 mL) was 2-Iodoxy benzoic acid (9.32 g, 281 mmol) at RT and stirred at RT for 8 h. After completion, the RM was diluted with EtOAc, filtered to remove the solids, filtrate was extracted with EtOAc (2 times), EtOAc layer was washed with water, brine, dried over anhydrous $Na_2SO_4$, filtered and the solvent was evaporated under reduced pressure to get crude compound. The crude compound was purified by silica gel (100-200 mesh) column chromatography, eluted with 5% EtOAc/pet ether to afford 4-(phenylthio)butanal as colour less liquid (2 g, 52%); $^1$H NMR (400 MHz, cdcl$_3$) δ 9.77 (dt, J=7.2, 1.2 Hz, 1H), 7.37-7.32 (m, 2H), 7.32-7.24 (m, 2H), 7.23-7.14 (m, 1H) 2.97 (dd, J=7.7, 6.4 Hz, 2H), 2.69-2.57 (m, 2H), 1.96 (p, J=7.1 Hz, 2H).

Preparation of a Compound of Methyl 5-hydroxy-2-mesityl-3-oxo-8-(phenylthio)octanoate

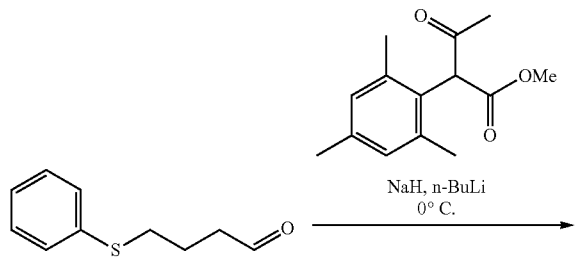

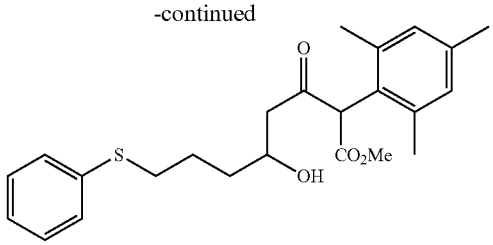

To a suspension of NaH (301 mg, 7.69 mmoles) in THF (10 mL) was added the solution of methyl 2-mesityl-3-oxobutanoate (600 mg, 2.56 mmoles) in THF (10 mL) at 0° C. and stirred for 30 min. and cooled to −40° C. followed by the addition of n-BuLi (6.41 mL, 10.25 mmoles) and stirred for min. followed by the addition of solution of (phenylthio)butanal (1.38 g, 7.69 mmoles) in THF (3 mL) at −40° C. and stirred for 30 min. Reaction did not go completion, hence, the RM was quenched with saturated ammonium chloride solution at 0° C., extracted with EtOAc (2 times), EtOAc layer was washed with water, brine, dried over anhydrous $Na_2SO_4$, filtered and evaporated under reduced pressure to get crude product. The crude compound was purified by silica gel (100-200 mesh) column chromatography, eluted with 25% EtOAc/pet ether to afford methyl 5-hydroxy-2-mesityl-3-oxo-8-(phenylthio)octanoate as oily mass (1.1 g; crude, LCMS purity: 43%).

<Preparation of a Compound of Formula 1-107

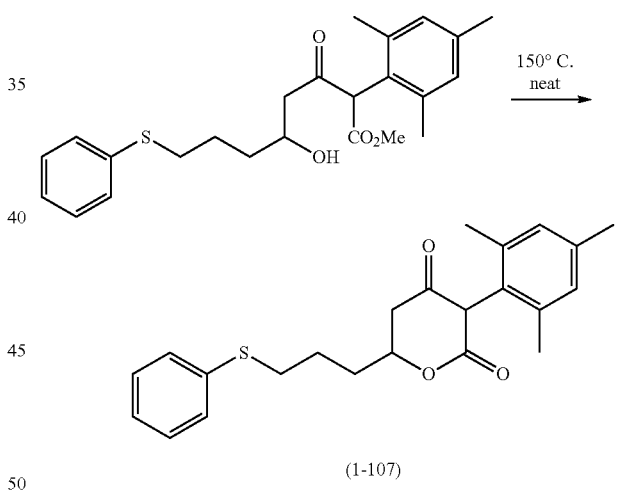

(1-107)

The methyl 5-hydroxy-2-mesityl-3-oxo-8-(phenylthio) octanoate (1.1 g, 2.65 mmoles) was heated to 150° C. for 3 h. After completion, the RM was poured into ice water, extracted with EtOAc (2 times), EtOAc layer was washed with water, brine, dried over anhydrous $Na_2SO_4$, filtered and evaporated under reduced pressure to get crude compound. The crude compound was purified by silica gel (100-200 mesh) column chromatography, eluted with 7% EtOAc/pet ether to afford 3-mesityl-6-(3-(phenylthio)propyl)dihydro-2H-pyran-2,4(3H)-dione (1-107) as off white solid (150 mg; 16.3%; over all yield on step-3 & 4); $^1$H NMR (400 MHz, dmso) δ 10.62 (s, 1H), 7.40-7.12 (m, 5H), 6.80 (d, J=2.8 Hz, 2H), 4.50 (dt, J=7.4, 3.7 Hz, 1H), 3.09-2.95 (m, 2H), 2.70-2.53 (m, 2H), 2.21 (s, 3H), 2.00 (d, J=8.7 Hz, 6H), 1.90-1.65 (m, 4H); Mass (M−H): 381, LCMS Purity: 97.79%.

Preparation Example 1-6

Preparation of a Compound of Formula (1-108)

Preparation of a Compound of 2-(phenylthio)acetaldehyde

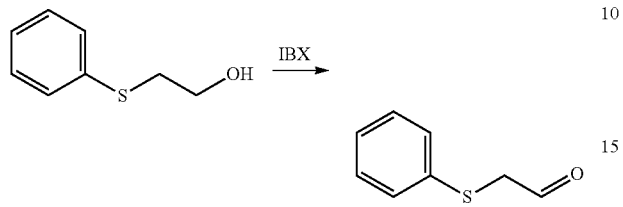

To a solution 2-(phenylthio)ethanol (5 g, 32.46 mmol) in DMSO (25 mL) was added 2-Iodoxy benzoic acid (13.68 g, 48.70 mmol) at RT and stirred at RT for 8 h. After completion, the RM was diluted with EtOAc, filtered to remove the solids, extracted filtrate with EtOAc (2 times), EtOAc layer, was washed with water, brine, dried over anhydrous $Na_2SO_4$, filtered and evaporated under reduced pressure to get crude compound. The crude compound was purified by silica gel (100-200 mesh) column chromatography, eluted with 5% EtOAc/pet ether to afford 2-(phenylthio)acetaldehyde as oily mass (1.8 g yield: 42%); $^1$H NMR (400 MHz, cdcl$_3$) δ9.56 (t, J=3.2 Hz, 1H), 7.40-7.23 (m, 5H), 3.60 (d, J=3.2 Hz, 2H).

Preparation of a Compound of Methyl 5-hydroxy-2-mesityl-3-oxo-6-(phenylthio)hexanoate

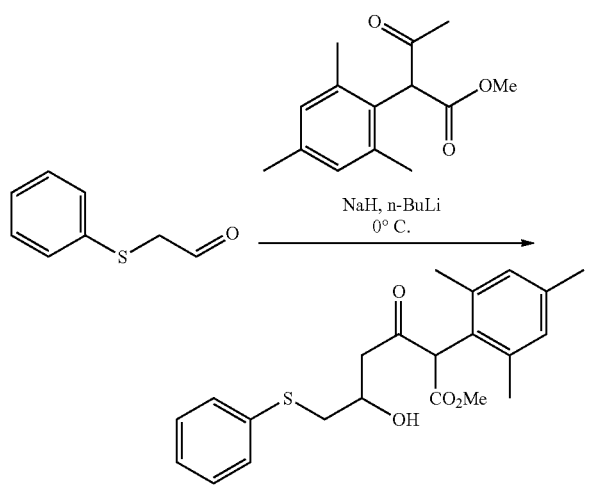

To a suspension of NaH (358 mg, 8.97 moles) in THF (15 mL) was added the solution of methyl 2-mesityl-3-oxobutanoate (700 mg, 2.99 mmoles) in THF (25 mL) at 0° C. and stirred for 30 min. and cooled to −40° C. followed by the addition of n-BuLi (7.4 mL, 11.96 mmoles) and stirred for min. followed by the addition of solution of 2-(phenylthio)acetaldehyde (1.36 mg, 8.97 mmoles) at −40° C. and stirred for 30 min. Reaction did not go completion, hence, the RM was quenched with saturated ammonium chloride solution at 0° C., extracted with EtOAc (2 times), EtOAc layer was washed with water, brine, dried over anhydrous $Na_2SO_4$, filtered and the solvent was evaporated under reduced pressure to get crude product. The crude compound was purified by silica gel (100-200 mesh) column chromatography, eluted with 6% EtOAc/pet ether to afford methyl 5-hydroxy-2-mesityl-3-oxo-6-(phenylthio)hexanoate as oily mass (262 mg, 44%); $^1$H NMR (300 MHz, cdcl$_3$) δ 13.24 (s, 1H), 7.29-7.24 (m, 5H), 6.88 (d, J=6.5 Hz, 2H), 4.03 (s, 1H), 3.68 (d, J=1.2 Hz, 3H), 2.96 (d, J=4.9 Hz, 1H), 2.84 (dd, J=13.7, 7.7 Hz, 1H), 2.76 (d, J=3.5 Hz, 1H), 2.30 (s, 3H), 2.26-2.20 (m, 2H), 2.06 (s, 3H), 2.04 (d, J=14.3 Hz, 3H); Mass (M+H): 387, LCMS Purity: 75.83%.

<Preparation of a Compound of Formula 1-108

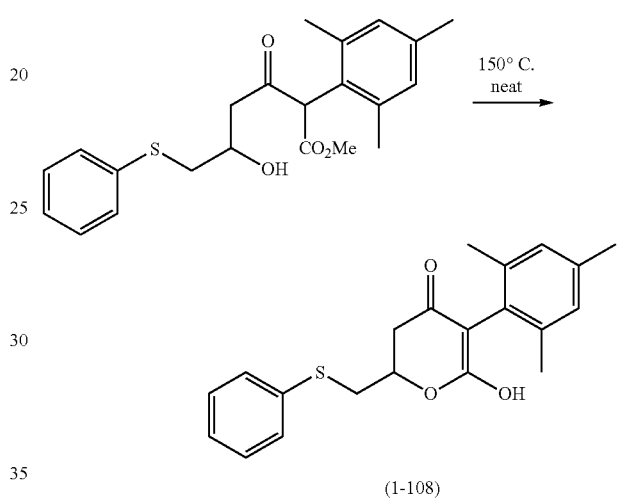

(1-108)

The methyl-5-hydroxy-2-mesityl-3-oxo-6-(phenylthio)hexanoate (260 mg, 0.67 mmoles) was heated to 150° C. for 3 h. After completion, the RM was poured in to ice water, extracted with EtOAc (2 times), EtOAc layer was washed with water, brine, dried over anhydrous $Na_2SO_4$, filtered and the solvent was evaporated under reduced pressure to get crude compound. The crude compound was purified by silica gel (100-200 mesh) column chromatography, eluted with 6% EtOAc/pet ether to afford 6-hydroxy-5-mesityl-2-(phenylthiomethyl)-2H-pyran-4(3H)-one (1-108) as white solid (80 mg, 33%); $^1$H NMR (400 MHz, dmso) δ 10.79 (s, 1H), 7.49-7.15 (m, 5H), 6.80 (d, J=5.2 Hz, 2H), 4.62 (dd, J=10.7, 5.1 Hz, 1H), 3.41 (t, J=5.3 Hz, 2H), 2.89-2.69 (m, 2H), 2.21 (s, 3H), 1.99 (d, J=3.0 Hz, 6H); Mass (M+H): 354.9; HPLC Purity: 95.00%.

Preparation Example 1-7

Preparation of a Compound of Formula (1-109)

Preparation of a Compound of 4-(4-(trifluoromethyl)phenylthio)butan-2-one

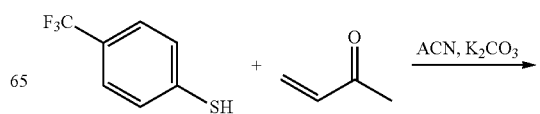

93

-continued

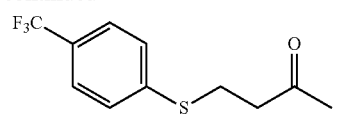

To a solution of 4-(trifluoromethyl)benzenethiol (3 g, 16.83 mmol) in ACN (50 mL) was added $K_2CO_3$ (6.97 g, 50.51 mmol), followed by the addition of methyl vinyl ketone (1.68 mL, 20.20 mmol) and stirred the reaction at RT for 16 h. After completion, the RM was poured into water, extracted with EtOAc (2 times), EtOAc layer was washed with water, brine, dried over anhydrous $Na_2SO_4$, filtered and the solvent was evaporated under reduced pressure to get crude product. The crude compound was purified by silica gel (100-200 mesh) column chromatography, eluted with 5% EtOAc/pet ether to afford 4-(4-(trifluoromethyl)phenylthio)butan-2-one as off white solid (3 g, 74%); $^1$H NMR (300 MHz, cdcl$_3$) δ 7.53 (d, J=8.1 Hz, 2H), 7.36 (d, J=8.1 Hz, 2H), 3.20 (t, J=7.2 Hz, 2H), 2.81 (t, J=7.2 Hz, 2H), 2.18 (s, 3H); Mass (M+H): 249; LCMS Purity: 98.75%.

Preparation of a Compound of Methyl5-hydroxy-2-mesityl-5-methyl-3-oxo-7-(4-(trifluoromethyl)phenylthio)heptanoate

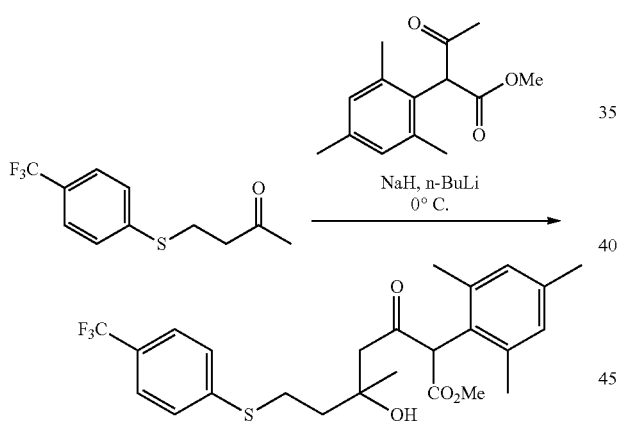

To a suspension of NaH (306 mg, 7.69 mmoles) in THF (15 mL) was added the solution of methyl 2-mesityl-3-oxobutanoate (600 mg, 2.46 mmoles) in THF (15 mL) at 0° C. and stirred for 30 min. and cooled to −40° C. followed by the addition of n-BuLi (6 mL, 10.15 mmoles) and stirred for 30 min. followed by the addition of solution of 4-(4-(trifluoromethyl)phenylthio)butan-2-one (1.8 g, 7.69 mmoles) in THF (2 mL) at −40° C. and stirred for 30 min. After completion, the RM was quenched with saturated ammonium chloride solution at 0° C., extracted with EtOAc (2 times), EtOAc layer was washed with water, brine, dried over anhydrous $Na_2SO_4$, filtered and the solvent was evaporated under reduced pressure to get crude product. The crude compound was purified by silica gel (100-200 mesh) column chromatography, eluted with 25% EtOAc/pet ether to afford methyl 5-hydroxy-2-mesityl-5-methyl-3-oxo-7-(4-(trifluoromethyl)phenylthio)heptanoate (800 mg; LCMS purity: 30%).

94

Preparation of a Compound of Formula 1-109

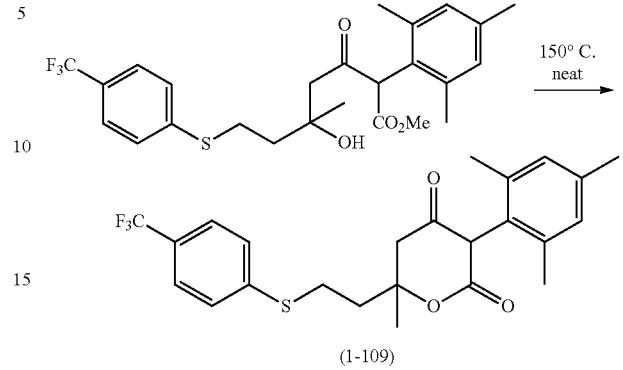

The methyl 5-hydroxy-2-mesityl-5-methyl-3-oxo-7-(4-(trifluoromethyl)phenylthio)heptanoate (900 mg, crude) was heated to 150° C. for 3 h. After completion, the RM was poured into ice water, extracted with EtOAc (2 times), EtOAc layer was washed with water, brine, dried over anhydrous $Na_2SO_4$, filtered and the solvent was evaporated under reduced pressure to get crude compound. The crude compound was purified by silica gel (100-200 mesh) column chromatography, eluted with 7% EtOAc/pet ether to afford 3-mesityl-6-methyl-6-(2-(4-(trifluoromethyl)phenylthio)ethyl)dihydro-2H-pyran-2,4(3H)-dione (1-109) as white solid (110 mg, 10%, overall yield on step-2 & 3); $^1$H NMR (300 MHz, dmso) δ 10.64 (s, 1H), 7.64 (d, J=8.1 Hz, 2H), 7.52 (d, J=8.0 Hz, 2H), 6.79 (d, J=7.5 Hz, 2H), 3.19 (t, J=7.9 Hz, 2H), 2.89 (d, J=17.3 Hz, 1H), 2.66 (d, J=17.5 Hz, 1H), 2.21 (s, 3H), 2.10 (s, 2H), 2.01 (s, 3H), 1.89 (s, 3H), 1.53 (s, 3H); Mass (M+H): 451, HPLC Purity: 97.27%.

Preparation Example 4

Preparation of a Compound of Formula (1-4)

Preparation of a Compound of Formula 16-1

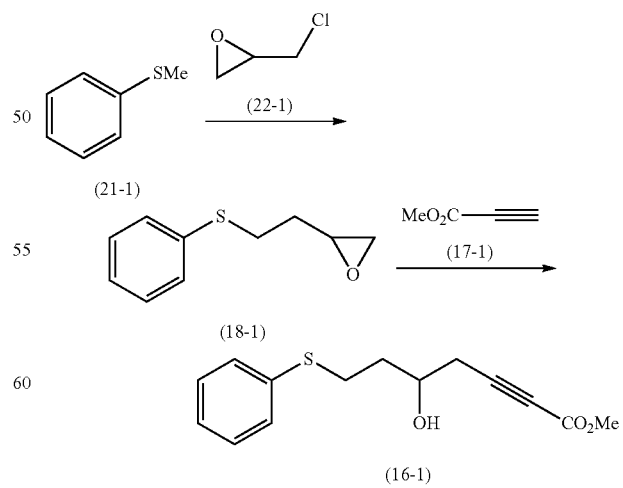

At RT under nitrogen atmosphere, a compound of formula (21-1) 6.2 ml was diluted with dehydrated tetrahydrofuran 50 ml and to the resulting solution was added triethylenediamine 600 mg. The resulting mixed solution was then cooled to 0° C. and thereto was added n-butyl lithium 32 ml (1.6 M hexane solution; 53 mmol, 1.0 eq.) and the resulting mixture was stirred for about 2 hours while the reaction temperature was raised to RT. The resulting mixed solution was then cooled to −78° C. and thereto was then added a compound of formula (22-1) 8.3 ml, and the resulting reaction solution was stirred for about 2 hours while the reaction temperature was raised to RT slowly. To the resulting reaction solution was added aqueous saturated ammonium chloride solution 25 ml and an aqueous layer was extracted with chloroform. The obtained chloroform layer was washed with saturated saline and dried over anhydrous $Na_2SO_4$ and filtered, and the obtained filtrate was concentrated under reduced pressure and purified by column chromatography using ($SiO_2$) by eluting EtOAc:hexane (1:4) to afford a compound of formula (18-1) 3.27 g.

Successively, at RT under nitrogen atmosphere, a compound of formula (17-1) 2.4 ml was diluted with dehydrated tetrahydrofuran 35 ml and the resulting solution was cooled to −78° C. and thereto was then added n-butyl lithium 16.3 ml (1.6 M hexane solution), and the resulting mixture was stirred at the same temperature for about 10 minutes. To the resulting reaction solution was then added at the same temperature boron trifluoride diethyl ether complex 3.6 ml, and the resulting mixture was stirred at the same temperature for about 10 minutes. To the resulting solution was then added at the same temperature a solution of a compound of formula (18-1) 3.27 g in dehydrated tetrahydrofuran 10 ml drop wise and the resulting mixture was stirred for about 30 minutes. To the resulting reaction solution was added aqueous saturated ammonium chloride solution 30 ml and the aqueous layer was extracted with ethyl acetate. The resulting ethyl acetate layer was dried over anhydrous $Na_2SO_4$ and filtered, and the resulting filtrate was purified by column chromatography using ($SiO_2$) by eluting EtOAc:hexane (1:3) to afford a compound of formula (16-1) 2.67 g (yield 56%).

$^1$H NMR ($CDCl_3$)

δ ppm: 7.35-7.32 (2H, m), 7.30-7.25 (2H, m), 7.20-7.15 (1H, m), 4.04 (1H, dd), 3.75 (3H, s), 3.13-2.98 (2H, m), 2.86-2.78 (1H, m), 2.52 (2H, dd), 1.89-1.84 (2H, m)

Preparation of a Compound of Formula 15-1

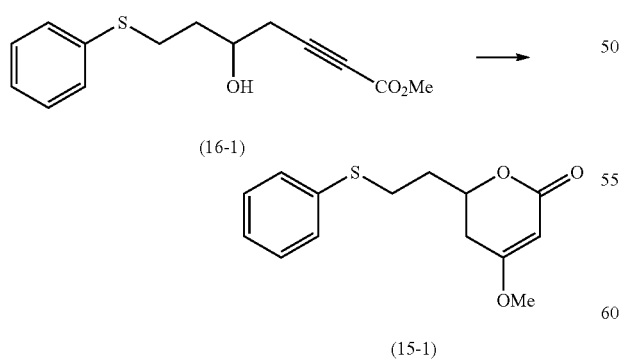

At RT, the compound of formula (16-1) 2.67 g was dissolved in methanol 60 ml. The resulting solution was cooled to 0° C. and thereto was added 28% sodium methoxide solution 0.65 g, and the resulting mixture was stirred at the same temperature for about 1 hour and then raised to RT, and stirred for about 12 hours. To the resulting reaction solution was then added aqueous saturated ammonium chloride solution, and the resulting mixture was extracted with ethyl acetate and the ethyl acetate layer was dried over anhydrous $Na_2SO_4$ and concentrated under reduced pressure, and purified by column chromatography using ($SiO_2$) by eluting EtOAc:hexane (1:2) to afford a compound of formula (15-1) 2 g (yield 75%).

$^1$H NMR ($CDCl_3$)

δ ppm: 7.35-7.27 (4H, m), 7.21-7.17 (1H, m), 5.13 (1H, s), 4.60-4.53 (1H, m), 3.73 (3H, s), 3.20-3.14 (1H, m), 3.09-3.02 (1H, m), 2.53-2.45 (1H, m), 2.34-2.28 (1H, m), 2.16-2.07 (1H, m), 1.94-1.85 (1H, m)

Preparation of a Compound of Formula 4-1

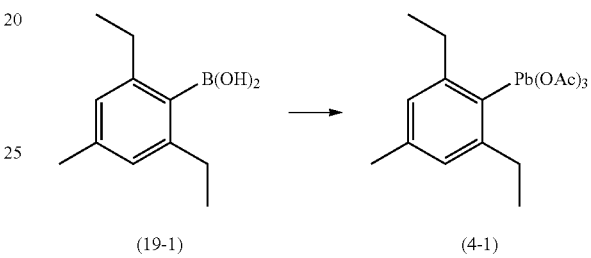

At RT under nitrogen atmosphere, lead tetraacetate 26.5 g, mercury acetate 0.83 g and a compound of formula (19-1) 10 g were dissolved in chloroform 110 ml. The resulting solution was stirred at RT under nitrogen atmosphere for 15 minutes. The resulting solution was then stirred at 40° C. under nitrogen atmosphere for 4 hours. The reaction solution was cooled to RT and then filtered through Celite (registered trademark) and the filtrate was concentrated under reduced pressure to afford yellow oil. To the obtained oil was added hexane, and the resulting mixture was concentrated under reduced pressure to afford yellow solid. At RT under nitrogen atmosphere, the obtained solid was dissolved in chloroform 260 ml. To the resulting solution was added potassium carbonate 86.2 g and the resulting mixture was stirred for 10 minutes. The reaction solution was then filtered through Celite (registered trademark) and the filtrate was concentrated under reduced pressure to afford a compound of formula (4-1) 21 g.

Also, a compound of formula (19-1) can be prepared according to a method described in WO 2010/113986 or a similar method thereto.

$^1$H NMR ($CDCl_3$)

δ ppm: 7.05 (2H, s), 2.90 (4H, m), 2.35 (3H, s), 2.06 (9H, s), 1.33-1.27 (6H, m)

Preparation of a Compound of Formula 1-4

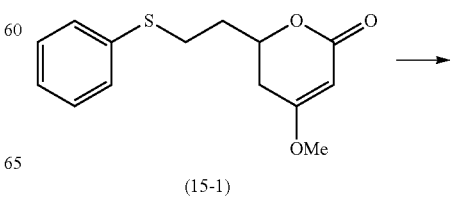

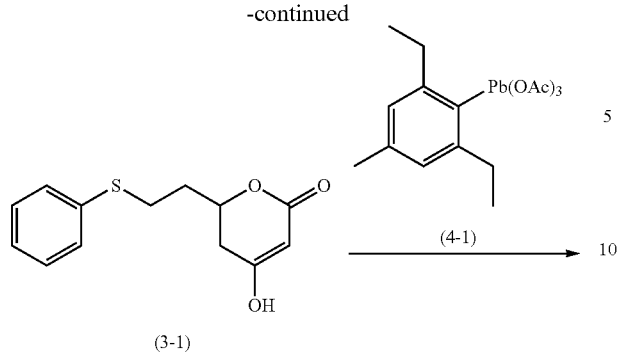

(3-1) → (4-1)

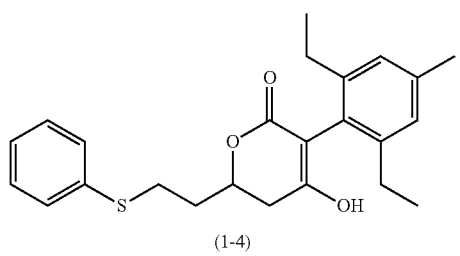

(1-4)

At RT, the compound of formula (15-1) 1.17 g was dissolved in diethyl ether 15 ml. To the resulting solution was added at RT concentrated hydrochloric acid 0.6 ml, and the resulting mixture was stirred at the same temperature for about 12 hours. The resulting reaction solution was then concentrated under reduced pressure and purified by column chromatography using (SiO$_2$) by eluting EtOAc:hexane (3:1) to afford crude product of a compound of formula (3-1) 700 mg.

Successively, at RT under nitrogen atmosphere, the compound of formula (3-1) 430 mg and dimethylamino pyridine 1.05 g were dissolved in a mixed solution of chloroform 4.8 ml and toluene 1.2 ml. The resulting solution was stirred at RT under nitrogen atmosphere for 15 minutes. To the resulting solution was then added under nitrogen atmosphere the compound of formula (4-1) 1.0 g. Under nitrogen atmosphere, the resulting mixture was stirred at 80° C. for 1 hour. The resulting reaction solution was cooled to RT and adjusted with 2N hydrochloric acid to make pH 1 and filtered through Celite (registered trademark), and the filtrate was extracted with chloroform. The obtained chloroform layer was washed with water and dried over anhydrous Na$_2$SO$_4$ and filtered. The obtained filtrate was concentrated under reduced pressure to afford yellow oil. The obtained oil was by purified by column chromatography using (SiO$_2$) by eluting EtOAc:hexane (1:4) to afford a compound of formula (1-4) 71 mg.

$^1$H NMR (CDCl$_3$)

δ ppm: 7.39-7.19 (5H, m), 7.00 (1H, s), 6.98 (1H, s), 5.65 (1H, s), 4.75-4.68 (1H, m), 3.26-3.10 (2H, m), 2.75-1.96 (11H, m), 1.14-1.07 (6H, m)

Preparation Example 1-4

Preparation of a Compound of Formula (1-5)

Preparation of a Compound of Formula 4-2

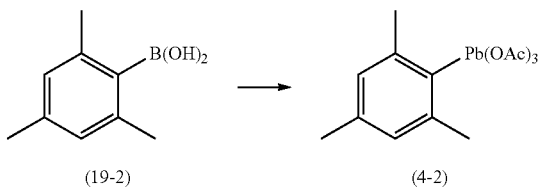

(19-2) → (4-2)

At RT under nitrogen atmosphere, lead tetraacetate 6.2 g, mercury acetate 194 mg and a compound of formula (19-2) g were dissolved in chloroform 25 ml. The resulting solution was stirred at RT under nitrogen atmosphere for 15 minutes. The reaction solution was then stirred at 40° C. under nitrogen atmosphere for 4 hours. The reaction solution was cooled to RT and filtered through Celite (registered trademark), and the filtrate was then concentrated under reduced pressure to afford yellow oil. To the obtained oil was added hexane and the resulting mixture was concentrated under reduced pressure to afford yellow solid. At RT under nitrogen atmosphere, the obtained solid was dissolved in chloroform 50 ml. To the resulting solution was added potassium carbonate 20 g and the resulting mixture was stirred for 10 minutes. The reaction solution was then filtered through Celite (registered trademark). The resulting filtrate was concentrated under reduced pressure to afford a compound of formula (4-2) 4 g.

$^1$H NMR (CDCl$_3$)

δ ppm: 6.99 (2H, s), 2.57 (6H, s), 2.30 (3H, s), 2.06 (9H, s)

Preparation of a Compound of Formula 1-5

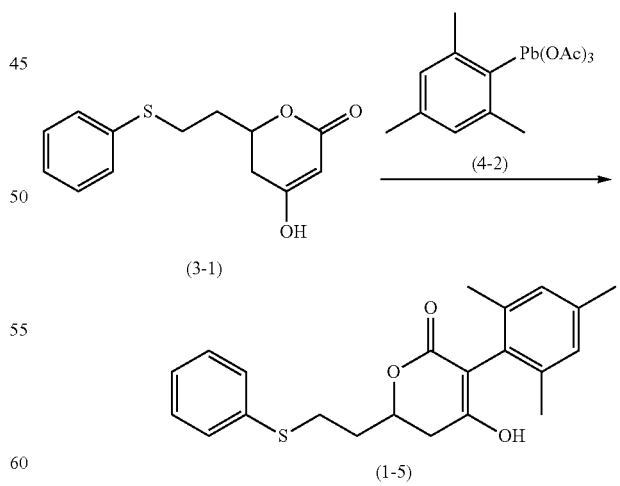

(3-1) → (1-5)

At RT under nitrogen atmosphere, a compound of formula (3-1) 250 mg and dimethylaminopyridine 610 mg were dissolved in a mixed solution of chloroform 2.5 ml and toluene 0.5 ml. The resulting solution was stirred at RT under nitrogen atmosphere for 15 minutes. Under nitrogen atmosphere, to the resulting solution was then added a compound of formula (4-2) 560 mg. Under nitrogen atmosphere, the resulting mixture was stirred at 80° C. for 1 hour. The resulting reaction solution was cooled to RT and adjusted with 2N hydrochloric acid to make pH 1, and filtered through Celite (registered trademark) and the filtrate was extracted with chloroform. The resulting chloroform layer was washed with water and dried over anhydrous Na₂SO₄ and filtered. The resulting filtrate was concentrated under reduced pressure to afford yellow oil. The obtained oil was purified by column chromatography using (SiO₂) by eluting EtOAc:hexane (1:4) to afford a compound of formula (1-5) 155 mg.

¹H NMR (CDCl₃)

δ ppm: 7.39-7.18 (5H, m), 6.94 (2H, s), 5.73 (1H, s), 4.75-4.67 (1H, m), 3.25-3.09 (2H, m), 2.73-2.66 (1H, m), 2.55-2.49 (1H, m), 2.28-2.06 (10H, m), 2.04-1.94 (1H, m)

Preparation Example 1-5

Preparation of a Compound of Formula (1-6)

Preparation of a Compound of Formula 4-3

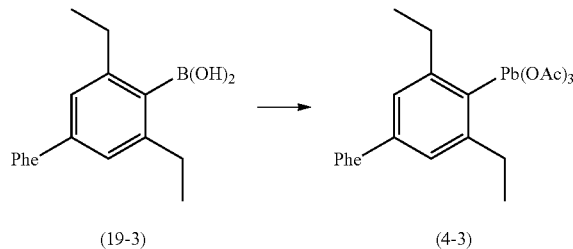

At RT under nitrogen atmosphere, lead tetraacetate 8.4 g, mercury acetate 263 mg and a compound of formula (19-3) 4.2 g were dissolved in chloroform 35 ml. The resulting solution was stirred at RT under nitrogen atmosphere for 15 minutes. The reaction solution was then stirred at 40° C. under nitrogen atmosphere for 4 hours. The reaction solution was cooled to RT and filtered through Celite (registered trademark), and the resulting filtrate was concentrated under reduced pressure to afford yellow oil. To the resulting oil was added hexane and the resulting mixture was concentrated under reduced pressure to afford yellow solid. At RT under nitrogen atmosphere, the obtained solid was dissolved in chloroform 80 ml. To the resulting solution was added potassium carbonate 27.4 g and the resulting mixture was stirred for 10 minutes. The reaction solution was then filtered through Celite (registered trademark) and the filtrate was concentrated under reduced pressure to afford a compound of formula (4-3) 6.4 g.

Also, the compound of formula (19-3) can be prepared according to a method described in WO 2010/113986 or a similar method thereto.

¹H NMR (CDCl₃)

δ ppm: 7.60-7.31 (7H, m), 3.06-2.93 (4H, m), 2.07 (9H, s), 1.39-1.32 (6H, m)

Preparation of a Compound of Formula 1-6

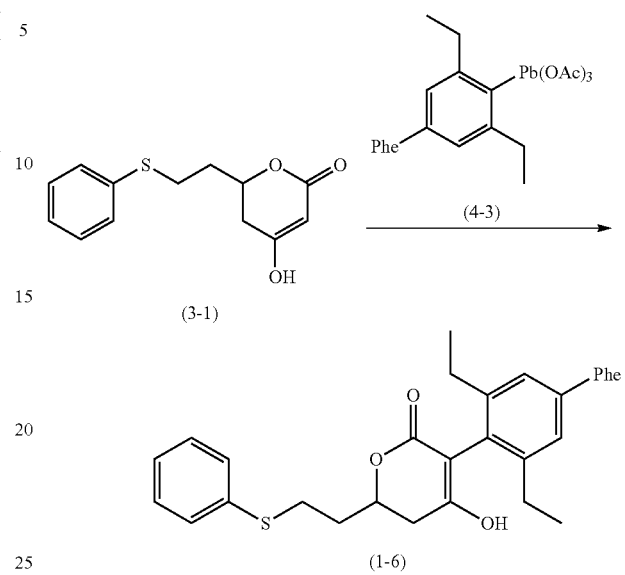

At RT under nitrogen atmosphere, a compound of formula (3-1) 250 mg and dimetylaminopyridine 610 mg were dissolved in a mixed solution of chloroform 2.5 ml and toluene 0.5 ml. The resulting solution was stirred at RT under nitrogen atmosphere for 15 minutes. To the resulting solution was then added under nitrogen atmosphere the compound of formula (4-3) 653 mg. Under nitrogen atmosphere, the resulting mixture was stirred at 80° C. for 1 hour. The resulting reaction solution was cooled to RT and adjusted with 2N hydrochloric acid to make pH 1, and filtered through Celite (registered trademark) and the filtrate was extracted with chloroform. The obtained chloroform layer was washed with water and dried over Na₂SO₄ and filtered. The obtained filtrate was concentrated under reduced pressure to afford yellow oil. The obtained oil was purified by column chromatography (SiO₂) by eluting with EtOAc:hexane (1:4) to afford a compound of formula (1-6) 149 mg.

¹H NMR (CDCl₃)

δ ppm: 7.59 (2H, dd), 7.47-7.19 (10H, m), 5.84 (1H, d), 4.78-4.71 (1H, m), 3.27-3.11 (2H, m), 2.78-2.71 (1H, m), 2.60-2.45 (5H, m), 2.29-2.20 (1H, m), 2.06-1.97 (1H, m), 1.20-1.13 (6H, m)

The present compound as shown below was prepared according to a process of Preparation example 1-3 using paratrifluoromethylthioanisole instead of thioanisole.

Compound of Formula 1-7

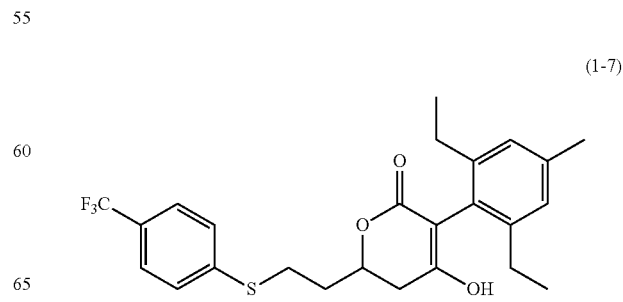

¹H NMR (CDCl₃)

δ ppm: 7.54 (2H, d), 7.42 (2H, d), 7.01 (1H, s), 6.99 (1H, s), 5.61 (1H, s), 4.75-4.68 (1H, m), 3.36-3.29 (1H, m), 3.25-3.17 (1H, m), 2.79-2.71 (1H, m), 2.61-2.53 (1H, m), 2.49-2.23 (8H, m), 2.08-1.99 (1H, m), 1.11 (6H, dt)

Preparation Example 1-6

Preparation of a Compound of Formula (1-8)

Preparation of a Compound of Formula 1-8

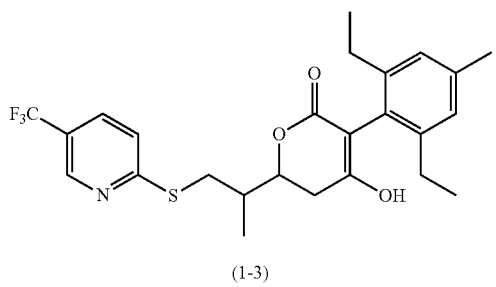

(1-3)

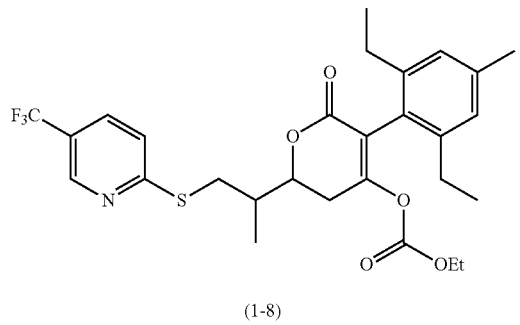

(1-8)

To the compound of formula (1-3) 150 mg were added triethylamine 0.07 ml and anhydrous tetrahydrofuran 1 ml drop wise. To the resulting mixed solution was added under ice-cooling a solution of ethyl chloroformate 0.06 ml in anhydrous tetrahydrofuran 1 ml drop wise. The resulting mixture was stirred at RT for 2 hours. To the resulting mixture was added water 5 ml and the resulting mixture was extracted with chloroform. The obtained chloroform layer was dried over anhydrous Na₂SO₄ and concentrated under reduced pressure, and purified by column chromatography (SiO₂) by eluting with EtOAc:hexane (1:6) to afford a compound of formula (1-8) 200 mg.

¹H NMR (CDCl₃)

δ ppm: 8.68-8.66 (1H, m), 7.67 (1H, dd), 7.31 (1H, dd), 6.95 (1H, s), 6.91 (1H, s), 4.83-4.62 (1H, m), 4.19-4.00 (2H, m), 3.71 (0.5H, dd), 3.50 (0.5H, dd), 3.34-3.16 (2H, m), 2.68 (1H, ddd), 2.48-2.32 (8H, m), 1.27-1.20 (6H, m), 1.16-1.05 (6H, m)

The present compound shown below was prepared according to Preparation example 1-6 using pivaloyl chloroformate instead of ethyl chloroformate.

Compound of Formula 1-9

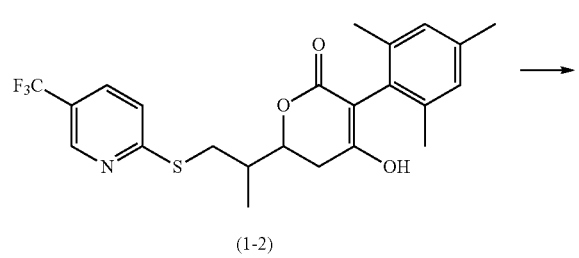

(1-9)

¹H NMR (CDCl₃)

δ ppm: 8.66 (1H, dd), 7.68 (1H, dd), 7.31 (1H, dd), 6.91 (1H, s), 6.87 (1H, s), 4.89-4.64 (1H, m), 3.71 (0.5H, dd), 3.49 (0.5H, dd), 3.36-3.07 (2H, m), 2.67-2.19 (9H, m), 1.28-1.06 (9H, m), 0.91 (9H, d)

Preparation Example 1-7

Preparation of a Compound of Formula (1-10)

Preparation of a Compound of Formula 1-10

(1-2)

(1-10)

To a compound of formula (1-2) 250 mg was added at RT chloroform 5 ml. The resulting mixed solution was cooled to 0° C. with stirring, and thereto was added a solution of meta-chloroperoxybenzoic acid 124 mg dissolved in chloroform 5 ml drop wise and the resulting mixture was stirred for about 30 minutes and then raised to RT, and stirred at RT for 3 hours. The reaction solution was diluted with chloroform and washed with 10% aqueous sodium sulfite solution. The resulting chloroform layer was washed with saturated saline and dried over anhydrous Na₂SO₄ and filtered. The obtained filtrate was concentrated under reduced pressure to afford oil. The obtained oil was purified by column chromatography (SiO₂) by eluting with EtOAc:hexane (3:1) to afford a compound of formula (1-10) 105 mg.

¹H NMR (CDCl₃)

δ ppm: 8.89 (2H, d), 8.22-8.18 (2H, m), 6.93 (2H, s), 4.61-4.55 (1H, m), 3.62-3.51 (0.5H, m), 3.29 (0.5H, dd), 3.11-2.42 (4H, m), 2.27 (3H, s), 2.16-2.09 (6H, m), 1.46-1.21 (3H, m)

The present compound shown below was prepared according to Preparation example 1-7 using a compound of formula (1-3) instead of a compound of formula (1-2).

Compound of Formula 1-11

(1-11)

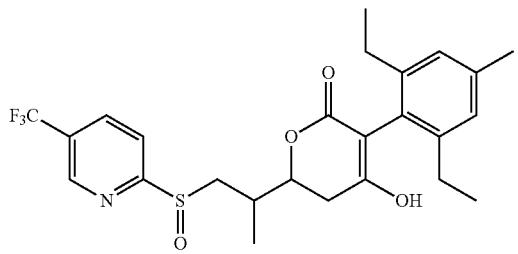

¹H NMR (CDCl₃)

δ ppm: 8.90-8.87 (1H, m), 8.22-8.13 (2H, m), 6.99-6.96 (2H, m), 4.59-4.43 (1H, m), 3.62-3.52 (0.5H, m), 3.35-3.25 (0.5H, m), 3.10-2.24 (11H, m), 1.28-1.21 (3H, m), 1.16-1.06 (6H, m)

The present compound shown below was prepared according to Preparation example 1-7 using a compound of formula (1-7) instead of a compound of formula (1-2).

Compound of Formula 1-12

(1-12)

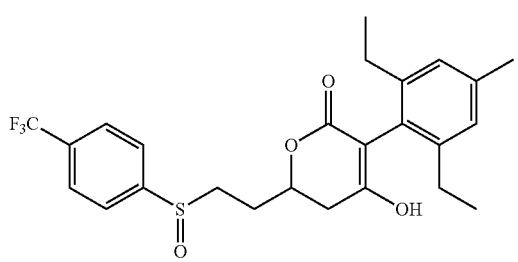

¹H NMR (CDCl₃)

δ ppm: 7.83-7.73 (4H, m), 6.99-6.96 (2H, m), 6.33 (1H, s), 4.75-4.50 (1H, m), 3.35-1.89 (13H, m), 1.15-1.03 (6H, m)

Preparation Example 1-8

Preparation of a Compound of Formula (1-13)

Preparation of a Compound of Formula 1-13

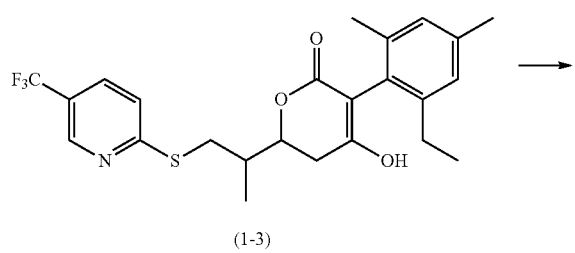

(1-3)

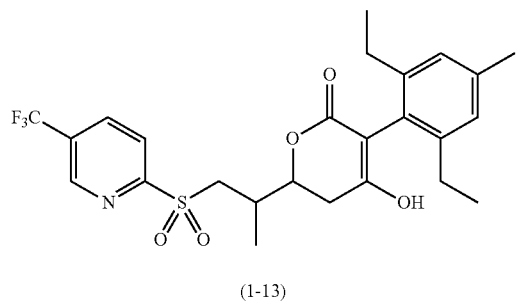

(1-13)

At RT, to a compound of formula (1-3) 150 mg was added chloroform 1 ml and the resulting mixture was cooled to 0° C. with stirring, and thereto was added a solution of meta-chloroperoxybenzoic acid 260 mg dissolved in chloroform 2 ml drop wise and the resulting mixture was stirred for about 30 minutes. The resulting reaction solution was then raised to RT and stirred at RT for 3 hours. The reaction solution was diluted with chloroform and washed with 10% aqueous sodium sulfite solution. The resulting chloroform layer was washed with saturated saline and dried over anhydrous Na₂SO₄ and filtered. The obtained filtrate was concentrated under reduced pressure to afford oil. The obtained oil was purified by column chromatography (SiO₂) by eluting with EtOAc:hexane (1:2) to afford a compound of formula (1-13) 77.2 mg.

¹H NMR (CDCl₃)

δ ppm: 9.02 (1H, s), 8.26 (2H, s), 7.01 (1H, s), 6.98 (1H, s), 4.85-4.81 (0.5H, m), 4.50-4.44 (0.5H, m), 3.95-3.83 (1H, m), 3.53-3.40 (1H, m), 2.91-2.33 (10H, m), 1.39-1.31 (3H, m), 1.15-1.09 (6H, m)

The present compound shown below was prepared according to Preparation example 1-8 using a compound of formula (1-7) instead of a compound of formula (1-3).

Compound of Formula 1-14

(1-14)

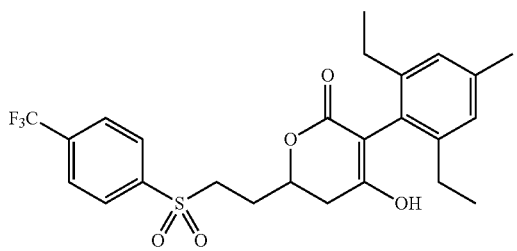

¹H NMR (CDCl₃)

δ ppm: 8.09 (2H, d), 7.98 (2H, d), 7.00 (1H, s), 6.98 (1H, s), 4.73-4.66 (1H, m), 3.58-3.33 (2H, m), 2.80-2.59 (2H, m), 2.49-2.17 (9H, m), 1.13-1.08 (6H, m)

Next, the formulation examples are shown below. Here the present compound is expressed as the number of a structural formula.

Formulation 1
Wettable Powder

| | |
|---|---|
| Compound (1-1) | 50% by weight |
| Sodium ligninsulfonate | 5% by weight |
| Polyoxyethylene alkyl ether | 5% by weight |
| White carbon | 5% by weight |
| Clay | 35% by weight |

The ingredients shown above are mixed and ground to obtain a wettable powder.

The compound (1-1) is replaced with any of the compounds (1-2) to (1-14) to obtain respective formulations.

Formulation 2
Granules

| | |
|---|---|
| Compound (1-1) | 1.5% by weight |
| Sodium ligninsulfonate | 2% by weight |
| Talc | 40% by weight |
| Bentonite | 56.5% by weight |

The ingredients shown above are mixed, and thereto is added water, and the resulting mixture is fully kneaded, and is then subjected to granulation and drying to obtain a granule.

The compound (1-1) is replaced with any of the compounds (1-2) to (1-14) to obtain respective formulations.

Formulation 3
Suspension Concentrates

| | |
|---|---|
| Compound (1-1) | 10% by weight |
| Mixture of polyoxyethylene alkylether sulfate ammonium salt and white carbon (weight ratio 1:1) | 35% by weight |
| Water | 55% by weight |

The ingredients shown above are mixed, and the resulting mixture is then subjected to fine grinding according to wet grinding method, to obtain a suspension concentrate.

The compound (1-1) is replaced with any of the compounds (1-2) to (1-14) to obtain respective formulations.

Next, test examples are shown below.

Here an efficacy for controlling weeds on the present compound was visually observed and evaluated in 11 criteria of 0 to 10 (0 represents no action, 10 represents complete death and the intermediate efficacy were evaluated in 1 to 9 criteria).

Test 1-1 Post-emergence Treatment Test

Commercial soil for propagation was put in a pot measuring 8 cm in diameter and 6.5 cm in height, and in the pot, seeds of *Echinochloa crus-galli* were sown, and then covered with soil of about 0.5 cm thickness and the plants were grown in a greenhouse. When the plants were grown to 1-2 leaf stages, a predetermined amount of a chemical diluted solution containing a compound (1-1) was uniformly spayed on the whole plants. Here the chemical diluted solution was prepared by dissolving a predetermined amount of the compound (1-1) in dimethylformamide solution containing 2% of Tween 20 (polyoxyetylene sorbitan fatty acid ester) (manufactured by MP Biomedicals Inc.) and then diluting the solution with deionized water. After spraying, plants were grown in a greenhouse and after 20 days of the treatment, the efficacy for *Echinochloa crus-galli* was observed and the controlling effect was evaluated.

Similarly, the present compounds (1-2) to (1-11) and (1-13) were also tested.

As a result, compounds (1-1) to (1-11) and (1-13) were all shown an efficacy of 9 or more at a treatment amount of chemicals of 1,000 g/10,000 m².

Test 1-2 Post-emergence Treatment Test

Commercial soil for propagation was put in a pot measuring 8 cm in diameter and 6.5 cm in height, and in the pot, seeds of *Galium aparine* were sown, and then covered with soil of about 0.5 cm thickness and the plants were grown in a greenhouse. When the plants were grown to 1-2 leaf stages, a predetermined amount of a chemical diluted solution containing a compound (1-1) was uniformly spayed on the whole plants. Here the chemical diluted solution was prepared similarly to the test example 1-1. After spraying, plants were grown in a greenhouse and after 20 days of the treatment, the efficacy for *Galium aparine* was observed and evaluated.

Similarly, the present compounds (1-1) and (1-10) was also tested.

As a result, compounds (1-1), (1-2) and (1-10) were all shown an efficacy of 7 or more at a treatment amount of chemicals of 1,000 g/10,000 m².

Test 2-1 Pre-emergence Treatment Test

Steam sterilized field soil was put in a pot measuring cm in diameter and 6.5 cm in height, and in the pot, seeds of *Echinochloa crus-galli* were sown, and then covered with soil of about 0.5 cm thickness. Then a predetermined amount of a chemical diluted solution containing a compound (1-1) was uniformly spayed on the soil surface. Here the chemical diluted solution was prepared similarly to the test example 1-1. After chemical treatment, plants were grown in a greenhouse, and after 3 weeks of the spraying, the efficacy for *Echinochloa crus-galli* was observed and evaluated.

Similarly, the present compounds (1-2) to (1-8), (1-10), (1-11) and (1-13) were also tested.

As a result, compounds (1-2) to (1-8), (1-10), (1-11) and (1-13) were all shown an efficacy of 7 or more at a treatment amount of chemicals of 1,000 g/10,000 m².

The invention claimed is:

1. A dihydropyrone compound of formula (I):

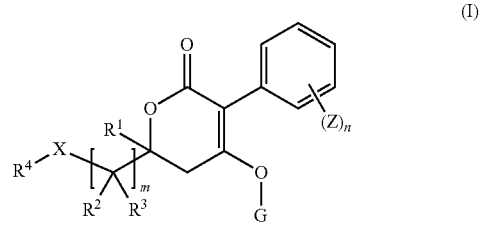

wherein:
m is 1, 2 or 3;
n is an integer of 1 to 5;
X represents O, S, S(O) or S(O)$_2$;
R$^1$ represents a hydrogen atom or a methyl group;
R$^2$ and R$^3$ represent independently of each other a hydrogen atom, a halogen atom, an C$_{1-6}$ alkyl group, a C$_{1-6}$ haloalkyl group, a C$_{3-8}$ cycloalkyl group or a C$_{3-8}$ halocycloalkyl group, alternatively R$^2$ and R$^3$ connect to each other to represent an C$_{2-5}$ alkylene chain, or R$^2$ and R$^3$ combine with each other to represent an C$_{1-3}$ alkylidene group optionally having one or more halogen atoms, with the proviso that when m is 2 or 3, two or three R$^2$ may be the same or different to each other and two or three R$^3$ may be the same or different to each other;

R⁴ represents a $C_{6-10}$ aryl group or a five- to six-membered heteroaryl group, with the proviso that the $C_{6-10}$ aryl group and the five- or six-membered heteroaryl group may have optionally one or more substituents selected from the group consisting of a halogen atom, a cyano group, a nitro group, an amino group, an ($C_{1-6}$ alkyl)amino group, an ($C_{1-6}$ alkyl)($C_{1-6}$ alkyl)amino group, a pentafluorothio group, an $C_{1-6}$ alkyl group, an $C_{2-6}$ alkenyl group, an $C_{2-6}$ alkynyl group, an $C_{1-6}$ alkoxy group, an $C_{1-6}$ alkylthio group, an $C_{3-6}$ alkenyloxy group, an $C_{3-6}$ alkynyloxy group, an $C_{6-10}$ aryl group, an $C_{6-10}$ aryloxy group, an $C_{1-6}$ alkylsulfinyl group, an $C_{1-6}$ alkylsulfonyl group, a hydroxyl group, an ($C_{1-6}$ alkyl)carbonyl group, a hydroxycarbonyl group, a ($C_{1-6}$ alkoxy)carbonyl group and an ($C_{6-10}$ aryl)$C_{1-6}$ alkoxy group, and when two or more substituents exist, the substituents may be the same or different to each other; and the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the ($C_{1-6}$ alkoxy)carbonyl group and the ($C_{6-10}$ aryl)$C_{1-6}$ alkoxy group may each have one or more halogen atoms or $C_{1-3}$ haloalkyl groups, and when two or more halogen atoms or $C_{1-3}$ haloalkyl groups exist, the halogen atoms or the $C_{1-3}$ haloalkyl groups may be the same or different to each other respectively;

G represents a hydrogen atom or a group of any one of the following formulae:

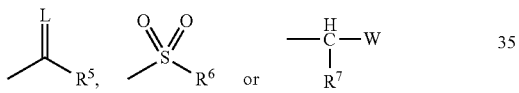

wherein
L represents O or S;
R⁵ represents an $C_{1-6}$ alkyl group, a $C_{3-8}$ cycloalkyl group, an $C_{2-6}$ alkenyl group, an $C_{2-6}$ alkynyl group, an $C_{6-10}$ aryl group, an ($C_{6-10}$ aryl)$C_{1-6}$ alkyl group, an $C_{1-6}$ alkoxy group, a $C_{3-8}$ cycloalkoxy group, an $C_{3-6}$ alkenyloxy group, an $C_{3-6}$ alkynyloxy group, an $C_{6-10}$ aryloxy group, an ($C_{6-10}$ aryl)$C_{1-6}$ alkoxy group, an ($C_{1-6}$ alkyl)($C_{1-6}$ alkyl)amino group, an ($C_{3-6}$ alkenyl)($C_{3-6}$ alkenyl)amino group, an ($C_{1-6}$ alkyl)($C_{6-10}$ aryl) amino group or a five- to six-membered heteroaryl group, with the proviso that these groups may each have one or more halogen atoms, and when two or more halogen atoms exist, the halogen atoms may be the same or different to each other; and the $C_{3-8}$ cycloalkyl group, the $C_{6-10}$ aryl group, an aryl moiety of the ($C_{6-10}$ aryl)$C_{1-6}$ alkyl group, the $C_{3-8}$ cycloalkoxy group, the $C_{6-10}$ aryloxy group, an aryl moiety of the ($C_{6-10}$ aryl)$C_{1-6}$ alkoxy group, an aryl moiety of the ($C_{1-6}$ alkyl)($C_{6-10}$ aryl)amino group and a five- to six-membered heteroaryl group may each have one or more $C_{1-6}$ alkyl groups, and when two or more $C_{1-6}$ alkyl groups exist, the alkyl groups may be the same or different to each other;
R⁶ represents an $C_{1-6}$ alkyl group, an $C_{6-10}$ aryl group or an ($C_{1-6}$ alkyl)($C_{1-6}$ alkyl)amino group, with the proviso that these groups may each have one or more halogen atoms and when two or more halogen atoms exist, the halogen atoms may be the same or different to each other; and the $C_{6-10}$ aryl group may have optionally one or more $C_{1-6}$ alkyl groups and when two or more $C_{1-6}$ alkyl groups exist, the alkyl groups may be the same or different to each other;
R⁷ represents a hydrogen atom or an $C_{1-6}$ alkyl group;
W represents an $C_{1-6}$ alkoxy group, an $C_{1-6}$ alkylthio group, an $C_{1-6}$ alkylsulfinyl group or an $C_{1-6}$ alkylsulfonyl group, with the proviso that these groups may each have one or more halogen atoms and when two or more halogen atoms exist, the halogen atoms may be the same or different to each other;
Z represents a halogen atom, a cyano group, a nitro group, an $C_{1-6}$ alkyl group, an $C_{2-6}$ alkenyl group, an $C_{2-6}$ alkynyl group, an $C_{1-6}$ alkoxy group, an ($C_{1-6}$ alkyl) carbonyl group, an $C_{1-6}$ alkylthio group, an $C_{6-10}$ aryloxy group, a five- or six-membered heteroaryloxy group, a $C_{3-8}$ cycloalkyl group, an $C_{6-10}$ aryl group or a five- to six-membered heteroaryl group, with the proviso that the $C_{1-6}$ alkyl group, the $C_{2-6}$ alkenyl group, the $C_{2-6}$ alkynyl group, the $C_{1-6}$ alkoxy group, the ($C_{1-6}$ alkyl)carbonyl group and the $C_{1-6}$ alkylthio group may each have one or more halogen atoms, and when two or more halogen atoms exist, the halogen atoms may be the same or different to each other; and the $C_{6-10}$ aryl group, the five- to six-membered heteroaryl group, the $C_{6-10}$ aryloxy group and the five- to six-membered heteroaryloxy group may each have one or more substituents selected from the group consisting of a halogen atom, an $C_{1-6}$ alkyl group and a $C_{1-6}$ haloalkyl group, and when two or more substituents exist, the substituents may be the same or different to each other; and the $C_{3-8}$ cycloalkyl group may have optionally one or more substituents selected from the group consisting of a halogen atom and an $C_{1-6}$ alkyl group, and when two or more substituents exist, the substituents may be the same or different to each other; when n is an integer of 2 or more, Z may be the same or different to each other.

2. The dihydropyrone compound according to claim 1 wherein
m is 1, 2 or 3;
n is an integer of any one of 1 to 3;
R¹ resents a hydrogen atom or a methyl group;
R² and R³ represent independently of each other a hydrogen atom or an $C_{1-3}$ alkyl group, alternatively R² and R³ connect with each other to represent an $C_{2-5}$ alkylene chain, with the proviso that when m is 2 or 3, two or three R² may be the same or different to each other and two or three R³ may be the same or different to each other;
G represents a hydrogen atom or a group of any one of the following formulae:

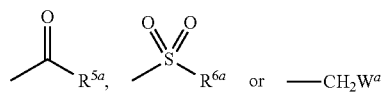

wherein
R⁵ᵃ represents an $C_{1-6}$ alkyl group, an $C_{6-10}$ aryl group, an $C_{1-6}$ alkoxy group, an $C_{3-6}$ alkenyloxy group, an $C_{3-6}$ alkynyloxy group or an $C_{6-10}$ aryloxy group;
R⁶ᵃ represents an $C_{1-6}$ alkyl group; and
Wᵃ represents an $C_{1-3}$ alkoxy group;
Z represents a halogen atom, an $C_{1-3}$ alkyl group, an $C_{2-6}$ alkenyl group, an $C_{2-6}$ alkynyl group, an $C_{1-3}$ alkoxy group, a $C_{3-8}$ cycloalkyl group, a nitro group, a phenyl group or a five- to six-membered heteroaryloxy group, with the proviso that the $C_{1-3}$ alkyl group, the $C_{2-6}$ alkenyl group, the $C_{2-6}$ alkynyl group, the $C_{1-3}$ alkoxy group, the phenyl group and the five- to six-membered heteroaryloxy group may have optionally one or more halogen atoms, and when two or more halogen atoms exist, the halogen atoms may be the same or different to each other.

3. The dihydropyrone compound according to claim 2, wherein
m is 2;
$R^2$ and $R^3$ represents independently of each other a hydrogen atom, a methyl group or an ethyl group, alternatively $R^2$ and $R^3$ connect with each other to represent an ethylene chain, with the proviso that two $R^2$ may be the same or different to each other and two $R^3$ may be the same or different to each other;
G represents a hydrogen atom, an acetyl group, a propionyl group, a butylcarbonyl group, a benzoyl group, a methylsulfonyl group, a methoxycarbonyl group, an ethoxycarbonyl group, an allyloxycarbonyl group, a phenoxycarbonyl group, a methoxymethyl group or an ethoxymethyl group;
$R^9$ represents a hydrogen atom, a 2-nitrophenylsulfonyl group or a methyl group;
Z represents a methyl group, an ethyl group, a phenyl group, a vinyl group, a cyclopropyl group, a nitro group, a fluorine atom, a chlorine atom, a bromine atom, a methoxy group, a trifluoromethyl group, a 5-trifluoromethyl-2-chloropyridyloxy group or an ethynyl group.

4. The dihydropyrone compound according to claim 1, wherein
X represents S, S(O) or S(O)$_2$; and
$R^4$ represents a phenyl group, a 2-pyridyl group, a 3-pyridyl group, a 4-pyridyl group, a 2-pyrimidinyl group, a 2-furyl group, a 2-thienyl group or a 2-thiazolyl group, an 2-oxazolyl group, a 2-(1,3,4-thiadiazolyl) group or a 5-tetrazoly group, with the proviso that the phenyl group, the 2-pyridyl group, the 3-pyridyl group, the 4-pyridyl group, the 2-pyrimidinyl group, the 2-furyl group, the 2- thienyl group, the 2-thiazolyl group, the 2-oxazolyl group, the 2-(1,3,4-thiadiazolyl) group or the 5-tetrazoly group may have optionally one or more substituents selected from the group consisting of a halogen atom, an $C_{1-3}$ alkyl group, a hydroxyl group, an ($C_{1-3}$ alkyl)carbonyl group, a ($C_{1-3}$ alkoxy)carbonyl group, an $C_{1-3}$ alkoxy group, a $C_{1-3}$ haloalkyl group, an $C_{1-3}$ alkylthio group, a $C_{1-3}$ haloalkylthio group, a cyano group, a nitro group, an amino group, a pentafluorothio group, a benzoylamino group and a $C_{1-3}$ haloalkoxy group, and when two or more substituents exist, the substituents may be the same or different to each other.

5. The dihydropyrone compound according to claim 4, wherein
X represents S, S(O) or S(O)$_2$; and
$R^4$ represents a phenyl group, a 2-pyridyl group, a 3-pyridyl group, a 4-pyridyl group, a 2-pyrimidinyl group, a 2-furyl group, a 2-thienyl group, a 2-thiazolyl group, an 2-oxazolyl group, a 2-(1,3,4-thiadiazolyl) group or a 5-tetrazoly group, with the proviso that the phenyl group, the 2-pyridyl group, the 3-pyridyl group, the 4-pyridyl group, the 2-pyrimidinyl group, the 2-furyl group, the 2-thienyl group, the 2-thiazolyl group, the 2-oxazolyl group, the 2-(1,3,4-thiadiazolyl) group or the 5-tetrazoly group may have optionally one or more substituents selected from the group consisting of a chlorine atom, a bromine atom, an iodine atom, a fluorine atom, a methyl group, an ethyl group, an isopropyl group, a t-butyl group, a methoxy group, a nitro group, an amino group, a cyano group, a hydroxyl group, an acetyl group, a methoxycarbonyl group, a pentafluorothio group, a pentafluoroethyl group, a difluoroethyl group, a heptafluoroisopropyl group, a trifluoromethylthio group, a benzoylamino group, a trifluoromethoxy group and a trifluoromethyl group.

6. The dihydropyrone compound according to claim 1, wherein
X represents O; and
$R^4$ represents a phenyl group, a 2-pyridyl group, a 3-pyridyl group, a 4-pyridyl group, a 2-pyrimidinyl group, a 2-furyl group, a 2-thienyl group, a 2-thiazolyl group, an 2-oxazolyl group, a 2-(1,3,4-thiadiazolyl) group or a 5-tetrazoly group, with the proviso that the phenyl group, the 2-pyridyl group, the 3-pyridyl group, the 4-pyridyl group, the 2-pyrimidinyl group, the 2-furyl group, the 2-thienyl group, the 2-thiazolyl group, the 2-oxazolyl group, the 2-(1,3,4-thiadiazolyl) group or the 5-tetrazoly group may have optionally one or more substituents selected from the group consisting of a halogen atom, an $C_{1-3}$ alkyl group, a hydroxyl group, an ($C_{1-3}$ alkyl)carbonyl group, a ($C_{1-3}$ alkoxy)carbonyl group, an $C_{1-3}$ alkoxy group, a $C_{1-3}$ haloalkyl group, an $C_{1-3}$ alkylthio group, a $C_{1-3}$ haloalkylthio group, a cyano group, a nitro group, an amino group, a pentafluorothio group, a benzoylamino group and a $C_{1-3}$ haloalkoxy group, and when two or more substituents exist, the substituents may be the same or different to each other.

7. The dihydropyrone compound according to claim 6, wherein
X represents O; and
$R^4$ represents a phenyl group, a 2-pyridyl group, a 3-pyridyl group, a 4-pyridyl group, a 2-pyrimidinyl group, a 2-furyl group, a 2-thienyl group, a 2-thiazolyl group, an 2-oxazolyl group, a 2-(1,3,4-thiadiazolyl) group or a 5-tetrazoly group, with the proviso that the phenyl group, the 2-pyridyl group, the 3-pyridyl group, the 4-pyridyl group, the 2-pyrimidinyl group, the 2-furyl group, the 2-thienyl group, the 2-thiazolyl group, the 2-oxazolyl group, the 2-(1,3,4-thiadiazolyl) group or the 5-tetrazoly group may have optionally one or more substituents selected from the group consisting of a chlorine atom, a bromine atom, an iodine atom, a fluorine atom, a methyl group, an ethyl group, an isopropyl group, a t-butyl group, a methoxy group, a nitro group, an amino group, a cyano group, a hydroxyl group, an acetyl group, a methoxycarbonyl group, a pentafluorothio group, a pentafluoroethyl group, a difluoroethyl group, a heptafluoroisopropyl group, a trifluoromethylthio group, a benzoylamino group, a trifluoromethoxy group and a trifluoromethyl group.

8. The dihydropyrone compound according to claim 1, wherein G represents a hydrogen atom.

9. A herbicide comprising the dihydropyrone compound according to claim 1 as an active ingredient and an inert carrier.

10. A method for controlling a weed, which comprises applying an effective amount of a dihydropyrone compound of formula (I),

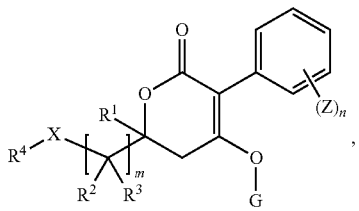

to a weed or a soil where a weed grows, wherein:

m is 1, 2 or 3;

n is an integer of 1 to 5;

X represents O, S, S(O) or S(O)$_2$;

$R^1$ represents a hydrogen atom or a methyl group;

$R^2$ and $R^3$ represent independently of each other a hydrogen atom, a halogen atom, an $C_{1-6}$ alkyl group, a $C_{1-6}$ haloalkyl group, a $C_{3-8}$ cycloalkyl group or a $C_{3-8}$ halocycloalkyl group, alternatively $R^2$ and $R^3$ connect to each other to represent an $C_{2-5}$ alkylene chain, or $R^2$ and $R^3$ combine with each other to represent an $C_{1-3}$ alkylidene group optionally having one or more halogen atoms, with the proviso that when m is 2 or 3, two or three $R^2$ may be the same or different to each other and two or three $R^3$ may be the same or different to each other;

$R^4$ represents a $C_{6-10}$ aryl group or a five- to six-membered heteroaryl group, with the proviso that the $C_{6-10}$ aryl group and the five- or six-membered heteroaryl group may have optionally one or more substituents selected from the group consisting of a halogen atom, a cyano group, a nitro group, an amino group, an $(C_{1-6}$ alkyl)amino group, an $(C_{1-6}$ alkyl)$(C_{1-6}$ alkyl)amino group, a pentafluorothio group, an $C_{1-6}$ alkyl group, an $C_{2-6}$ alkenyl group, an $C_{2-6}$ alkynyl group, an $C_{1-6}$ alkoxy group, an $C_{1-6}$ alkylthio group, an $C_{3-6}$ alkenyloxy group, an $C_{3-6}$ alkynyloxy group, an $C_{6-10}$ aryl group, an $C_{6-10}$ aryloxy group, an $C_{1-6}$ alkylsulfinyl group, an $C_{1-6}$ alkylsulfonyl group, a hydroxyl group, an $(C_{1-6}$ alkyl)carbonyl group, a hydroxycarbonyl group, a $(C_{1-6}$ alkoxy)carbonyl group and an $(C_{6-10}$ aryl)$C_{1-6}$ alkoxy group, and when two or more substituents exist, the substituents may be the same or different to each other; and the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the $(C_{1-6}$ alkoxy)carbonyl group and the $(C_{6-10}$ aryl)$C_{1-6}$ alkoxy group may each have one or more halogen atoms or $C_{1-3}$ haloalkyl groups, and when two or more halogen atoms or $C_{1-3}$ haloalkyl groups exist, the halogen atoms or the $C_{1-3}$ haloalkyl groups may be the same or different to each other respectively;

G represents a hydrogen atom or a group of any one of the following formulae:

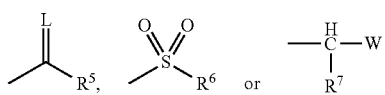

wherein

L represents O or S;

$R^5$ represents an $C_{1-6}$ alkyl group, a $C_{3-8}$ cycloalkyl group, an $C_{2-6}$ alkenyl group, an $C_{2-6}$ alkynyl group, an $C_{6-10}$ aryl group, an $(C_{6-10}$ aryl)$C_{1-6}$ alkyl group, an $C_{1-6}$ alkoxy group, a $C_{3-8}$ cycloalkoxy group, an $C_{3-6}$ alkenyloxy group, an $C_{3-6}$ alkynyloxy group, an $C_{6-10}$ aryloxy group, an $(C_{6-10}$ aryl) $C_{1-6}$ alkoxy group, an $(C_{1-6}$ alkyl)$(C_{1-6}$ alkyl)amino group, an $(C_{3-6}$ alkenyl) $(C_{3-6}$ alkenyl)amino group, an $(C_{1-6}$ alkyl)$(C_{6-10}$ aryl) amino group or a five- to six-membered heteroaryl group, with the proviso that these groups may each have one or more halogen atoms, and when two or more halogen atoms exist, the halogen atoms may be the same or different to each other; and the $C_{3-8}$ cycloalkyl group, the $C_{6-10}$ aryl group, an aryl moiety of the $(C_{6-10}$ aryl)$C_{1-6}$ alkyl group, the $C_{3-8}$ cycloalkoxy group, the $C_{6-10}$ aryloxy group, an aryl moiety of the $(C_{6-10}$ aryl)$C_{1-6}$ alkoxy group, an aryl moiety of the $(C_{1-6}$ alkyl)$(C_{6-10}$ aryl)amino group and a five- to six-membered heteroaryl group may each have one or more $C_{1-6}$ alkyl groups, and when two or more $C_{1-6}$ alkyl groups exist, the alkyl groups may be the same or different to each other;

$R^6$ represents an $C_{1-6}$ alkyl group, an $C_{6-10}$ aryl group or an $(C_{1-6}$ alkyl)$(C_{1-6}$ alkyl)amino group, with the proviso that these groups may each have one or more halogen atoms and when two or more halogen atoms exist, the halogen atoms may be same or different to each other; and the $C_{6-10}$ aryl group may have optionally one or more $C_{1-6}$ alkyl groups and when two or more $C_{1-6}$ alkyl groups exist, the alkyl groups may be same or different to each other;

$R^7$ represents a hydrogen atom or an $C_{1-6}$ alkyl group;

W represents an $C_{1-6}$ alkoxy group, an $C_{1-6}$ alkylthio group, an $C_{1-6}$ alkylsulfinyl group or an $C_{1-6}$ alkylsulfonyl group, with the proviso that these groups may each have one or more halogen atoms and when two or more halogen atoms exist, the halogen atoms may be the same or different to each other;

Z represents a halogen atom, a cyano group, a nitro group, an $C_{1-6}$ alkyl group, an $C_{2-6}$ alkenyl group, an $C_{2-6}$ alkynyl group, an $C_{1-6}$ alkoxy group, an $(C_{1-6}$ alkyl) carbonyl group, an $C_{1-6}$ alkylthio group, an $C_{6-10}$ aryloxy group, a five- or six-membered heteroaryloxy group, a $C_{3-8}$ cycloalkyl group, an $C_{6-10}$ aryl group or a five- to six-membered heteroaryl group, with the proviso that the $C_{1-6}$ alkyl group, the $C_{2-6}$ alkenyl group, the $C_{2-6}$ alkynyl group, the $C_{1-6}$ alkoxy group, the $(C_{1-6}$ alkyl)carbonyl group and the $C_{1-6}$ alkylthio group may each have one or more halogen atoms, and when two or more halogen atoms exist, the halogen atoms may be the same or different to each other; and the $C_{6-10}$ aryl group, the five- to six-membered heteroaryl group, the $C_{6-10}$ aryloxy group and the five- to six-membered heteroaryloxy group may each have one or more substituents selected from the group consisting of a halogen atom, an $C_{1-6}$ alkyl group and a $C_{1-6}$ haloalkyl group, and when two or more substituents exist, the substituents may be the same or different to each other; and the $C_{3-8}$ cycloalkyl group may have optionally one or more substituents selected from the group consisting of a halogen atom and an $C_{1-6}$ alkyl group, and when two or more substituents exist, the substituents may be the same or different to each other; when n is an integer of 2 or more, Z may be the same or different to each other.

* * * * *